United States Patent
Bays et al.

(10) Patent No.: US 6,677,316 B2
(45) Date of Patent: *Jan. 13, 2004

(54) ADENOSINE DERIVATIVES AND METHODS OF ADMINISTRATION

(75) Inventors: David Edmund Bays, Ware (GB); Richard Peter Charles Cousins, Stevenage (GB); Hazel Joan Dyke, Cambridge (GB); Colin David Eldred, Stevenage (GB); Brian David Judkins, Stevenage (GB); Martin Pass, Macclesfield (GB); Andrew Michael Kenneth Pennell, San Carlos, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/217,107

(22) Filed: Aug. 13, 2002

(65) Prior Publication Data

US 2003/0096788 A1 May 22, 2003

Related U.S. Application Data

(63) Continuation of application No. 09/736,018, filed as application No. PCT/EP99/04182 on Jun. 21, 1999, now Pat. No. 6,492,348.

(30) Foreign Application Priority Data

Jun. 23, 1998 (GB) .............................................. 9813554

(51) Int. Cl.⁷ .............................................. A61K 31/70
(52) U.S. Cl. ........................... 514/46; 514/81; 514/266; 536/27.23; 536/27.3; 536/27.63; 544/264
(58) Field of Search .......................... 514/46, 81, 266; 536/27.23, 27.3, 27.63; 544/264

(56) References Cited

U.S. PATENT DOCUMENTS

| | | | | | |
|---|---|---|---|---|---|
| 4,962,194 | A | * | 10/1990 | Bridges | 536/27.3 |
| 5,244,896 | A | * | 9/1993 | Borcherding et al. | 514/258 |
| 5,430,027 | A | * | 7/1995 | Knutsen et al. | 514/46 |
| 5,646,128 | A | * | 7/1997 | Firestein et al. | 514/46 |
| 6,492,348 | B1 | * | 12/2002 | Bays et al. | 514/46 |

FOREIGN PATENT DOCUMENTS

| | | | |
|---|---|---|---|
| GB | 9813554.4 | * | 6/1998 |
| WO | WO 94/17090 A1 | * | 8/1994 |
| WO | WO 95/03304 A1 | * | 2/1995 |
| WO | WO 98 01426 A | | 1/1998 |
| WO | WO 98 01459 A | | 1/1998 |
| WO | WO 98 16539 A | | 4/1998 |
| WO | WO 98 28319 A | | 7/1998 |
| WO | WO 99 38877 A2 | | 5/1999 |
| WO | WO 99 41267 A1 | | 10/1999 |

OTHER PUBLICATIONS

Baker et al., "5'–Substituted–5'–deoxy Nucleosides," *Tetrahedron*, 30, 2939–2942 (1974).*

Borcherding et al.(II), "Carbocyclic Nucleosides as Inhibitors of Human Tumor Necrosis Factor–α Production: Effects of the Stereoisomers of (3–Hydroxycyclopentyl)adenines," *Journal of Medicinal Chemistry*, 39(13), 2615–2620 (Jun. 21, 1996).*

* cited by examiner

*Primary Examiner*—James O. Wilson
*Assistant Examiner*—Lawrence E Crane
(74) *Attorney, Agent, or Firm*—Bacon & Thomas, PLLC

(57) ABSTRACT

A method of treating a patient suffering from or susceptible to ischemic heart disease, peripheral vascular disease or stroke or which subject is suffering pain, a CNS disorder or sleep apnea which comprises administering a therapeutically effective amount of an adenosine derivative which is an agonist at the adenosine A1 receptor and which exhibits little or no agonist activity of the A3 receptor. The adenosine derivative has a general formula (I) as follows:

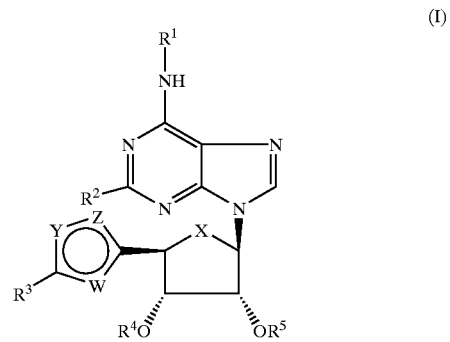

13 Claims, No Drawings

ADENOSINE DERIVATIVES AND METHODS OF ADMINISTRATION

This application is a continuation application of pending U.S. application Ser. No. 09/736,018, filed Dec. 19, 2000 (of which the entire disclosure of the pending, prior application is hereby incorporated by reference), which is a 371 of PCT/EP99/04182, filed Jun. 21, 1999 and which has issued as U.S. Pat. No. 6,492,348 on Dec. 10, 2002.

The present invention relates to novel adenosine derivatives, to processes for their preparation, to pharmaceutical compositions containing them and to their use in medicine.

Publications in this area include WO 98/16539 (Novo Nordisk A/S) which describes adenosine derivatives for the treatment of myocardial and cerebral ischaemia and epilepsy; WO 98/04126 (Rhone-Poulenc Rorer Pharmaceuticals Inc.) which relates to adenosine derivatives possessing antihypertensive, cardioprotective, anti-ischaemic and antilipolytic properties; and WO 98/01459 (Novo Nordisk A/S) which describes N,9-disubstituted adenine derivatives which are substituted in the 4' position by unsubstituted oxazolyl or isoxazolyl and the use of such compounds for the treatment of disorders involving cytokines in humans.

Thus the invention provides a compound of formula (1) which is an agonist at the adenosine A1 receptor

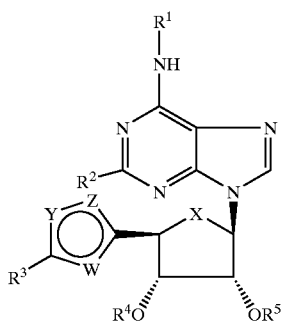

(I)

wherein

X represents O or $CH_2$;

$R^2$ represents $C_{1-3}$alkyl, $C_{1-3}$alkoxy, halogen or hydrogen;

$R^3$ represents H, phenyl (optionally substituted by halogen), a 5 or 6 membered heteroaryl group, $C_{1-6}$ alkoxy, $C_{1-6}$ alkylO$(CH_2)_n$ where n is 0–6, $C_{3-7}$ cycloalkyl, $C_{1-6}$ hydroxyalkyl, halogen or a $C_{1-6}$ straight or branched alkyl, $C_{1-6}$ alkenyl or $C_{1-6}$ alkynyl group optionally substituted by one or more halogens.

Y and Z represent O, N, CH, N($C_{1-6}$ alkyl)

W represents CH, O, N, S, N($C_{1-6}$ alkyl)

and wherein at least one of W and Z represents a heteroatom (and when Y, Z and/or W is N, the presence or absence of an additional H would be apparent to a person skilled in the art)

with the proviso that when W represents CH, Z represents N and Y represents O, $R^3$ cannot be H.

$R^4$ and $R^5$ independently represent H or a $C_{1-16}$ straight chain or branched alkyl group.

$R^1$ represents hydrogen or a group selected from (1) -(alk)$_n$-($C_{3-7}$) cycloalkyl, including bridged cycloalkyl, said cycloalkyl group optionally substituted by one or more substituents selected from OH, halogen, —($C_{1-3}$) alkoxy, wherein (alk) represents $C_{1-3}$ alkylene and n represents 0 or 1.

(2) an aliphatic heterocyclic group of 4 to 6 membered rings containing at least one heteroatom selected from O, N or S, optionally substituted by one or more substituents selected from the group consisting of —($C_{1-3}$)alkyl, —$CO_2$—($C_{1-4}$)alkyl, —CO($C_{1-3}$alkyl), —S(=O)$_n$— ($C_{1-3}$ alkyl), —CONR$^a$R$^b$ (wherein R$^a$ and R$^b$ independently represent H or $C_{1-3}$alkyl) or =O; where there is a sulfur atom in the heterocyclic ring, said sulfur is optionally substituted by (=O)$_n$, where n is 1 or 2.

(3) Straight or branched $C_{1-12}$ alkyl, optionally including one or more O, S(=O)$_n$ (where n is 0, 1 or 2) and N groups substituted within the alkyl chain, said alkyl optionally substituted by one or more of the following groups, phenyl, halogen, hydroxy, $C_{3-7}$ cycloalkyl or NR$^a$R$^b$ wherein R$^a$ and R$^b$ independently represent hydrogen, $C_{3-7}$ cycloalkyl or a $C_{1-6}$ straight chain or branched alkyl optionally substituted by $C_{3-7}$ cycloalkyl;

(4) a fused bicyclic aromatic ring

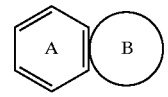

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —$CO_2$—($C_{1-13}$alkyl).

(5) a phenyl group optionally substituted by one or more substituents selected from:

-halogen, —$SO_3H$, -(alk)$_n$OH, -(alk)$_n$-cyano, —(O)$_n$— ($C_{1-6}$)alkyl (optionally substituted by one or more halogens), -(alk)$_n$-nitro, —(O)$_m$-(alk)$_n$-$CO_2$R$^c$, -(alk$_n$)-CONR$^c$R$^d$-(alk)$_n$-COR$^c$,- (alk)$_n$-SOR$^e$, -(alk)$_n$-$SO_2$R$^e$, (alk)$_n$-$SO_2$NR$^c$R$^d$, -(alk)$_n$OR$^c$, -(alk)$_n$-(CO)$_m$-NHSO$_2$R$^e$, -(alk)$_n$-NHCOR$^c$, -(alk)$_n$-NR$^c$R$^d$ wherein m and n are 0 or 1 and alk represents a $C_{1-6}$alkylene group or $C_{2-6}$ alkenyl group.

(6) A phenyl group substituted by a 5 or 6 membered heterocyclic aromatic group, said heterocyclic aromatic group optionally being substituted by $C_{1-3}$alkyl or NR$^c$R$^d$.

R$^c$ and R$^d$ may each independently represent hydrogen, or $C_{1-3}$ alkyl or when part of a group NR$^c$R$^d$, R$^c$ and R$^d$ together with the nitrogen atom may form a 5 or 6 membered heterocyclic ring optionally containing other heteroatoms, which heterocyclic ring may optionally be substituted further by one or more $C_{1-3}$ alkyl groups.

R$^e$ represents $C_{1-3}$alkyl and salts and solvates thereof, in particular, physiologically acceptable solvates and salts thereof for use in therapy.

Preferably the compound is of formula (Ia)

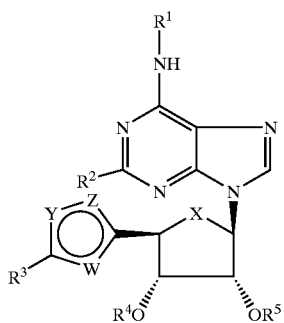

(Ia)

wherein
X represents O or $CH_2$;
$R^2$ represents $C_{1-3}$alkyl, $C_{1-3}$alkoxy, halogen or hydrogen;
$R^3$ represents H, phenyl (optionally substituted by halogen), a 5 or 6 membered heteroaryl group, $C_{1-6}$ alkoxy, $C_{1-6}$ straight or branched alkyl optionally substituted by one or more halogens, $C_{3-7}$ cycloalkyl, $C_{1-6}$ hydroxyalkyl or halogen.
Y and Z represent O, N, CH
W represents CH, O, N, S
and wherein at least one of W and Z represents a heteroatom (and when Y, Z and/or W is N, the presence or absence of an additional H would be apparent to a person skilled in the art)
with the proviso that when W represents CH, Z represents N and Y represents O, $R^3$ cannot be H.
$R^4$ and $R^5$ independently represent H or a $C_{1-6}$ straight chain or branched alkyl group.
$R^1$ represents a group selected from
(1) -(alk)$_n$-(C$_{3-7}$) cycloalkyl, including bridged cycloalkyl, said cycloalkyl group optionally substituted by one or more substituents selected from OH, halogen, —(C$_{1-3}$)alkoxy, wherein (alk) represents $C_{1-3}$ alkylene and n represents 0 or 1.
(2) an aliphatic heterocyclic group of 4 to 6 membered rings containing at least one heteroatom selected from O, N or S, optionally substituted by one or more substituents selected from the group consisting of —(C$_{1-3}$)alkyl, —CO$_2$—(C$_{1-4}$)alkyl, —CO(C$_{1-3}$alkyl), —S(=O)$_n$—(C$_{1-3}$alkyl), —CONR$^a$R$^b$ (wherein R$^a$ and R$^b$ independently represent H or C$_{1-3}$alkyl) or =O; where there is a sulfur atom in the heterocyclic ring, said sulfur is optionally substituted by (=O)$_n$, where n is 1 or 2.
(3) Straight or branched C$_{1-12}$ alkyl, optionally including one or more O, S(=O)$_n$ (where n is 0, 1 or 2) and N groups substituted within the alkyl chain, said alkyl optionally substituted by one or more of the following groups, phenyl, halogen, hydroxy, C$_{3-7}$ cycloalkyl or NR$^a$R$^b$ wherein R$^a$ and R$^b$ independently represent hydrogen, C$_{3-7}$ cycloalkyl or a C$_{1-6}$ straight chain or branched alkyl optionally substituted by C$_{3-7}$ cycloalkyl;
(4) a fused bicyclic aromatic ring

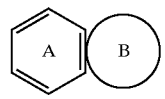

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —CO$_2$—(C$_{1-3}$alkyl).
(5) a phenyl group optionally substituted by one or more substituents selected from:
-halogen, —SO$_3$H, -(alk)$_n$OH, -(alk)$_n$-cyano, —(O)$_n$—(C$_{1-6}$)alkyl (optionally substituted by one or more halogens), -(alk)$_n$-nitro, -(O)$_m$-(alk)$_n$-CO$_2$R$^c$, -(alk$_n$)-CONR$^c$R$^d$-(alk)$_n$-COR$^c$, -(alk)$_n$-SOR$^e$, -(alk)$_n$-SO$_2$R$^e$, -(alk)$_n$-SO$_2$NR$^c$R$^d$, -(alk)$_n$OR$^c$, -(alk)$_n$-(CO)$_m$—NHSO$_2$R$^e$, -(alk)$_n$-NHCOR$^c$, -(alk)$_n$-NR$^c$R$^d$ wherein m and n are 0 or 1 and alk represents a C$_{1-6}$alkylene group or C$_{2-6}$ alkenyl group.
(6) A phenyl group substituted by a 5 or 6 membered heterocyclic aromatic group, said heterocyclic aromatic group optionally being substituted by C$_{1-3}$alkyl or NR$^c$R$^d$.
R$^c$ and R$^d$ may each independently represent hydrogen, or C$_{1-3}$ alkyl or when part of a group NR$^c$R$^d$, R$^c$ and R$^d$ together with the nitrogen atom may form a 5 or 6 membered heterocyclic ring optionally containing other heteroatoms, which heterocyclic ring may optionally be substituted further by one or more C$_{1-3}$ alkyl groups.
R$^e$ represents C$_{1-3}$alkyl
and salts and solvates thereof, in particular, physiologically acceptable solvates and salts thereof.

The invention further provides pharmaceutical compositions of formula (I) or (Ia) together with a pharmaceutically acceptable diluent or carrier.

It will be appreciated that certain compounds embraced by formula (I) are novel per se. A particular group of compounds may be defined by formula (Ib). Therefore, the invention further provides compounds of formula (Ib) which are agonists at the adenosine A1 receptor

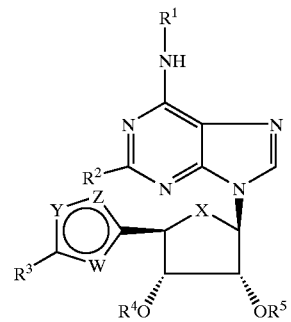

(Ib)

wherein
X represents O or CH$_2$.
$R^2$ represents C$_{1-3}$alkyl, C$_{1-3}$alkoxy, halogen or hydrogen;
$R^3$ represents H, phenyl (optionally substituted by halogen), a 5 or 6 membered heteroaryl group, C$_{1-6}$ alkoxy, C$_{1-6}$alkylO(CH$_2$)$_n$ where n is 0–6, C$_{3-7}$ cycloalkyl, C$_{1-6}$ hydroxyalkyl, halogen or a C$_{1-6}$ straight or branched alkyl, C$_{1-6}$ alkenyl or C$_{1-6}$ alkynyl group optionally substituted by one or more halogens.
Y and Z represent O, N, CH, N(C$_{1-6}$ alkyl)
W represents CH, O, N, S, N(C$_{1-6}$ alkyl)
and wherein at least one of W and Z represents a heteroatom (and when Y, Z and/or W is N, the presence or absence of an additional H would be apparent to a person skilled in the art)
with the proviso that when W represents CH, Z represents N and Y represents O, R$^3$ cannot be H.

$R^4$ and $R^5$ independently represent H or a $C_{1-6}$ straight chain or branched alkyl group.

$R^1$ represents hydrogen or a group selected from (1) -(alk)$_n$-(C$_{3-7}$) cycloalkyl, including bridged cycloalkyl, said cycloalkyl group optionally substituted by one or more substituents selected from OH, halogen, —(C$_{1-3}$) alkoxy, wherein (alk) represents C$_{1-3}$ alkylene and n represents 0 or 1.

(2) an aliphatic heterocyclic group of 4 to 6 membered rings containing at least one heteroatom selected from O, N or S, optionally substituted by one or more substituents selected from the group consisting of —(C$_{1-3}$)alkyl, —CO$_2$—(C$_{1-4}$)alkyl, —CO(C$_{1-3}$alkyl), —S(=O)$_n$—(C$_{1-3}$alkyl), —CONR$^a$R$^b$ (wherein R$^a$ and R$^b$ independently represent H or C$_{1-3}$alkyl) or =O; where there is a sulfur atom in the heterocyclic ring, said sulfur is optionally substituted by (=O)$_n$, where n is 1 or 2.

(3) Straight or branched C$_{1-2}$ alkyl, optionally including one or more O, S(=O)$_n$ (where n is 0, 1 or 2) and N groups substituted within the alkyl chain, said alkyl optionally substituted by one or more of the following groups, phenyl, halogen, hydroxy, C$_{3-7}$ cycloalkyl or NR$^a$R$^b$ wherein R$^a$ and R$^b$ independently represent hydrogen, C$_{3-7}$ cycloalkyl or a C$_{1-6}$ straight chain or branched alkyl optionally substituted by C$_{3-7}$ cycloalkyl;

(4) a fused bicyclic aromatic ring

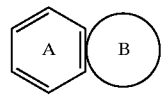

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —CO$_2$—(C$_{1-3}$alkyl).

(5) a phenyl group optionally substituted by one or more substituents selected from:

-halogen, —SO$_3$H, -(alk)$_n$OH, -(alk)$_n$-cyano, —(O)$_n$—(C$_{1-6}$)alkyl (optionally substituted by one or more halogens), -(alk)$_n$-nitro, —(O)$_m$-(alk)$_n$-CO$_2$R$^c$, -(alk$_n$)-CONR$^c$R$^d$-(alk)$_n$-COR$^c$, -(alk)$_n$-SOR$^e$, -(alk)$_n$-SO$_2$R$^e$, -(alk)$_n$-SO$_2$NR$^c$R$^d$, -(alk)$_n$OR$^c$, -(alk)$_n$-(CO)$_m$—NHSO$_2$R$^e$, -(alk)$_n$-NHCOR$^c$, -(alk)$_n$-NR$^c$R$^d$ wherein m and n are 0 or 1 and alk represents a C$_{1-6}$alkylene group or C$_{2-6}$ alkenyl group.

(6) A phenyl group substituted by a 5 or 6 membered heterocyclic aromatic group, said heterocyclic aromatic group optionally being substituted by C$_{1-3}$alkyl or NR$^c$R$^d$.

R$^c$ and R$^d$ may each independently represent hydrogen, or C$_{1-3}$ alkyl or when part of a group NR$^c$R$^d$, R$^c$ and R$^d$ together with the nitrogen atom may form a 5 or 6 membered heterocyclic ring optionally containing other heteroatoms, which heterocyclic ring may optionally be substituted further by one or more C$_{1-3}$ alkyl groups.

R$^e$ represents C$_{1-3}$alkyl with the proviso that when R$^4$ and R$^5$ both represent H, R$^2$ represents halogen, R$^3$ cannot represent methyl, ethyl, n-propyl, isopropyl, cyclopropyl, CH(OH)CH$_3$, C$_{1-3}$alkoxy and salts and solvates thereof, in particular, physiologically acceptable solvates and salts thereof.

Preferably, the compound is of formula (Ic):

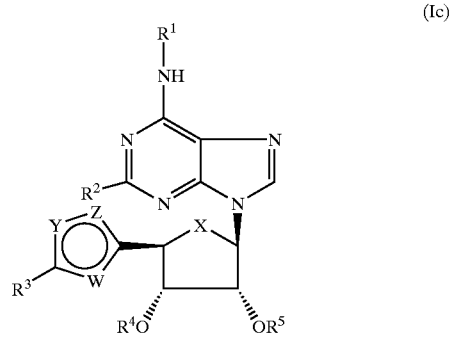

(Ic)

wherein X represents O or CH$_2$;

R$^2$ represents C$_{1-3}$alkyl, C$_{1-3}$alkoxy, halogen or hydrogen;

R$^3$ represents H, phenyl (optionally substituted by halogen), a 5 or 6 membered heteroaryl group, C$_{1-6}$ alkoxy, C$_{1-6}$ straight or branched alkyl optionally substituted by one or more halogens, C$_{3-7}$ cycloalkyl, C$_{1-6}$ hydroxyalkyl or halogen.

Y and Z represent O, N, CH

W represents CH, O, N, S and wherein at least one of W and Z represents a heteroatom (and when Y, Z and/or W is N, the presence or absence of an additional H would be apparent to a person skilled in the art)

with the proviso that when W represents CH, Z represents N and Y represents O, R$^3$ cannot be H.

R$^4$ and R$^5$ independently represent H or a C$_{1-6}$ straight chain or branched alkyl group.

R$^1$ represents a group selected from (1) -(alk)$_n$-(C$_{3-7}$) cycloalkyl, including bridged cycloalkyl, said cycloalkyl group optionally substituted by one or more substituents selected from OH, halogen, —(C$_{1-3}$) alkoxy, wherein (alk) represents C$_{1-3}$ alkylene and n represents 0 or 1.

(2) an aliphatic heterocyclic group of 4 to 6 membered rings containing at least one heteroatom selected from O, N or S, optionally substituted by one or more substituents selected from the group consisting of —(C$_{1-3}$)alkyl, —CO$_2$—(C$_{1-4}$)alkyl, —CO(C$_{1-3}$alkyl), —S(=O)$_n$—(C$_{1-3}$alkyl), —CONR$^a$R$^b$ (wherein R$^a$ and R$^b$ independently represent H or C$_{1-3}$alkyl) or =O; where there is a sulfur atom in the heterocyclic ring, said sulfur is optionally substituted by (=O)$_n$, where n is 1 or 2.

(3) Straight or branched C$_{1-12}$ alkyl, optionally including one or more O, S(=O)$_n$ (where n is 0, 1 or 2) and N groups substituted within the alkyl chain, said alkyl optionally substituted by one or more of the following groups, phenyl, halogen, hydroxy, C$_{3-7}$ cycloalkyl or NR$^a$R$^b$ wherein R$^a$ and R$^b$ independently represent hydrogen, C$_{3-7}$ cycloalkyl or a C$_{1-6}$ straight chain or branched alkyl optionally substituted by C$_{3-7}$ cycloalkyl;

(4) a fused bicyclic aromatic ring

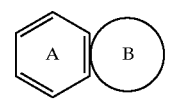

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —$CO_2$—($C_{1-3}$alkyl).

(5) a phenyl group optionally substituted by one or more substituents selected from:
-halogen, —$SO_3H$, -(alk)$_n$OH, -(alk)$_n$-cyano, —(O)$_n$—($C_{1-6}$)alkyl (optionally substituted by one or more halogens), -(alk)$_n$-nitro, —(O)$_m$-(alk)$_n$-$CO_2R^c$, -(alk$_n$)-$CONR^cR^d$-(alk)$_n$-$COR^c$, -(alk)$_n$-$SOR^e$, -(alk)$_n$-$SO_2R^e$, -(alk)$_n$-$SO_2NR^cR^d$, -(alk)$_n$$OR^c$, -(alk)$_n$-$(CO)_m$—$NHSO_2R^e$, -(alk)$_n$-$NHCOR^c$, -(alk)$_n$-$NR^{Rd}$ wherein m and n are 0 or 1 and alk represents a $C_{1-6}$alkylene group or $C_{2-6}$ alkenyl group.

(6) A phenyl group substituted by a 5 or 6 membered heterocyclic aromatic group, said heterocyclic aromatic group optionally being substituted by $C_{1-3}$alkyl or $NR^cR^d$.
$R^c$ and $R^d$ may each independently represent hydrogen, or $C_{1-3}$ alkyl or when part of a group $NR^cR^d$, $R^c$ and $R^d$ together with the nitrogen atom may form a 5 or 6 membered heterocyclic ring optionally containing other heteroatoms, which heterocyclic ring may optionally be substituted further by one or more $C_{1-3}$ alkyl groups.

$R^e$ represents $C_{1-3}$alkyl
with the proviso that when $R^4$ and $R^5$ both represent H, $R^2$ represents halogen, $R^3$ cannot represent methyl, ethyl, n-propyl, isopropyl, cyclopropyl, $CH(OH)CH_3$, $C_{1-3}$alkoxy
and salts and solvates thereof, in particular, physiologically acceptable solvates and salts thereof.

Conveniently the adenosine A1 agonists of the general formula (I) above exhibit greater activity at the adenosine A1 receptor than the other adenosine receptor subtypes, particularly A3. More particularly the compounds exhibit little or no agonist activity at the the A3 receptor.

It will be appreciated that wherein $R^1$ and/or $R^2$ in compounds of formula (I) contain one or more asymmetric carbon atoms the invention includes all diastereoisomers of compounds of formula (I) and mixtures thereof. Otherwise the stereochemical configuration of compounds of the invention is as depicted in formula (I) above.

As used herein, the term "alkyl" means a straight or branched chain alkyl group. Examples of suitable alkyl groups within $R^1$ and $R^2$ include methyl, ethyl, n-propyl, 1-propyl, n-butyl, s-butyl, t-butyl and 2,2-dimethylpropyl.

As used herein, the term "alkylene" means a straight or branched chain alkylene group containing 1–6 carbon atoms, e.g. methylene.

As used herein, the term "$C_{2-6}$alkenyl" means a straight or branched chain alkenyl group containing 2 to 6 carbon atoms. Allyl represents an example of a suitable $C_{2-6}$alkenyl group.

The term "halogen" means fluorine, chlorine, bromine or iodine.

By aliphatic heterocyclic group defined for $R^1$ is meant a cyclic group of 4–6 carbon atoms wherein one or more of the carbon atoms is/are replaced by heteroatoms independently selected from nitrogen, oxygen or sulfur. This group may optionally be substituted as defined hereinabove.

The term heterocyclic aromatic group defined for $R^1$ refers to an aromatic mono or bicyclic ring system comprising from 5 to 10 carbon atoms wherein one or more of the carbon atoms is/are replaced by heteroatoms independently selected from nitrogen, oxygen and sulfur, which ring system may optionally be substituted as defined hereinabove.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. A particularly suitable pharmaceutically acceptable salt of the compounds of formula (I) is the hydrochloride salt. Other acids such as oxalic, while not, in themselves pharmaceutically acceptable, may be useful as intermediates in obtaining the compounds of the invention and their pharmaceutically acceptable acid addition salts. The solvates may be, for example, hydrates.

Examples of W, Y and Z containing heterocyclic groups include isoxazoles, oxadiazoles, pyrazoles, oxazoles, triazoles and thiadiazoles.

Preferred W, Y and Z containing heterocyclic groups are isoxazoles, and 1,2,4 - and 1,3,4-oxadiazoles.

$R^2$ preferably represents hydrogen, methyl, methoxy or halogen, more preferably hydrogen or chlorine.

Conveniently, $R^1$ may represent (alk)$_n$-$C_{3-6}$ cycloalkyl wherein n is 0 or 1 and the said cycloalkyl is either substituted by at least one substituent selected from halogen, particularly fluorine, and OH or is unsubstituted. Preferably n is zero. More preferably, the cycloalkyl group is unsubstituted or monosubstituted with OH and more preferably the cycloalkyl ring has 5 carbon members. Most preferably, the cycloalkyl group is hydroxycyclopentyl.

Alternatively $R^1$ may represent a substituted or unsubstituted aliphatic heterocyclic group, the substitutent being selected from the group consisting of —$CO_2$—($C_{1-4}$)alkyl.

Conveniently, the aliphatic heterocyclic group is unsubstituted or when the substituent is —$CO_2(C_{1-4})$alkyl, the heteroatom is N and the substituent is directly attached to said ring nitrogen atom.

Preferably the heterocyclic ring is 6 membered and more preferably contains only one O, N or S heteroatom. Most preferably when the heterocyclic ring is unsubstituted the heteroatom is O. Most preferably when the heterocyclic ring is substituted the heteroatom is N.

Alternatively, $R^1$ may represent a straight or branched alkyl of 1–6 carbon atoms optionally with at least one $S(\!=\!O)_n$ and where $S(\!=\!O)_n$ is present, optionally substituted with N at a position adjacent to the $S(\!=\!O)_n$ group; where there is an $S(\!=\!O)_n$ in the chain, substitution with N at a position adjacent to the $S(\!=\!O)_n$ group is preferred; where there is an $S(\!=\!O)_n$ in the chain, preferably n is 1 or 2, more preferably n is 2. The alkyl group conveniently may be unsubstituted or substituted by at least one OH group.

Alternatively $R^1$ may represent a phenyl group which is substituted by one or two substituents selected from OH, alkyl, particularly $C_{1-4}$ alkyl and halogen. Preferably the phenyl is disubstituted in the 2,4 positions. Preferably both substituents are halogen more particularly, fluorine and chlorine. For example, a particularly preferred combination is 2-fluoro and 4-chloro.

Preferably $R^4$ and $R^5$ represent hydrogen.

It is to be understood that the present invention covers all combinations of particular and preferred groups mentioned above.

Particular novel compounds include compounds of Examples 1–207 herein below.

Preferred compounds include:
(2S,3 S,4 R,5R)-2-(5-tert-Butyl-[1,3,4]oxadiazol-2-yl)-5-[6-(tetrahydro-pyran-4-ylamino)-purin-9-yl]-tetrahydro-furan-3,4-diol;
4-{9-[5S-(5-tert-Butyl-[1,3,4]oxadiazol-2-yl)-3R,4S-dihydroxy-tetrahydro-furan-2R-yl]-9H-purin-6-ylamino}-piperidine-1-carboxylic acid ethyl ester;

(2S,3S,4R,5R)-2-(5-Isopropyl-[1,3,4]oxadiazol-2-yl)-5-[6-(tetrahydro-pyran-4-ylamino)-purin-9-yl]-tetrahydro-furan-3,4-diol;

4-{9-[5S-(5-Cyclopropyl-[1,3,4]oxadiazol-2-yl)-3R,4S-dihydroxy-tetrahydro-furan-2R-yl]-9H-purin-6-ylamino}-piperidine-1-carboxylic acid ethyl ester;

(2S,3S,4R,5R)-2-(5-tert-Butyl-[1,3,4]oxadiazol-2-yl)-5-[6-(4-chloro-2-fluoro-phenylamino)-purin-9-yl]-tetrahydro-furan-3,4-diol;

(2S,3S,4R,5R)-2-(5-Ethyl-oxazol-2-yl)-5-[6-(tetrahydro-pyran-4-ylamino)-purin yl]-tetrahydro-furan-3,4-diol;

(2S,3S,4R,5R)-2-(3-Cyclopropyl-[1,2,4]oxadiazol-5-yl)-5-[6-(2S-hydroxy-cyclopent-(S)-ylamino)-purin-9-yl]-tetrahydro-furan-3,4-diol;

(2S,3S,4R,5R)-2-(3-tert-Butyl-[1,2,4]oxadiazol-5-yl)-5-[6-(2S-hydroxy-cyclopent-(S)-ylamino)-purin-9-yl]-tetrahydro-furan-3,4-diol;

(2S,3S,4 R,5R)-2-(3-Cyclopropyl-[1,2,4]oxadiazol-5-yl)-5-[6-(tetrahydro-pyran4-ylamino)-purin-9-yl]-tetrahydro-furan-3,4-diol;

(2S,3S,4R,5R)-2-(3-tert-Butyl-isoxazol-5-yl)-5-[6-(tetrahydro-pyran4-ylamino)-purin-9-yl]-tetrahydro-furan-3,4-diol;

ethyl 4-({9-[(2R,3R,4S,5S)-3,4-dihydroxy-5-(3-methyl-1,2,4-oxadiazol-5-yl)tetrahydrofuran-2-yl]-9H-purin-6-yl}amino)piperidine-1-carboxylate;

(2S,3S,4 R,5R)-2-[3-(tert-butyl)-1,2,4-oxadiazol-5-yl]-5-{6-[(cyclopropylmethyl)amino]-9H-purin-9-yl}tetrahydrofuran-3,4-diol;

(2S,3S,4R,5R)-2-[3-(tert-butyl)-1,2,4-oxadiazol-5-yl]-5-[6-(isobutylamino)-9H-purin-9-yl]tetrahydrofuran-3,4-diol;

(2R,3R,4S,5S)-2-[6-(cyclopropylamino)-9H-purin-9-yl]-5-(3-isopropyl-1,2,4-oxadiazol-5-yl)tetrahydrofuran-3,4-diol;

2-({9-[(2R,3R,4S,5S)-3,4-dihydroxy-5-(3-isopropyl-1,2,4-oxadiazol-5-yl)tetrahydrofuran-2-yl]-9H-purin-6-yl}amino)-N-methylethanesulfonamide;

(2R,3R,4S,5S)-2-[6-(3,4-difluoroanilino)-9H-purin-9-yl]-5-(3-isopropyl-1,2,4-oxadiazol-5-yl)tetrahydrofuran-3,4-diol;

(2R,3R,4S,5S)-2-[6-(4-chloro-2-fluoroanilino)-9H-purin-9-yl]-5-(3-cyclopropyl-1,2,4-oxadiazol-5-yl)tetrahydrofuran-3,4-diol;

(2R,3S,4 R,5 R)-2-[5-(tert-butyl)-4H-1,2,4-triazol-3-yl]-5-[6-(4-chloro-2-fluoroanilino)-9H-purin-9-yl]tetrahydrofuran-3,4-diol;

(2R,3R,4S,5R)-2-[6-(2-chloro-4-fluoroanilino)-9H-purin-9-yl]-5-(5-isopropyl-4H-1,2,4-triazol-3-yl)tetrahydrofuran-3,4-diol;

(2S,3S,4R,5R)-2-(5-cyclopropyl-1,3,4-oxadiazol-2-yl)-5-[6-(tetrahydro-2H-pyran-4-ylamino)-9H-purin-9-yl]tetrahydrofuran-3,4-diol;

(2S,3S,4R,5R)-2-[5-(tert-butyl)-1,3,4-oxadiazol-2-yl]-5-[6-(2-chloro-4-fluoroanilino)-9H-purin-9-yl]tetrahydrofuran-3,4-diol;

(2S,3S,4 R,5R)-2-[3-(tert-butyl)isoxazol-5-yl]-5-{6-[(1,1-dioxidotetrahydro-2H-thiopyran-4-yl)amino]-9H-purin-9-yl}tetrahydrofuran-3,4-diol;

2-[(9-{(2R,3 R,4S,5S)-5-[5-(tert-butyl)-1,3,4-oxadiazol-2-yl]-3,4-dihydroxytetrahydrofuran-2-yl}-9H-purin-6-yl)amino]-N-ethylethanesulfonamide;

2-[(9-{(2R,3R,4S,5S)-5-[5-(tert-butyl)-1,3,4-oxadiazol-2-yl]-3,4-dihydroxytetrahydrofuran-2-yl}-9H-purin-6-yl)amino]-N-(3-methylphenyl)ethanesulfonamide;

2-({9-[(2R,3R,4S,5S)-3,4-dihydroxy-5-(5-methyl-1,3-oxazol-2-yl)tetrahydrofuran-2-yl]-9H-purin-6-yl}amino)-N-methylethanesulfonamide;

(2R,3R,4S,5S)-2-[6-(cyclopentylamino)-9H-purin-9-yl]-5-[3-(methoxymethyl)-1,2,4-oxadiazol-5-yl]tetrahydrofuran-3,4-diol;

(2S,3S,4R,5R)-2-(5-ethyl-1,3,4-oxadiazol-2-yl)-5-[6-(isopropylamino)-9H-purin-9-yl]tetrahydrofuran-3,4-diol;

(2R,3R,4S,5S)-2-(6-{[(1 S,2S)-2-hydroxycyclopentyl]amino}-9H-purin-9-yl)-5-(5-methyl-1,3,4-oxadiazol-2-yl)tetrahydrofuran-3,4-diol;

(2R,3R,4S,5S)-2-{2-chloro-6-[(1-ethylpropyl)amino]-9H-purin-9-yl}-5-(3-cyclopropyl-1,2,4-oxadiazol-5-yl)tetrahydrofuran-3,4-diol formate (1:2);

(2R,3R,4S,5S)-2-[2-Chloro-6-(1-ethyl-propylamino)-purin-9-yl]-5-(3-cyclopropyl-[1,2,4]oxadiazol-5-yl)-tetrahydro-furan-3,4-diol diformate;

(2S,3S,4R,5R)-2-(3-ethylisoxazol-5-yl)-5-[6-(tetrahydro-2H-pyran-4-ylamino)-9H-purin-9-yl]tetrahydrofuran-3,4-diol;

(2S,3S,4R,5R)-2-(3-ethylisoxazol-5-yl)-5-(6-{[(1S,2S)-2-hydroxycyclopentyl]amino}-9H-purin-9-yl)tetrahydrofuran-3,4-diol;

ethyl 4-({9-[(2R,3R,4S,5S)-5-(3-ethylisoxazol-5-yl)-3,4-dihydroxytetrahydrofuran-2-yl]-9H-purin-6-yl}amino)piperidine-1-carboxylate;

(2R,3S,4R,5R)-2-[5-(tert-butyl)-4H-1,2,4-triazol-3-yl]-5-[6-(tetrahydro-2H-pyran-4-ylamino)-9H-purin-9-yl]tetrahydrofuran-3,4-diol;

(2R,3S,4R,5R)-2-(5-isopropyl-4H-1,2,4-triazol-3-yl)-5-[6-(tetrahydro-2H-pyran-4-ylamino)-9H-purin-9-yl]tetrahydrofuran-3,4-diol;

(2R,3R,4S,5S)-2-[2-chloro-6-(2-chloro-4-fluoroanilino)-9H-purin-9-yl]-5-(5-methyl-1,3-oxazol-2-yl)tetrahydrofuran-3,4-diol;

(2R,3R,4S,5S)-2-[6-(4-chloro-2-fluoroanilino)-9H-purin-9-yl]-5-(3-methylisoxazol-5-yl)tetrahydrofuran-3,4-diol;

(2R,3R,4S,5S)-2-[6-(4-chloro-2-fluoroanilino)-9H-purin-9-yl]-5-(3-propylisoxazol-5-yl)tetrahydrofuran-3,4-diol;

(2R,3R,4S,5S)-2-[2-chloro-6-(tetrahydro-2H-pyran-4-ylamino)-9H-purin-9-yl]-5-(3-ethylisoxazol-5-yl)tetrahydrofuran-3,4-diol;

ethyl 4-({2-chloro-9-[(2R,3R,4S,5S)-5-(3-ethylisoxazol-5-yl)-3,4-dihydroxytetrahydrofuran-2-yl]-9H-purin-6-yl}amino)piperidine-1-carboxylate;

(2R,3R,4S,5S)-2-(2-chloro-6-{[(1S,2S)-2-hydroxycyclopentyl]amino}-9H-purin-9-yl)-5-(3-ethylisoxazol-5-yl)tetrahydrofuran-3,4-diol;

(2R,3R,4S,5S)-2-(2-chloro-6-{[2-(ethylsulfonyl)ethyl]amino}-9H-purin-9-yl)-5-(3-ethylisoxazol-5-yl)tetrahydrofuran-3,4-diol;

(2R,3R,4S,5S)-2-[2-chloro-6-(4-chloro-2-fluoroanilino)-9H-purin-9-yl]-5-(3-ethylisoxazol-5-yl)tetrahydrofuran-3,4-diol;

(2R,3R,4S,5S)-2-[2-chloro-6-(2-chloro-4-fluoroanilino)-9H-purin-9-yl]-5-(3-ethyl isoxazol-5-yl)tetrahydrofuran-3,4-diol;

(2R,3R,4S,5S)-2-[2-chloro-6-(2-fluoroanilino)-9H-purin-9-yl]-5-(3-ethylisoxazo-5-yl)tetrahydrofuran-3,4-diol;

(2R,3R,4S,5S)-2-[2-chloro-6-(2-chloroanilino)-9H-purin-9-yl]-5-(3-ethylisoxazol-5-yl)tetrahydrofuran-3,4-diol;

(2R,3R,4S,5S)-2-(6-{[(1S,2S)-2-hydroxycyclopentyl]amino}-9H-purin-9-yl)-5-[3-(hydroxymethyl)isoxazol-5-yl]tetrahydrofuran-3,4-diol;

ethyl 4-[(9-{(2R,3R,4S,5S)-3,4-dihydroxy-5-[3-(hydroxymethyl)isoxazol-5-yl]tetrahydrofuran-2-yl}-9H-purin-6-yl)amino]piperidine-1-carboxylate;

(2S,3S,4R,5R)-2-[3-(hydroxymethyl)isoxazol-5-yl]-5-[6-(tetrahydro-2H-pyran-4-ylamino)-9H-purin-9-yl]tetrahydrofuran-3,4-diol;

(2R,3R,4S,5S)-2-[6-(4-chloro-2-fluoroanilino)-9H-purin-9-yl]-5-(3-ethylisoxazol-5-yl)tetrahydrofuran-3,4-diol;

(2R,3R,4S,5S)-2-[6-(2-chloro-4-fluoroanilino)-9H-purin-9-yl]-5-(3-ethylisoxazol-5-yl)tetrahydrofuran-3,4-diol;

(2S,3S,4R,5R)-2-(3-ethylisoxazol-5-yl)-5-[6-(2-fluoroanilino)-9H-purin-9-yl]tetrahydrofuran-3,4-diol;

(2R,3R,4S,5S)-2-[6-(2-chloroanilino)-9H-purin-9-yl]-5-(3-ethylisoxazol-5-yl)tetrahydrofuran-3,4-diol;

(2S,3S,4R,5R)-2-[5-(tert-butyl)-1,3,4-oxadiazol-2-yl]-5-[6-(piperidin-4-ylamino)-9H-purin-9-yl]tetrahydrofuran-3,4-diol;

(2R,3R,4S,5R)-2-{2-chloro-6-[(1-ethylpropyl)amino]-9H-purin-9-yl}-5-(5-ethylisoxazol-3-yl)tetrahydrofuran-3,4-diol formate;

(2S,3S,4R,5R)-2-(3-bromoisoxazol-5-yl)-5-[6-(4-chloro-2-fluoroanilino)-9H-purin-9-yl]tetrahydrofuran-3,4-diol (2S,3S,4R,5R)-2-[3-(tert-butyl)isoxazol-5-yl]-5-(6-{[1-(methylsulfonyl)piperidin-4-yl]amino}-9H-purin-9-yl)tetrahydrofuran-3,4-diol (2S,3S,4R,5R)-2-[3-(tert-butyl)isoxazol-5-yl]-5-(6-{[1-(propylsulfonyl)piperidin-4-yl]amino}-9H-purin-9-yl)tetrahydrofuran-3,4-diol (2S,3S,4R,5R)-2-[3-(tert-butyl)isoxazol-5-yl]-5-(6-{[1-(isopropylsulfonyl)piperidin-4-yl]amino}-9H-purin-9-yl)tetrahydrofuran-3,4-diol (2S,3S,4R,5R)-2-[3-(tert-butyl)isoxazol-5-yl]-5-(6-{[1-(ethylsulfonyl)piperidin-4-yl]amino}-9H-purin-9-yl)tetrahydrofuran-3,4-diol (2S,3S,4R,5R)-2-[3-(tert-butyl)isoxazol-5-yl]-5-[2-chloro-6-(4-chloro-2-fluoroanilino)-9H-purin-9-yl]tetrahydrofuran-3,4-diol (2S,3S,4R,5R)-2-[3-(tert-butyl)isoxazol-5-yl]-5-[2-chloro-6-(2-chloro-4-fluoroanilino)-9H-purin-9-yl]tetrahydrofuran-3,4-diol 2-[(9-{(2R,3R,4S,5S)-5-[3-(tert-butyl)isoxazol-5-yl]-3,4-dihydroxytetrahydrofuran-2-yl}-2-chloro-9H-purin-6-yl)amino]-N-ethylethanesulfonamide 2-[(9-{(2R,3R,4S,5S)-5-[3-(tert-butyl)isoxazol-5-yl]-3,4-dihydroxytetrahydrofuran-2-yl}-2-chloro-9H-purin-6-yl)amino]-N-isopropylethanesulfonamide (2S,3S,4R,5R)-2-[3-(tert-butyl)isoxazol-5-yl]-5-[2-chloro-6-(tetrahydro-2H-pyran-4-ylamino)-9H-purin-9-yl]tetrahydrofuran-3,4-diol (2R,3R,4S,5S)-2-[6-(4-chloro-2-fluoroanilino)-9H-purin-9-yl]-5-(3-pyridin-3-ylisoxazol-5-yl)tetrahydrofuran-3,4-diol (2R,3R,4S,5S)-2-[6-(4-chloro-2-fluoroanilino)-9H-purin-9-yl]-5-[3-(4-hydroxybutyl)isoxazol-5-yl]tetrahydrofuran-3,4-diol 2-[(9-{(2R,3R,4S,5S)-5-[3-(tert-butyl)isoxazol-5-yl]-3,4-dihydroxytetrahydrofuran-2-yl}-9H-purin-6-yl)amino]-N-ethylethanesulfonamide (2R,3R,4S,5S)-2-[6-(cyclopentylamino)-9H-purin-9-yl]-5-[5-(trifluoromethyl)-1,3,4-oxadiazol-2-yl]tetrahydrofuran-3,4-diol (2R,3R,4S,5S)-2-(6-{[(1S,2S)-2-hydroxycyclopentyl]amino}-9H-purin-9-yl)-5-[5-(trifluoromethyl)-1,3,4-oxadiazol-2-yl]tetrahydrofuran-3,4-diol ethyl 4-[(9-{(2R,3R,4S,5S)-3,4-dihydroxy-5-[5-(trifluoromethyl)-1,3,4-oxadiazol-2-yl]tetrahydrofuran-2-yl}-9H-purin-6-yl)amino]piperidine-1-carboxylate (2R,3R,4S,5S)-2-[6-(4-chloro-2-fluoroanilino)-9H-purin-9-yl]-5-(5-methyl-1,3,4-oxadiazol-2-yl)tetrahydrofuran-3,4-diol (2R,3R,4S,5S)-2-[6-(4-chloro-2-fluoroanilino)-9H-purin-9-yl]-5-(3-cyclopropylisoxazol-5-yl)tetrahydrofuran-3,4-diol (2S,3S,4R,5R)-2-[3-(tert-butyl)isoxazol-5-yl]-5-{6-[(1-butyrylpiperidin-4-yl)amino]-9H-purin-9-yl}tetrahydrofuran-3,4-diol isopropyl 4-[(9-{(2R,3R,4S,5S)-5-[3-(tert-butyl)isoxazol-5-yl]-3,4-dihydroxytetrahydrofuran-2-yl}-9H-purin-6-yl)amino]piperidine-1-carboxylate (2S,3S,4R,5R)-2-[3-(tert-butyl)isoxazol-5-yl]-5-(6-{[1-(2,2,2-trifluoroacetyl)piperidin-4-yl]amino}-9H-purin-9-yl)tetrahydrofuran-3,4-diol methyl 4-[(9-{(2R,3R,4S,5S)-5-[3-(tert-butyl)isoxazol-5-yl]-3,4-dihydroxytetrahydrofuran-2-yl}-9H-purin-6-yl)amino]piperidine-1-carboxylate (2R,3R,4S,5S)-2-[6-(4-chloro-2-fluoroanilino)-9H-purin-9-yl]-5-[3-(hydroxymethyl)isoxazol-5-yl]tetrahydrofuran-3,4-diol (2R,3R,4S,5S)-2-[6-(2-chloro-4-fluoroanilino)-9H-purin-9-yl]-5-[3-(hydroxymethyl)isoxazol-5-yl]tetrahydrofuran-3,4-diol (2R,3R,4S,5S)-2-[6-(2-fluoroanilino)-9H-purin-9-yl]-5-[3-(hydroxymethyl)isoxazol-5-yl]tetrahydrofuran-3,4-diol (2R,3R,4S,5S)-2-[6-(2-chloroanilino)-9H-purin-9-yl]-5-[3-(hydroxymethyl)isoxazol-5-yl]tetrahydrofuran-3,4-diol (2R,3R,4S,5S)-2-(2-chloro-6-{[(1S,2S)-2-hydroxycyclopentyl]amino}-9H-purin-9-yl)-5-[3-(hydroxymethyl)isoxazol-5-yl]tetrahydrofuran-3,4-diol (2R,3R,4S,5S)-2-[2-chloro-6-(tetrahydro-2H-pyran-4-ylamino)-9H-purin-9-yl]-5-[3-(hydroxymethyl)isoxazol-5-yl]tetrahydrofuran-3,4-diol 2-[(2-chloro-9-{(2R,3R,4S,5S)-3,4-dihydroxy-5-[3-(hydroxymethyl)isoxazol-5-yl]tetrahydrofuran-2-yl}-9H-purin-6-yl)amino]-N-ethylethanesulfonamide ethyl 4-[(2-chloro-9-{(2R,3R,4S,5S)-3,4-dihydroxy-5-[3-(hydroxymethyl)isoxazol-5-yl]tetrahydrofuran-2-yl}-9H-purin-6-yl)amino]piperidine-1-carboxylate (2R,3R,4S,5S)-2-[2-chloro-6-(4-chloro-2-fluoroanilino)-9H-purin-9-yl]-5-[3-(hydroxymethyl)isoxazol-5-yl]tetrahydrofuran-3,4-diol (2R,3R,4S,5S)-2-[2-chloro-6-(2-chloro-4-fluoroanilino)-9H-purin-9-yl]-5-[3-(hydroxymethyl)isoxazol-5-yl]tetrahydrofuran-3,4-diol (2R,3R,4S,5S)-2-[2-chloro-6-(2-fluoroanilino)-9H-purin-9-yl]-5-[3-(hydroxymethyl)isoxazol-5-yl]tetrahydrofuran-3,4-diol (2S,3S,4R,5R)-2-(3-ethylisoxazol-5-yl)-5-[2-methoxy-6-(tetrahydro-2H-pyran-4-ylamino)-9H-purin-9-yl]tetrahydrofuran-3,4-diol ethyl 4-({9-[(2R,3R,4S,5S)-5-(3-ethylisoxazol-5-yl)-3,4-dihydroxytetrahydrofuran-2-yl]-2-methoxy-9H-purin-6-yl}amino)piperidine-1-carboxylate (2S,3S,4R,5R)-2-(3-ethylisoxazol-5-yl)-5-(6-{[(1S,2S)-2-hydroxycyclopentyl]amino}-2-methoxy-9H-purin-9-yl)tetrahydrofuran-3,4-diol (2S,3S,4R,5R)-2-(3-ethylisoxazol-5-yl)-5-(6-{[2-(ethylsulfonyl)ethyl]amino}-2-methoxy-9H-purin-9-yl)tetrahydrofuran-3,4-diol (2R,3R,4S,5S)-2-[6-(2-chloro-4-fluoroanilino)-2-methoxy-9H-purin-9-yl]-5-(3-ethyl isoxazol-5-yl)tetrahydrofuran-3,4-diol (2S,3S,4R,5R)-2-(3-ethylisoxazol-5-yl)-5-[6-(2-fluoroanilino)-2-methoxy-9H-purin-9-yl]tetrahydrofuran-3,4-diol (2R,3R,4S,5S)-2-[6-(4-chloro-2-fluoroanilino)-2-methoxy-9H-purin-9-yl]-5-(3 ethylisoxazol-5-yl)tetrahydrofuran-3,4-diol (2S,3S,4R,5R)-2-[3-(tert-butyl)-1,2,4-oxadiazol-5-yl]-5-[6-(cyclopropylamino)-9H-purin-9-yl]tetrahydrofuran-3,4-diol (2S,3S,4R,5R)-2-[5-(tert-butyl)-1,3,4-oxadiazol-2-yl]-5-[2-chloro-6-(4-chloro-2-fluoroanilino)-9H-purin-9-yl]tetrahydrofuran-3,4-diol (2R,3R,4S,5S)-2-[6-(4-chloro-2-fluoroanilino)-9H-purin-9-yl]-5-(5-isopropyl-1,3,4-oxadiazol-2-yl)tetrahydrofuran-3,4-diol.

Compounds according to the invention have applicability as inhibitors of lipolysis i.e. they decrease plasma free fatty acid concentrations. The compounds may thus be used in the treatment of hyperlipidaemias. Furthermore, as a consequence of their anti-lipolytic activity, the compounds have the ability to lower elevated blood glucose, insulin and ketone body levels and therefore may be of value in the therapy of diabetes. Since anti-lipolytic agents have hypolipidaemic and hypofibrinogenaemic activity, the compounds may also show anti-atherosclerotic activity. The anti-lipolytic activity of compounds of the invention has been demonstrated by their ability to lower the concentration of non-esterified fatty acids (NEFA) in starved rats dosed orally according to the method described by P. Strong et al. In Clinical Science (1993), 84, 663–669.

In addition to their anti-lipolytic effect, the compounds of the invention may independently affect cardiac function by reducing heart rate and conduction. The compounds may thus be used in the therapy of a number of cardiovascular disorders, for example cardiac arrythmias, particularly following myocardial infarction, and angina.

Furthermore, the compounds of the invention are useful as cardioprotective agents, having applicability in the treatment of ischaemic heart disease. As used herein the term "ischaemic heart disease" includes damage associated with both myocardial ischaemia and reperfusion, for example, associated with coronary artery bypass grafting (CABG), percutaneous translumenal coronary angioplasty (PTCA), cardioplegia, acute myocardial infarction, thrombolysis, stable and unstable angina and cardiac surgery including in particular cardiac transplantation. The compounds of the invention additionally are useful for treating ischaemic damage to other organs. The compounds of the invention may also be valuable in the treatment of other disorders arising as a result of widespread atheromatous disease, for example, peripheral vascular disease (PVD) and stroke.

The compounds may also inhibit renin release and thus be of use in the therapy of hypertension and heart failure. The compounds may also be useful as CNS agents (e.g. as hypnotics, sedatives, analgesics and/or anti-convulsants particularly finding use in the treatment of epilepsy).

In addition, the compounds of the invention may find use in the treatment of sleep apnoea.

The compound of formula (I) and pharmaceutically acceptable acid addition salts thereof are useful as analgesics. They are therefore useful in treating or preventing pain. They may be used to improve the condition of a host, typically of a human being, suffering from pain. They may be employed to alleviate pain in a host. Thus, the compound of formula (I) and its pharmaceutically acceptable acid addition salts may be used as a preemptive analgesic to treat acute pain such as musculoskeletal pain, post operative pain and surgical pain, chronic pain such as chronic inflammatory pain (e.g. rheumatoid arthritis (RA) and osteoarthritis (OA), neuropathic pain (e.g. post herpetic neuralgia (PHN), trigeminal neuralgia, neuropathies associated with diabetes and sympathetically maintained pain) and pain associated with cancer and fibromyalgia. The compound of formula (I) may also be used in the treatment or prevention of pain associated with migraine, tension headache and cluster headaches and pain associated with Functional Bowel Disorders (e.g. Irritable Bowel Syndrome), non cardiac chest pain and non ulcer dyspepsia.

Additionally, when topically administered, the compounds of the present invention exhibit analgesic and anti-inflammatory activity and are therefore useful in a number of chronic inflammatory pain conditions such as OA, RA and neuropathic conditions such as fibomyalgia and PHN.

Accordingly, the invention provides a compound of formula (I) or a physiologically acceptable salt or solvate thereof for use in therapy, and in particular in the treatment of human or animal subjects suffering from a condition in which there is an advantage in decreasing plasma free fatty acid concentration, or reducing heart rate and conduction, or whereby the therapy involves the treatment of ischaemic heart disease, peripheral vascular disease or stroke or which subject is suffering from a CNS disorder, sleep apnoea or pain.

In a further aspect, the invention provides a method of treatment of a human or animal subject suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering a CNS disorder or suffering from sleep apnoea or suffering pain, which method comprises administering to the subject an effective amount of a compound of formula (I) or a pharmaceutically acceptable salt or solvate thereof.

In a further aspect, the invention provides the use of a compound of formula (I) or a pharmaceutically acceptable salt or solvate thereof for the manufacture of a medicament for the treatment of a human or animal suffering from a condition in which there is an advantage in decreasing plasma free fatty acid concentration, or reducing heart rate and conduction, or which subject is suffering from or susceptible to ishaemic heart disease, peripheral vascular disease or stroke, or which subject is suffering a CNS disorder or suffering from sleep apnoea or suffering pain.

In respect of the above mentioned ischaemic treatment, it has been found that according to a particularly unexpected aspect of the present invention, not only does administration of a compound of formula (I) prior to ischaemia provide protection against myocardial infarction, but protection is also afforded if the compound of formula (I) is administered after the ischaemic event and before reperfusion. This means that the methods of the present invention are applicable not only where ischaemia is planned or expected, for example in cardiac surgery, but also in cases of sudden or unexpected ischaemia, for example in heart attack and unstable angina.

It will be appreciated that reference to treatment includes acute treatment or prophylaxis as well as the alleviation of established symptoms.

The pharmaceutical composition comprises, as active ingredient, at least one compound of formula (I) or a pharmaceutically acceptable salt or solvate thereof in association with a pharmaceutical carrier and/or excipient for use in therapy, and in particular in the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering from a CNS disorder, sleep apnoea or pain.

There is further provided by the present invention a process of preparing a pharmaceutical composition, which process comprises mixing at least one compound of formula (I) or a pharmaceutically acceptable salt or solvate thereof, together with a pharmaceutically acceptable carrier and/or excipient.

Compositions according to the invention may be formulated for topical, oral, buccal, parenteral or rectal administration or in a form suitable for administration by inhalation or insufflation. Oral administration is preferred. The compositions may be adapted for sustained release.

For topical administration, the pharmaceutical composition may be given in the form of a transdermal patch.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The preparations may also contain buffer salts, flavouring, colouring and sweetening agents (e.g. mannitol) as appropriate.

For buccal administration the compositions may take the form of tablets or lozenges formulated in conventional manner.

The compounds of formula (I) may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated as suppositories, e.g. containing conventional suppository bases such as cocoa butter or other glycerides.

A proposed dose of the compounds of the invention for administration to man (of approximately 70 kg body weight) is 1 mg to 2 g, preferably 1 mg to 100 mg, of the active ingredient per unit dose which could be administered, for example, 1 to 4 times per day. It will be appreciated that it may be necessary to make routine variations to the dosage, depending on the age and condition of the patient. The dosage will also depend on the route of administration.

In a yet further aspect the invention also provides for the use of a compound of formula (I) or a pharmaceutically acceptable salt or solvate thereof for the manufacture of a medicament for the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease (PVD) or stroke, or which patient is suffering from a CNS disorder, sleep apnoea or pain.

The compounds of formula (I) and physiologically acceptable salts or solvates thereof may be prepared by the processes described hereinafter, said processes constituting a further aspect of the invention. In the following description, the groups $R^1$, $R^2$ and $R^3$ are as defined for compounds of formula (I) unless otherwise stated.

According to a first general process A, a compound of formula (I) may be prepared by reacting a compound of formula (II)

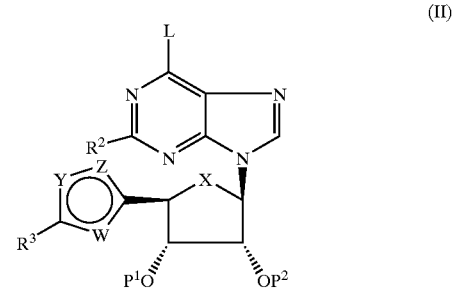

wherein L represents a leaving group such as a halogen atom (e.g. chlorine), or a linker group capable of binding to a solid phase polymeric support (e.g. a polystyrene resin) and for example may be —$SO_2C_{1-4}$alkylene and $P^1$ and $P^2$ represent hydrogen, $C_{1-6}$ straight chain or branched alkyl or a suitable protecting group (e.g. acetyl or a protecting group wherein $P^1$ and $P^2$ together form an alkylidine group) with a compound of formula $R^1NH_2$ or a salt thereof under basic conditions. The 4'-heterocycle group substituent may be protected if required, for example, see route Bb and V described hereinbelow.

Compounds of formula (II) may be used to produce compounds of formula (I) directly by reaction with the group $R^1NH_2$ either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform), an aromatic hydrocarbon (e.g. toluene), dimethyl sulfoxide (DMSO) or acetonitrile, preferably at an elevated temperature (e.g. up to the reflux temperature of the solvent), in the presence of a suitable acid scavenger, for example, inorganic bases such as sodium, cesium or potassium carbonate, or organic bases such as triethylamine, diisopropylethylamine or pyridine, optionally in the presence of a palladium catalyst (e.g. palladium acetate) and phosphine ligand (e.g. R-(+)-2,2'-bis (diphenylphosphino)-1–1'binaphthyl).

Optionally, where at least one of Y, Z and W is N, alkylation may be carried out on a N atom at Y, Z or W at any appropriate stage in the synthesis, for example, see Route X described hereinbelow.

The above reactions may be preceded or followed where appropriate by in situ removal of the $P^1$ and $P^2$ protecting groups. For example when $P^1$ and $P^2$ represent acetyl, this may be effected with an amine such as ammonia or tert-butylamine in a solvent such as methanol or when $P^1$ and $P^2$ represent an alkylidine by acid hydrolysis, e.g. with trifluoroacetic acid (TFA). Interconversion of $P^1$ and $P^2$ protecting groups may occur at any stage in the preparation of the compounds of formula (II), for example when P¹ and P² represent acetyl, compounds of formula (II) may be prepared from compounds wherein P¹ and P² together represent an alkylidine protecting group by acid catalysed removal of the alkylidine protecting group, e.g. with hydrogen chloride in methanol followed by in situ acylation, for example with acetic anhydride in the presence of a base such as pyridine, in a solvent such as dichloromethane.

Otherwise, interconversion of P¹ and P² protecting groups may occur at any stage during the preparation of compounds of formula (II).

It will be apparent to persons skilled in the art that in the preparation of compounds of formula (II) or (I) the 4'-heterocycle may be formed at any stage. For example, heterocycles may be prepared from carboxylic acid or acetylene starting materials before the addition of the purine ring (see Schemes 1, 1 a and 2) or heterocycles may be formed after the addition of the purine ring (see Schemes 3, 4 and 5 and Route W).

Compounds of formula (II) where X=O may be prepared by reacting compounds of formula (III)

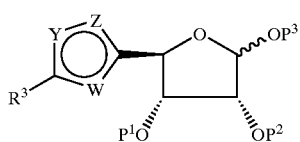
(III)

wherein P³ represents a suitable protecting group, for example acetyl, or a substituent such as $C_{1-3}$ alkyl, and P¹, P² and R³ are as defined above, with compounds of formula (IV)

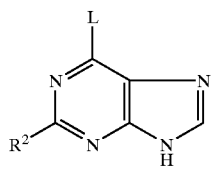
(IV)

wherein L and R² are as defined above.

The reaction is conveniently carried out in a suitable solvent, such as acetonitrile in the presence of a silylating agent such as trimethylsilyl trifluoromethane sulfonate and a base such as diazabicyclo[5.4.0]undec-7-ene (DBU). Alternatively the compound of formula (IV) may first be silylated with a suitable silylating agent e.g. hexamethyldisilazane followed by reaction of the silylated intermediate with a compound of formula (III) and a suitable Lewis acid, e.g. trimethylsilyl trifluoromethanesulfonate in a suitable solvent such as acetonitrile.

Compounds of formula (IV) are either known in the art or may be prepared from known compounds using methods analogous to those used to prepare the known compounds of formula (IV).

As described above, the compounds of formula (III) may be prepared from alternative protected compounds by replacement of the alternate P¹ and P² protecting groups with other P¹ and P² groups. These represent an exchanging of one protecting group for another and will be apparent to those skilled in the art. Compounds of formula (III) may be made for example by the following syntheses:

Compounds of formula (III) may be prepared, for example when the heterocycle defined by W, Y and Z hereinabove represents an isoxazole (optionally substituted) by the following reaction schemes.

Scheme 1

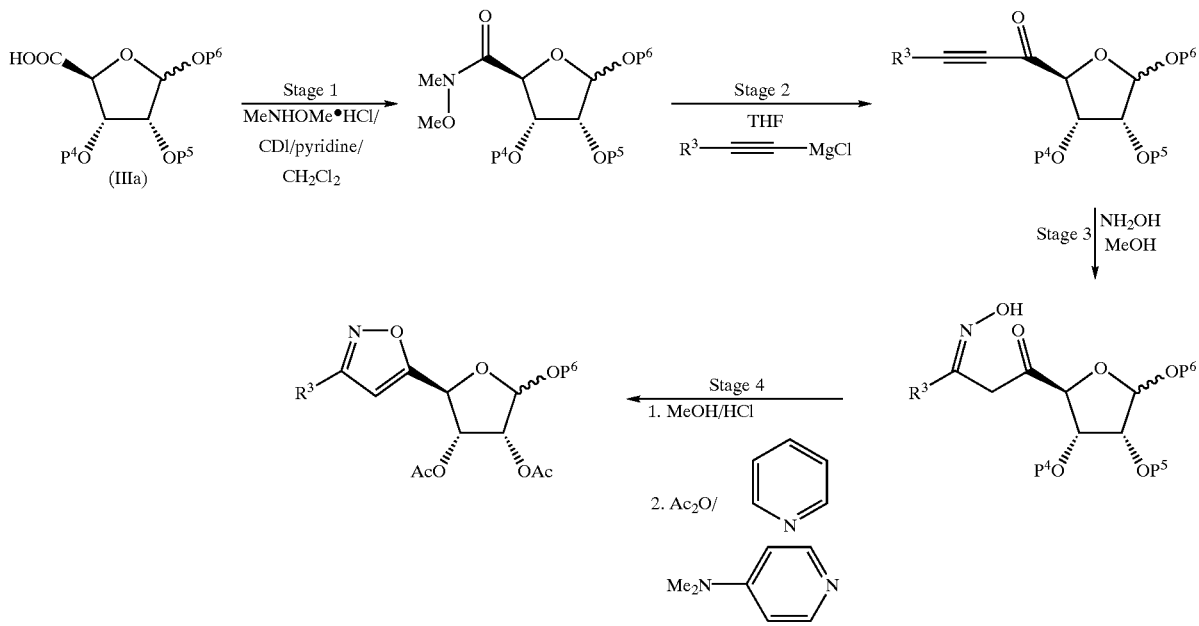

General conditions for Stages 1–4 will be known to persons skilled in the art. It will also be appreciated that the reagents and conditions set out in Scheme 1 are example conditions and alternative reagents and conditions for achieving the same chemical transformation may be known to persons skilled in the art. $P^4$ and $P^5$ together represent alkylidine protecting group(s). $P^6$ represents $C_{1-4}$ alkyl. $R^3$ is as previously defined.

Although scheme 1 shows the preparation of compounds of formula (III) where the heterocycle moiety is an isoxazole it would be apparent to a person skilled in the art that other standard methods could be employed to produce compounds of formula (III) with other heterocycles from carboxylic acid starting materials, such a compound of formula (IIIa), for example, see route Q as described hereinbelow.

An alternative method for synthesis of compounds of formula (III) is shown in Scheme 1 a.

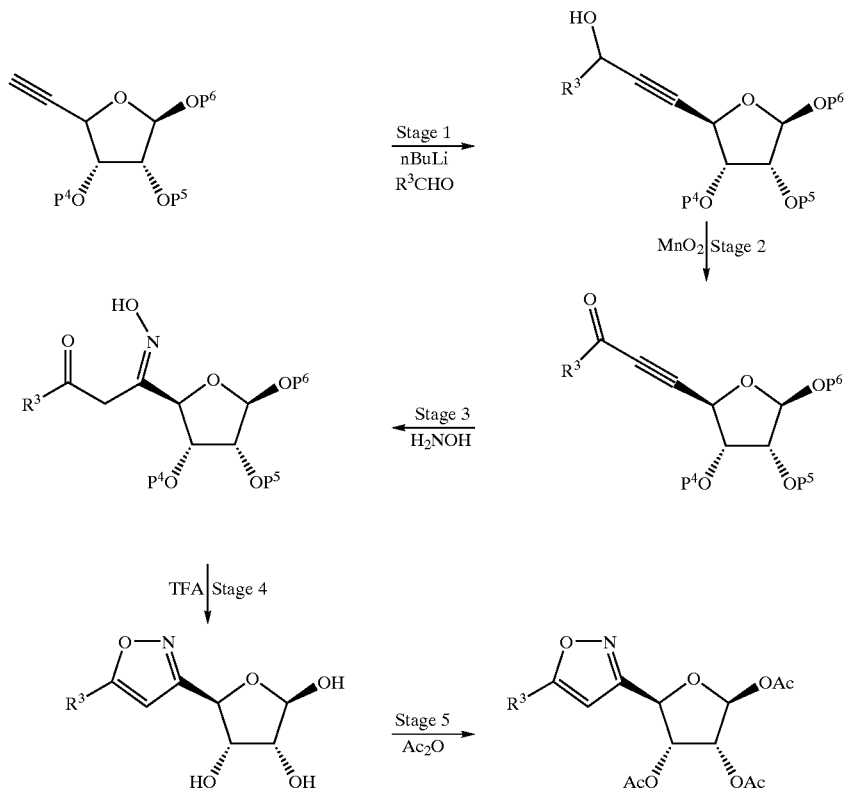

Scheme 1a

General conditions for Stages 1–5 in Scheme 1 a will be known to persons skilled in the art. $R^3$, $P^1$, $P^5$ and $P^6$ are as previously defined.

Scheme 2 represents a method of preparing compounds of formula (III) when Y=N, Z=NH, W=CH and $R^3$=H or tautomers thereof. $P^1$, $P^2$ and $P^6$ are as previously defined.

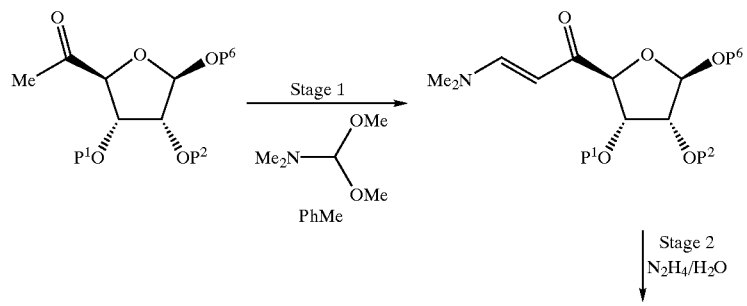

Scheme 2

-continued

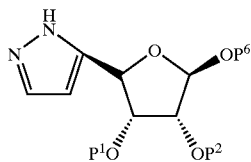

A further process (B) comprises converting a compound of formula (I) into a different compound of formula (I) by modifying the $R^1$, $R^2$ and/or $R^3$ groups therein.

All compounds of formulae (III) are novel intermediates and form a further aspect of the present invention.

Compounds of the formula $R^1NH_2$ are either known compounds or may be prepared from known compounds using conventional procedures.

Specific optical isomers of a compound of formula (I) may be obtained by conventional methods for examples by synthesis from an appropriate asymmetric starting material using any of the processes described herein, or where appropriate by separation of a mixture of isomers of a compound of formula (I) by conventional means e.g by fractional crystallisation or chromatography.

According to a third process (C), compounds of formula (I) may be prepared from compounds of formula (V) or (VI):

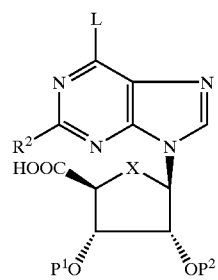
(V)

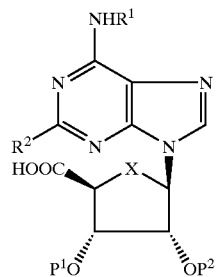
(VI)

where $R^1$, $R^2$, X, L, $P^1$ and $P^2$ represent groups as previously defined.

Also compounds of formula (VI) may be prepared from compounds of formula (V) by analogous methods to those described in process (A) above.

Synthesis of the compounds of formulae (I) from the corresponding acids of formulae (V) and (VI) will be apparent to a skilled person using conventional synthetic techniques.

As an example, when W=O, Y=N and Z=N in formula I above thus defining a 1,3,4 oxadiazole, the synthesis is according to reaction scheme 3. J represents a leaving group L as previously defined, or a $NHR^1$ group. $R^2$, X, $P^1$ and $P^2$ are as previously defined.

Scheme 3

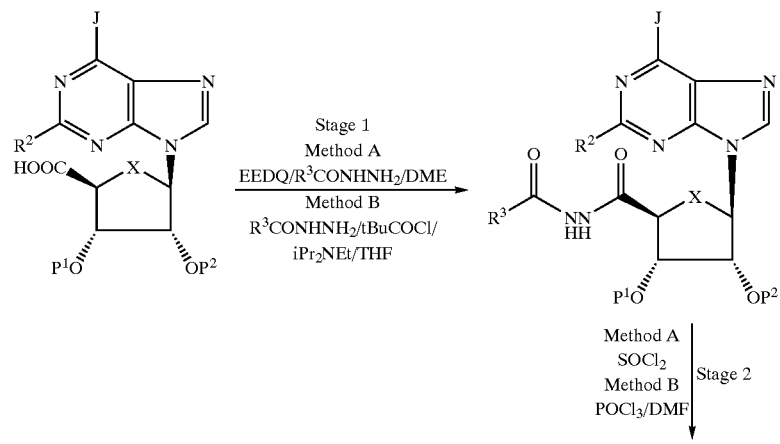

-continued

Continue as described in Process A ←

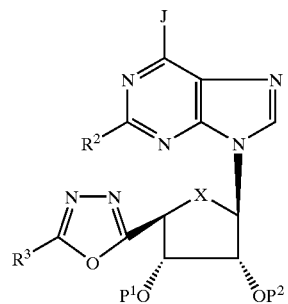

Compounds of formula (I) where Z=O, Y=N and W=N (thus defining a 1,2,4-oxadiazole) may be prepared from compounds of formula (V) or (VI) by a first process involving activation of the carboxyl group on the compound of formula (V) or (VI) followed by reaction with an amidoxime of formula HO—N=C($R^3$)$NH_2$ in a solvent such as tetrahydrofuran or chloroform, in the presence of a base such as pyridine or di-isopropylethylamine, followed by cyclisation at a temperature of 20° C.-150° C. in a solvent such as toluene, tetrahydrofuran (THF) or chloroform (see scheme 4). Methods of carboxyl activation include reaction with an acid chloride, such as pivaloyl chloride, or an acid anhydride in the presence of a base such as a tertiary amine, for example di-isopropylethylamine, or with thionyl chloride in dimethylformamide (DMF). Activating agents used in peptide chemistry such as 2-ethoxy-1-ethoxycarbonyl-1,2-dihydroquinoline (EEDQ) or 1-hydroxybenzotriazole and 1-(3-dimethylaminopropyl)-3-ethyl-carbodiimide hydrochloride, may also be used. Hydroxyl protecting groups may be removed under conditions known to those practising in the art. For example, the acetonide group may be removed by treatment with an acid (at a temperature of 0° C.-150° C.) such as trifluoroacetic acid suitably at 0–20° C. or acetic acid suitably at 50–150° C.

In scheme 4 $R^2$, $R^3$, X, J, $P^1$ and $P^2$ and are as defined above.

Scheme 4

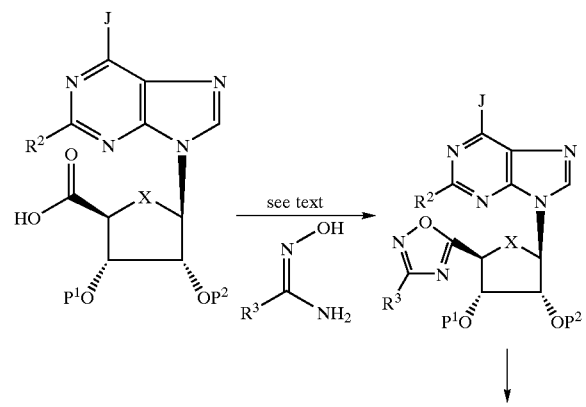

-continued

Modification of J and other protecting groups as required

Alternatively, a compound of formula (II) may be prepared from a compound of formula (VII), for example, see route U as described hereinbelow. It would be apparent to persons skilled in the art that analagous methods to route U could be used to prepare compounds of formula (I) with other 4'-heterocycles, for example, see route M as described hereinbelow.

(VII)

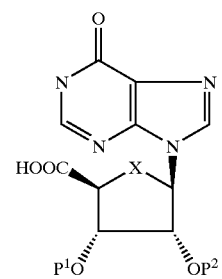

According to an general process D, a compound of formula (I) may be prepared from a compound of formula (V), as shown in Scheme 5, followed by removal of the $P^1$ and $P^2$ protecting groups as described previously in process A. It will be apparent to persons skilled in the art that analagous methods to that shown in Scheme 5 could be used to prepare compounds of formula (I) with other 4'-heterocycles using alternative heterocycle syntheses. In Scheme 5, $R^1$, $R^3$, J, $P^1$ and $P^2$ are as previously defined.

Scheme 5

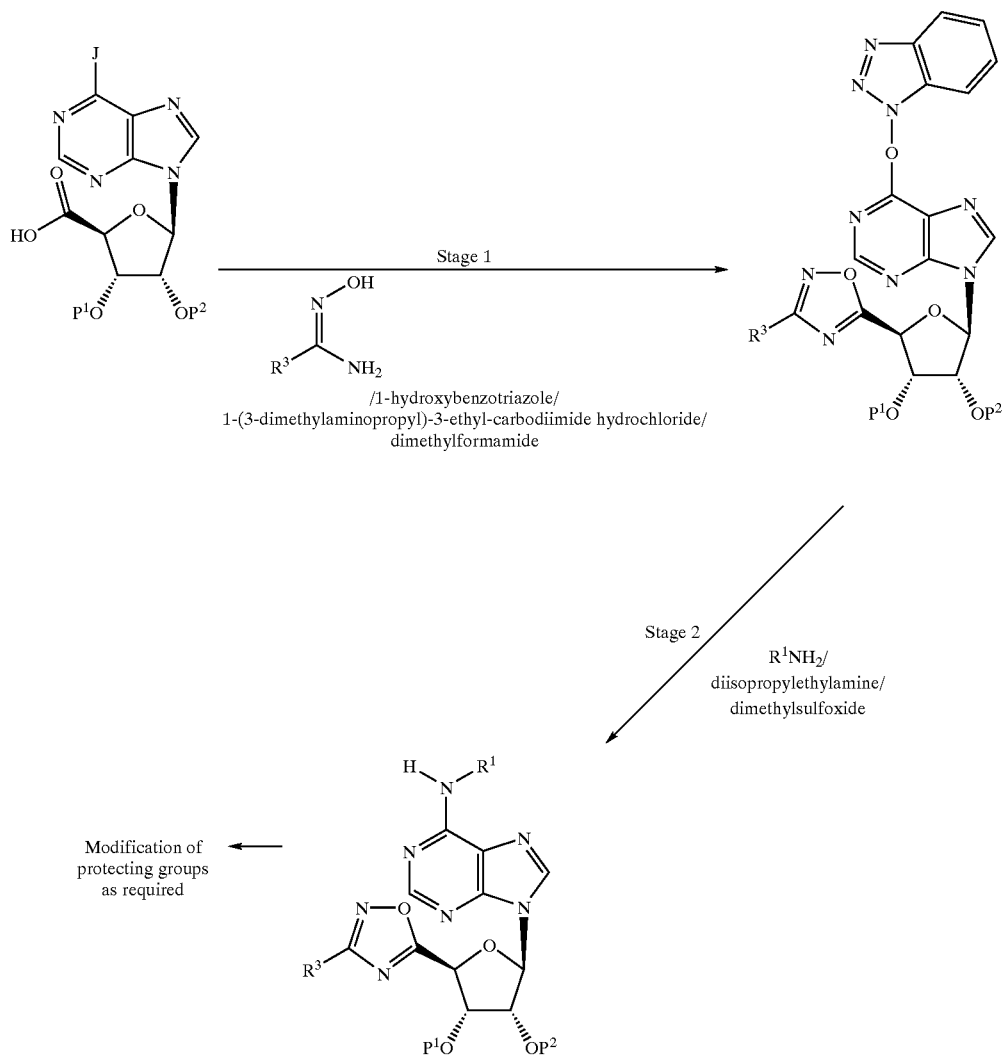

The invention is further illustrated by the following non limiting intermediates and Examples.

Full experimental details are given below for routes A–Z, Bb and Cc; data for remaining examples prepared by analogous routes are given in Table 1.

Standard HPLC conditions are as follows:
Standard Automated Preparative HPLC Column, Conditions & Eluent Automated preparative high performance liquid chromatography (autoprep. HPLC) was carried out using a Supelco ABZ+5 m 100 mm×22 mm i.d. column eluted with a mixture of solvents consisting of 1) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 0–95% (ii) over 18.5 minutes.

LC/MS System

Four alternative Liquid Chromatography Mass Spectroscopy (LC/MS) systems were used:
System A:

This system used an ABZ+PLUS, 3.3 cm×4.6 mm i.d. column, eluting with solvents: A—0.1% v/v formic acid+ 0.077% w/v ammonium acetate in water; and B—95:5 acetonitrile:water+0.05% v/v formic acid, at a flow rate of 1 ml per minute. The following gradient protocol was used: 100% A for 0.7 mins; A+B mixtures, gradient profile 0–100% B over 3.5 mins; hold at 100% B for 3.5 mins; return to 100% A over 0.3 mins.

System B:

This system used an ABZ+PLUS, 3.3 cm×2.0 mm i.d. column, eluting with solvents: A—0.1% v/v formic acid+ 0.077% w/v ammonium acetate in water, and B—95:5 acetonitrile:water+0.05% v/v formic acid, at a flow rate of 0.8 ml per minute. The following gradient protocol was used: A+B mixtures, gradient profile 0–100% B over 3.5 mins; hold at 100% B for 1.5 mins; return to 100% A over 0.5 mins.

System C:

This system used an ABZ+PLUS, 3.3 cm×4.6 mm i.d. column, eluting with solvents: A—0.1% v/v formic acid+ 0.077%w/v ammonium acetate in water; and B—95% acetonitrile:water+0.05% v/v formic acid, at a flow rate of 3 ml per minute. The following gradient protocol was used: 100% A for 0.7 mins; A+B mixtures, gradient profile 0–100% B over 3.7 mins; hold at 100% B for 0.9 mins; return to 100% A over 0.2 mins.

System D:

This system used an ABZ+PLUS, 3.3 cm×4.6 mm i.d. column, eluting with solvents: A—0.1% v/v formic acid in water; and B—95% acetonitrile:water+0.07% v/v formic acid, at a flow rate of 1.5 ml per minute. The following gradient protocol was used: 100% A for 0.2 mins; A+B mixtures, gradient profile 0–100% B over 3.3 mins; hold at 100% B for 1 min; return to 100% A over 0.2 mins.

All LC/MS systems used a micromass 'platform' spectrometer, with electrospray ionisation mode, positive and negative ion switching, mass range 80–1000 a.m.u.

Flash chromatography was carried out either on Merck silica gel (Merck 9385), or on pre-packed silica gel cartridges (Biotage).

All temperatures were in ° C.

Examples Table

TABLE 1

Examples

| Ex No | Name | Expt. Details (note 1) | Characterising data |
|---|---|---|---|
| 1 | (2R,3R,4S,5S)-2-[6-(2R-Hydroxy-cyclopent-(R)-ylamino)-purin-9-yl]-5-(5-isopropyl-[1,3,4]-oxadiazol-2-yl)-tetrahydro-furan-3,4-diol | Analogous method to route A | TLC $SiO_2$ ($CH_2Cl_2$:MeOH:880$NH_3$ 90:10:1) $R_f$ = 0.39 Microanalysis Found: C, 52.9; H, 5.9; N, 22.7. $C_{19}H_{23}N_7O_5$ requires C, 52.9; H, 5.8; N, 22.7. |
| 2 | (2R,3R,4S,5S)-2-(6-Cyclopentylamino-purin-9-yl)-5-(5-phenyl-[1,3,4]-oxadiazol-2-yl)-tetrahydro-furan-3,4-diol | Analogous method to route A | TLC $SiO_2$ ($CH_2Cl_2$:MeOH:880$NH_3$ 94:6:1) $R_f$ = 0.10 Microanalysis Found: C, 57.1; H, 5.3; N, 21.0. $C_{22}H_{23}N_7O_4$ requires C, 57.2; H, 5.3; N, 21.2. |
| 3 | (2S,3S,4R,5R)-2-(5-tert-Butyl-[1,3,4]oxadiazol-2-yl)-5-[6-(tetrahydro-pyran-4-ylamino)-purin-9-yl]-tetrahydro-furan-3,4-diol | See below (route A) | See below (route A) |
| 4 | 4-{9-[5S-(5-tert-Butyl-[1,3,4]-oxadiazol-2-yl)-3R,4S-dihydroxy-tetrahydro-furan-2R-yl]-9H-purin-6-ylamino}-piperidine-1-carboxylic acid ethyl ester | Analogous method to route A | LC/MS (System B) $R_t$ 2.55 min. Mass Spectrum m/z 517 [MH$^+$]. |
| 5 | (2S,3S,4R,5R)-2-(5-tert-Butyl-[1,3,4]oxadiazol-2-yl)-5-[6-(2S-hydroxy-cyclopent-(S)-ylamino)-purin-9-yl]-tetrahydro-furan-3,4-diol | Analogous method to route A | LC/MS (System B) $R_t$ 2.35 min. Mass Spectrum m/z 446 [MH$^+$]. |
| 6 | (2S,3S,4R,5R)-2-(5-Isopropyl-[1,3,4]oxadiazol-2-yl)-5-[6-(tetrahydro-pyran-4-ylamino)-purin-9-yl]-tetrahydro-furan-3,4-diol | Analogous method to route A | LC/MS (System B) $R_t$ 2.24 min. Mass Spectrum m/z 432 [MH$^+$]. |
| 7 | (2S,3S,4R,5R)-2-(5-tert-Butyl-[1,3,4]oxadiazol-2-yl)-5-(6-cyclopentylamino-purin-9-yl)-tetrahydro-furan-3,4-diol | Analogous method to route A | LC/MS (System B) $R_t$ 2.61 min. Mass Spectrum m/z 430 [MH$^+$]. |
| 8 | (2S,3S,4R,5R)-2-(5-tert-Butyl- | See below (route B) | See below (route B) |

TABLE 1-continued

Examples

| Ex No | Name | Expt. Details (note 1) | Characterising data |
|---|---|---|---|
|  | [1,3,4]oxadiazol-2-yl)-5-[2-chloro-6-(tetrahydro-pyran-4-ylamino)-purin-9-yl]-tetrahydro-furan-3,4-diol formate | | |
| 9 | (2S,3S,4R,5R)-2-(5-tert-Butyl-[1,3,4]oxadiazol-2-yl)-5-(2-chloro-6-cyclopentylamino-purin-9-yl)-tetrahydro-furan-3,4-diol formate | Analogous method to route B | LC/MS (System A) $R_t$ 4.35 min. Mass Spectrum m/z 464 [MH$^+$]. |
| 10 | (2S,3S,4R,5R)-2-(5-Cyclopropyl-[1,3,4]oxadiazol-2-yl)-5-[6-(2S-hydroxy-cyclopent-(S)-ylamino)-purin-9-yl]-tetrahydro-furan-3,4-diol | Analogous method to route A | LC/MS (System D) $R_t$ 2.32 min. Mass Spectrum m/z 430 [MH$^+$]. |
| 11 | (2R,3R,4S,5S)-2-(6-Cyclopentylamino-purin-9-yl)-5-(5-cyclopropyl-[1,3,4]oxadiazol-2-yl)-tetrahydro-furan-3,4-diol | Analogous method to route A | LC/MS (System D) $R_t$ 2.44 min. Mass Spectrum m/z 414 [MH$^+$]. |
| 12 | 4-{9-[5S-(5-Cyclopropyl-[1,3,4]oxadiazol-2-yl)-3R,4S-dihydroxy-tetrahydro-furan-2R-yl]-9H-purin-6-ylamino}-piperidine-1-carboxylic acid ethyl ester | Analogous method to route A | LC/MS (System D) $R_t$ 2.57 min. Mass Spectrum m/z 501 [MH$^+$]. |
| 13 | (2R,3R,4S,5S)-2-(6-Cyclopentylamino-purin-9-yl)-5-(5-cyclopentyl-[1,3,4]oxadiazol-2-yl)-tetrahydro-furan-3,4-diol | Analogous method to route A | LC/MS (System D) $R_t$ 2.74 min. Mass Spectrum m/z 442 [MH$^+$]. |
| 14 | (2S,3S,4R,5R)-2-(5-tert-Butyl-[1,3,4]oxadiazol-2-yl)-5-[6-(4-chloro-2-fluoro-phenylamino)-purin-9-yl]-tetrahydro-furan-3,4-diol | Analogous method to route A | LC/MS (System B) $R_t$ 2.99 min. Mass Spectrum m/z 490 [MH$^+$]. |
| 15 | (2R,3R,4S,5S)-2-(6-Cyclopentylamino-purin-9-yl)-5-[1,3,4]oxadiazol-2-yl-tetrahydro-furan-3,4-diol | See below (route C) | See below (route C) |
| 16 | (2S,3S,4R,5R)-2-(5-Ethyl-oxazol-2-yl)-5-[6-(tetrahydro-pyran-4-ylamino)-purin- | See below (route D) | See below (route D) |

TABLE 1-continued

Examples

| Ex No | Name | Expt. Details (note 1) | Characterising data |
|---|---|---|---|
| 17 | 9-yl]-tetrahydro-furan-3,4-diol (2S,3S,4R,5R)-2-(6-Cyclopentylamino-purin-9-yl)-5-(5-cyclopropyl-[1,3,4]thiadiazol-2-yl)-tetrahydro-furan-3,4-diol | See below (route E) | See below (route E) |
| 18 | (2R,3R,4S,5R)-2-(6-Isopropylamino-purin-9-yl)-5-(5-methyl-4H-[1,2,4]triazol-3-yl)-tetrahydro-furan-3,4-diol trifluoroacetate | See below (route F) | See below (route F) |
| 19 | (2S,3S,4R,5R)-2-(3-Cyclopropyl-[1,2,4]oxadiazol-5-yl)-5-[6-(2S-hydroxy-cyclopent-(S)-ylamino)-purin-9-yl]-tetrahydro-furan-3,4-diol | See below (route G) | LC/MS (System B) $R_t$ 2.37 min. Mass Spectrum m/z 430 [MH$^+$]. |
| 20 | (2S,3S,4R,5R)-2-(3-Phenyl-[1,2,4]-oxadiazol-5-yl)-5-[6-(tetrahydro-pyran-4-ylamino)-purin-9-yl]-tetrahydro-furan-3,4-diol | Analogous method to route G | TLC SiO$_2$ (CH$_2$Cl$_2$:EtOH: 880NH$_3$) 100:8:1 $R_f$ = 0.5 Microanalysis Found: C, 54.8; H, 4.9; N,20. Requires C, 55.3; H, 5.3; N, 19.6. |
| 21 | (2S,3S,4R,5R)-2-(3-tert-Butyl-[1,2,4]oxadiazol-5-yl)-5-[6-(2S-hydroxy-cyclopent-(S)-ylamino)-purin-9-yl]-tetrahydro-furan-3,4-diol | Analogous method to route G | LC/MS (System B) $R_t$ 2.57 min. Mass Spectrum m/z 446 [MH$^+$]. |
| 22 | (2S,3S,4R,5R)-2-(3-Cyclopropyl-[1,2,4]oxadiazol-5-yl)-5-[6-(tetrahydro-pyran-4-ylamino)-purin-9-yl]-tetrahydro-furan-3,4-diol | Analogous method to route G | LC/MS (System B) $R_t$ 2.39 min. Mass Spectrum m/z 430 [MH$^+$]. |
| 23 | (2R,3R,4S,5S)-2-[6-(Tetrahydro-pyran-4-ylamino)-purin-9-yl]-5-(3-thiazol-5-yl-[1,2,4]oxadiazol-5-yl)-tetrahydro-furan-3,4-diol | Analogous method to route G | LC/MS (System B) $R_t$ 2.29 min. Mass Spectrum m/z 473 [MH$^+$]. |
| 24 | (2S,3S,4R,5R)-2-(3-Methyl-[1,2,4]-oxadiazol-5-yl)-5-[6-(tetrahydro-pyran-4-ylamino)-purin-9-yl]-tetrahydro-furan-3,4-diol | Analogous method to route G | $^1$HNMR δ (DMSO) 8.42 (1H,s,CH), 8.20 (1H,brs,CH), 7.82 (1H,brd,NH), 6.18 (1H,d,CH), 6.02 (1H,brd,OH), 5.90 (1H,brd,OH), 5.22 (1H,d,CH), 4.38 (1H,brs,CH), 3.94 (2H,brd,2xCH equatorial), 3.42 (2H,t,2xCH axial), |

TABLE 1-continued

Examples

| Ex No | Name | Expt. Details (note 1) | Characterising data |
|---|---|---|---|
| | | | 2.40 (3H,s,CH$_3$), 1.90-1.60 (4H,2xm,2xCH$_2$). Microanalysis Found: C, 50.6; H, 5.2; N, 24.3. Requires C, 50.6; H, 5.25; N, 24.3. |
| 25 | (2R,3R,4S,5S)-2-[6-(3-Fluoro-4-hydroxy-phenylamino)-purin-9-yl]-5-(3-methyl-[1,2,4]-oxadiazol-5-yl)-tetrahydro-furan-3,4-diol | Analogous method to route G | LC/MS (System C) R$_t$ 2.53 min. Mass Spectrum m/z 430 [MH$^+$]. |
| 26 | 4-{9-[5R-(5-tert-Butyl-[1,2,4]-oxadiazol-3-yl)-3R,4S-dihydroxy-tetrahydro-furan-2R-yl]-9H-purin-6-ylamino)-piperidine-1-carboxylic acid ethyl ester | See below (route H) | LC/MS (System B) R$_t$ 2.76 min. Mass Spectrum m/z 517 [MH$^+$]. |
| 27 | (2S,3S,4R,5R)-2-(3-tert-Butyl-isoxazol-5-yl)-5-[6-(2S-hydroxy-cyclopent-(S)-ylamino)-purin-9-yl]-tetrahydro-furan-3,4-diol | See below (route I) | See below (route I) |
| 28 | (2S,3S,4R,5R)-2-(3-tert-Butyl-isoxazol-5-yl)-5-[6-(tetrahydro-pyran-4-ylamino)-purin-9-yl]-tetrahydro-furan-3,4-diol | See below (route I) | See below (route I) |
| 29 | (2R,3R,4S,5R)-2-(2H-Pyrazol-3-yl)-5-(6-tetrahydro-pyran-4-ylamino-purin-9-yl)-tetrahydro-furan-3,4-diol | See below (route J) | See below (route J) |
| 30 | (2R,3R,4S,5R)-2-(5-tert-Butyl-2H-pyrazol-3-yl)-5-(6-cyclopentylamino-purin-9-yl)-tetrahydro-furan-3,4-diol | See below (route K) | See below (route K) |
| 31 | (2R,3R,4S,5S)-2-[6-(1S-hydroxy-methyl-2-phenyl-ethylamino)-2-methoxy-purin-9-yl]-5-(3-ethyl-isoxazol-5-yl)-tetrahydro-furan-3,4-diol | See below (route L) | See below (route L) |
| 32 | (1S,2R,3S,5R)-3-(3-Cyclopropyl-[1,2,4]oxadiazol-5-yl)-5-[2S-hydroxy-cyclopent-(S)-ylamino)- | See below (route M) | See below (route M) |

TABLE 1-continued

Examples

| Ex No | Name | Expt. Details (note 1) | Characterising data |
|---|---|---|---|
| | purin-9-yl]-cyclopentane-1,2-diol | | |
| 33 | (2R,3R,4S,5S)-2-[6-(tert-butylamino)-9H-purin-9-yl]-5-(3-cyclopropyl-1,2,4-oxadiazol-5-yl)-tetrahydrofuran-3,4-diol | Analogous method to route G | LC/MS (System C) $R_t$ 2.91 min. Mass Spectrum m/z 402 [MH⁺]. |
| 34 | (2S,3S,4R,5R)-2-(3-cyclopropyl-1,2,4-oxadiazol-5-yl)-5-[6-(isopropylamino)-9H-purin-9-yl]-tetrahydrofuran-3,4-diol | Analogous method to route G | LC/MS (System C) $R_t$ 2.54 min. Mass Spectrum m/z 388 [MH⁺]. |
| 35 | (2R,3R,4S,5S)-2-(6-{[(1R,2R)-2-hydroxy-cyclopentyl]-amino}-9H-purin-9-yl)-5-(3-methyl-1,2,4-oxadiazol-5-yl)-tetrahydrofuran-3,4-diol | Analogous method to route G | LC/MS (System C) $R_t$ 2.32 min. Mass Spectrum m/z 404 [MH⁺]. |
| 36 | (2S,3S,4R,5R)-2-(3-methyl-1,2,4-oxadiazol-5-yl)-5-[6-(tetrahydro-2H-thiopyran-4-ylamino)-9H-purin-9-yl]tetrahydrofuran-3,4-diol | Analogous method to route G | LC/MS (System C) $R_t$ 2.54 min. Mass Spectrum m/z 420 [MH+]. |
| 37 | ethyl 4-({9-[(2R,3R,4S,5S)-3,4-dihydroxy-5-(3-methyl-1,2,4-oxadiazol-5-yl)-tetrahydrofuran-2-yl]-9H-purin-6-yl}amino)-piperidine-1-carboxylate | Analogous method to route G | LC/MS (System C) $R_t$ 2.56 min. Mass Spectrum m/z 475 [MH⁺]. |
| 38 | (2R,3R,4S,5S)-2-[6-(isobutyl-amino)-9H-purin-9-yl]-5-(3-methyl-1,2,4-oxadiazol-5-yl)-tetrahydrofuran-3,4-diol | Analogous method to route G | LC/MS (System C) $R_t$ 2.51 min. Mass Spectrum m/z 376 [MH⁺]. |
| 39 | (2R,3R,4S,5S)-2-[6-(cyclopentyl-amino)-9H-purin-9-yl]-5-(3-methyl-1,2,4-oxadiazol-5-yl)-tetrahydrofuran-3,4-diol | Analogous method to route G | LC/MS (System C) $R_t$ 2.47 min. Mass Spectrum m/z 388 [MH⁺]. |
| 40 | (2R,3R,4S,5S)-2-{6-[(cyclopropyl-methyl)amino]-9H-purin-9-yl}-5-(3-methyl-1,2,4-oxadiazol-5-yl)-tetrahydrofuran-3,4-diol | Analogous method to route G | LC/MS (System C) $R_t$ 2.41 min. Mass Spectrum m/z 374 [MH⁺]. |
| 41 | (2R,3R,4S,5S)-2-[6-(cyclopropyl-amino)-9H-purin-9- | Analogous method to route G | LC/MS (System C) $R_t$ 2.17 min. Mass Spectrum |

TABLE 1-continued

Examples

| Ex No | Name | Expt. Details (note 1) | Characterising data |
|---|---|---|---|
| | yl]-5-(3-methyl-1,2,4-oxadiazol-5-yl)-tetrahydrofuran-3,4-diol | | m/z 360 [MH$^+$]. |
| 42 | (2R,3R,4S,5S)-2-[6-(2-fluoroanilino)-9H-purin-9-yl]-5-(3-methyl-1,2,4-oxadiazol-5-yl)-tetrahydrofuran-3,4-diol | Analogous method to route G | LC/MS (System C) R$_t$ 2.71 min. Mass Spectrum m/z 414 [MH$^+$]. |
| 43 | (2R,3R,4S,5S)-2-[6-(2,4-difluoroanilino)-9H-purin-9-yl]-5-(3-methyl-1,2,4-oxadiazol-5-yl)-tetrahydrofuran-3,4-diol | Analogous method to route G | LC/MS (System C) R$_t$ 2.75 min. Mass Spectrum m/z 432 [MH$^+$]. |
| 44 | (2S,3S,4R,5R)-2-[3-(tert-butyl)-1,2,4-oxadiazol-5-yl]-5-{6-[(cyclopropyl-methyl)amino]-9H-purin-9-yl}-tetrahydrofuran-3,4-diol | Analogous method to route N | LC/MS (System C) R$_t$ 2.77 min. Mass Spectrum m/z 416 [MH$^+$]. |
| 45 | (2S,3S,4R,5R)-2-[3-(tert-butyl)-1,2,4-oxadiazol-5-yl]-5-[6-(isobutylamino)-9H-purin-9-yl]-tetrahydrofuran-3,4-diol | See Below (route N) | LC/MS (System C) R$_t$ 2.88 min. Mass Spectrum m/z 418 [MH$^+$]. |
| 46 | 2-[(9-{(2R,3R,4S,5S)-5-[3-(tert-butyl)-1,2,4-oxadiazol-5-yl]-3,4-dihydroxy-tetrahydrofuran-2-yl}-9H-purin-6-yl)amino]-N-methylethane-sulfonamide | Analogous method to route N | LC/MS (System C) R$_t$ 2.54 min. Mass Spectrum m/z 483 [MH$^+$]. |
| 47 | (2S,3S,4R,5R)-2-[3-(tert-butyl)-1,2,4-oxadiazol-5-yl]-5-{6-[(1,1-dioxidotetrahydro-2H-thiopyran-4-yl}amino]-9H-purin-9-yl}-tetrahydro-furan-3,4-diol | Analogous method to route N | LC/MS (System C) R$_t$ 2.51 min. Mass Spectrum m/z 494 [MH$^+$]. |
| 48 | (2S,3S,4R,5R)-2-[3-(tert-butyl)-1,2,4-oxadiazol-5-yl]-5-[6-(2-chloro-4-fluoroanilino)-9H-purin-9-yl]-tetrahydrofuran-3,4-diol | Analogous method to route O | LC/MS (System C) R$_t$ 3.20 min. Mass Spectrum m/z 490 [MH$^+$]. |
| 49 | (2S,3S,4R,5R)-2-[3-(tert-butyl)-1,2,4-oxadiazol-5-yl]-5-[6-(2,4-difluoroanilino)- | See below (route O) | LC/MS (System C) R$_t$ 3.03 min. Mass Spectrum m/z 474 [MH$^+$]. |

TABLE 1-continued

Examples

| Ex No | Name | Expt. Details (note 1) | Characterising data |
|---|---|---|---|
| | 9H-purin-9-yl]-tetrahydrofuran-3,4-diol | | |
| 50 | (2S,3S,4R,5R)-2-[3-(tert-butyl)-1,2,4-oxadiazol-5-yl]-5-[6-(3,4-difluoroanilino)-9H-purin-9-yl]-tetrahydrofuran-3,4-diol | Analogous method to route O | LC/MS (System C) $R_t$ 3.32 min. Mass Spectrum m/z 474 [MH$^+$]. |
| 51 | (2R,3R,4S,5S)-2-[6-(cyclopropyl-amino)-9H-purin-9-yl]-5-(3-isopropyl-1,2,4-oxadiazol-5-yl)-tetrahydrofuran-3,4-diol | Analogous method to route N | LC/MS (System C) $R_t$ 2.39 min. Mass Spectrum m/z 388 [MH$^+$]. |
| 52 | (2R,3R,4S,5S)-2-[6-(isobutyl-amino)-9H-purin-9-yl]-5-(3-isopropyl-1,2,4-oxadiazol-5-yl)-tetrahydrofuran-3,4-diol | Analogous method to route N | LC/MS (System C) $R_t$ 2.74 min. Mass Spectrum m/z 404 [MH$^+$]. |
| 53 | (2R,3R,4S,5S)-2-{6-[(cyclopropyl-methyl)amino]-9H-purin-9-yl}-5-(3-isopropyl-1,2,4-oxadiazol-5-yl)-tetrahydrofuran-3,4-diol | Analogous method to route N | LC/MS (System C) $R_t$ 2.65 min. Mass Spectrum m/z 402 [MH$^+$]. |
| 54 | 2-({9-[(2R,3R,4S,5S)-3,4-dihydroxy-5-(3-isopropyl-1,2,4-oxadiazol-5-yl)-tetrahydrofuran-2-yl]-9H-purin-6-yl}amino)-N-methylethane-sulfonamide | Analogous method to route N | LC/MS (System C) $R_t$ 2.58 min. Mass Spectrum m/z 469 [MH$^+$]. |
| 55 | (2R,3R,4S,5S)-2-[6-(2,4-difluoroanilino)-9H-purin-9-yl]-5-(3-isopropyl-1,2,4-oxadiazol-5-yl)-tetrahydrofuran-3,4-diol | Analogous method to route O | LC/MS (System C) $R_t$ 2.96 min. Mass Spectrum m/z 460 [MH$^+$]. |
| 56 | (2R,3R,4S,5S)-2-[6-(3,4-difluoroanilino)-9H-purin-9-yl]-5-(3-isopropyl-1,2,4-oxadiazol-5-yl)-tetrahydrofuran-3,4-diol | Analogous method to route O | LC/MS (System C) $R_t$ 3.20 min. Mass Spectrum m/z 460 [MH$^+$]. |
| 57 | (2R,3R,4S,5S)-2-[6-(4-fluoro-2-methylanilino)-9H-purin-9-yl]-5-(3-isopropyl-1,2,4-oxadiazol-5-yl)-tetrahydrofuran-3,4-diol | Analogous method to route O | LC/MS (System C) $R_t$ 3.05 min. Mass Spectrum m/z 456 [MH$^+$]. |

TABLE 1-continued

Examples

| Ex No | Name | Expt. Details (note 1) | Characterising data |
|---|---|---|---|
| 58 | (2S,3S,4R,5R)-2-[3-(dimethyl-amino)-1,2,4-oxadiazol-5-yl]-5-[6-(tetrahydro-2H-pyran-4-ylamino)-9H-purin-9-yl]-tetrahydrofuran-3,4-diol | Analogous method to route G | TLC SiO$_2$ (C$_{12}$CH$_2$:EtOH:880NH$_3$ 95:5:0.5) R$_f$ = 0.2 Microanalysis Found C, 49.75; H, 5.90; N, 25.2. C$_{18}$H$_{24}$N$_8$O$_5$ requires C, 49.5; H, 5.65; N, 25.6 |
| 59 | (2R,3R,4S,5S)-2-{6-[rel-(1S,2R,4R)-bicyclo[2.2.1]-hept-2-ylamino]-9H-purin-9-yl}-5-(3-cyclopropyl-1,2,4-oxadiazol-5-yl)tetrahydrofuran-3,4-diol | Analogous method to route G | LC/MS (System B) R$_t$ 2.81 min. Mass Spectrum m/z 440 [MH$^+$] |
| 60 | ethyl 4-({9-[(2R,3R,4S,5S)-5-(3-cyclopropyl-1,2,4-oxadiazol-5-yl)-3,4-dihydroxy-tetrahydrofuran-2-yl]-9H-purin-6-yl}amino)-piperidine-1-carboxylate | Analogous method to route G | LC/MS (System B) R$_t$ 2.57 min. Mass Spectrum m/z 501 [MH$^+$] |
| 61 | (2S,3S,4R,5R)-2-[3-(tert-butyl)-1,2,4-oxadiazol-5-yl]-5-[6-(isopropylamino)-9H-purin-9-yl]-tetrahydrofuran-3,4-diol | Analogous method to route G | LC/MS (System B) R$_t$ 2.69 min. Mass Spectrum m/z 404 [MH$^+$] |
| 62 | (2R,3R,4S,5S)-2-[6-(4-chloro-2-fluoroanilino)-9H-purin-9-yl]-5-(3-cyclopropyl-1,2,4-oxadiazol-5-yl)-tetrahydrofuran-3,4-diol | Analogous method to route G | LC/MS (System B) R$_t$ 3.05 min. Mass Spectrum m/z 474 [MH$^+$] |
| 63 | ethyl 4-({9-[(2R,3R,4S,5S)-3,4-dihydroxy-5-(3-isopropyl-1,2,4-oxadiazol-5-yl)-tetrahydrofuran-2-yl]-9H-purin-6-yl}amino)-piperidine-1-carboxylate | Analogous method to route G | LC/MS (System B) R$_t$ 2.73 min. Mass Spectrum m/z 503 [MH$^+$] |
| 64 | (2R,3R,4S,5S)-2-{6-[rel-(1S,2R,4R)-bicyclo[2.2.1]-hept-2-ylamino]-9H-purin-9-yl}-5-(3-isopropyl-1,2,4-oxadiazol-5-yl)-tetrahydrofuran-3,4-diol | Analogous method to route G | LC/MS (System A) R$_t$ 4.27 min. Mass Spectrum m/z 442 [MH$^+$] |
| 65 | 2-({9-[(2R,3R,4S,5S)-5-(3-cyclopropyl-1,2,4-oxadiazol-5-yl)-3,4-dihydroxy-tetrahydrofuran-2-yl]-9H-purin-6- | Analogous method to route G | LC/MS (System B) R$_t$ 2.33 min. Mass Spectrum m/z 467 [MH$^+$] |

TABLE 1-continued

Examples

| Ex No | Name | Expt. Details (note 1) | Characterising data |
|---|---|---|---|
| | yl}amino)-N-methylethane-sulfonamide | | |
| 66 | (2R,3R,4S,5S)-2-[2-Chloro-6-(1-ethyl-propyl-amino)-purin-9-yl]-5-(3-propyl-isoxazol-5-yl)-tetrahydro-furan-3,4-diol formate | Analogous method to route L | LC/MS (System A) R$_t$ 4.68 min. Mass Spectrum m/z 451 [MH$^+$] |
| 67 | (2R,3S,4R,5R)-2-[5-(tert-butyl)-4H-1,2,4-triazol-3-yl]-5-[6-(4-chloro-2-fluoroanilino)-9H-purin-9-yl]-tetrahydrofuran-3,4-diol | Analogous method to route F | LC/MS (System C) R$_t$ 3.01 min. Mass Spectrum m/z 489 [MH$^+$] |
| 68 | (2R,3R,4S,5R)-2-[6-(2-chloro-4-fluoroanilino)-9H-purin-9-yl]-5-(5-isopropyl-4H-1,2,4-triazol-3-yl)-tetrahydrofuran-3,4-diol | Analogous method to route F | LC/MS (System C) R$_t$ 2.89 min. Mass Spectrum m/z 475 [MH$^+$] |
| 69 | 2-({9-[(2R,3R,4S,5S)-3,4-dihydroxy-5-(3-methyl-1,2,4-oxadiazol-5-yl)-tetrahydrofuran-2-yl]-9H-purin-6-yl}amino)-N-methylethane-sulfonamide | Analogous method to route G | Analysis: C$_{15}$H$_{20}$N$_8$O$_6$S Found % C: 40.93, H: 4.72 N: 24.89 Required % C: 40.9, H: 4.63, N: 25.24 M/Z [M + H] 441 |
| 70 | (2R,3R,4S,5S)-2-{6-[(trans-4-hydroxycyclohexyl)amino]-9H-purin-9-yl}-5-(5-methyl-1,3-oxazol-2-yl)tetrahydrofuran-3,4-diol | Analogous method to route D | M/Z [M + H] 417 |
| 71 | (2S,3S,4R,5R)-2-(3-methyl-1,2,4-oxadiazol-5-yl)-5-(6-{[(1R)-1-methyl-2-phenylethyl]-amino}-9H-purin-9-yl)-tetrahydrofuran-3,4-diol | Analogous method to route G | Analysis: C21H23N7O4 Found % C: 56.41, H: 5.32 N: 21.78 Required % C: 56.49, H: 5.42, N: 21.96 |
| 72 | (2S,3S,4R,5R)-2-(5-ethyl-1,3-oxazol-2-yl)-5-{6-[(trans-4-hydroxycyclohexyl)-amino]-9H-purin-9-yl}-tetrahydrofuran-3,4-diol | Analogous method to route D | Analysis: C20H26N6O5 Found % C: 54.5, H: 6.0 N: 18.8 Required % C: 55.8, H: 6.1, N: 19.5 M/Z [M + H] 432 |
| 73 | (2S,3S,4R,5R)-2-(5-ethyl-1,3-oxazol-2-yl)-5-[6-(3-fluoro-4-hydroxyanilino)-9H-purin-9-yl]-tetrahydrofuran-3,4-diol | Analogous method to route D | Analysis: C20H19FN6O5 Found % C: 53.6, H: 4.65 N: 18.1 Required % C: 53.2, H: 4.5, N: 18.6 M/Z [M + H] 443 |

TABLE 1-continued

Examples

| Ex No | Name | Expt. Details (note 1) | Characterising data |
|---|---|---|---|
| 74 | (2R,3R,4S,5S)-2-[6-(3-fluoroanilino)-9H-purin-9-yl]-5-(5-methyl-1,3-oxazol-2-yl)-tetrahydrofuran-3,4-diol | Analogous method to route D | M/Z [M + H] 413 |
| 75 | (2S,3S,4R,5R)-2-(5-ethyl-1,3-oxazol-2-yl)-5-(6-{[(1S,2R)-2-fluorocyclopentyl]-amino}-9H-purin-9-yl)-tetrahydrofuran-3,4-diol | Analogous method to route D | M/Z [M + H] 419 |
| 76 | (2R,3R,4S,5S)-2-[6-(4-fluoroanilino)-9H-purin-9-yl]-5-(5-methyl-1,3-oxazol-2-yl)-tetrahydrofuran-3,4-diol | Analogous to route D. See below (route P) for synthesis of intermediate. | Rf = 0.18 (Dichloromethane: ethanol:880ammonia 100:10:1) M/Z [M + H] 413 |
| 77 | (2S,3S,4R,5R)-2-[3-(tert-butyl)-1,2,4-oxadiazol-5-yl]-5-[6-(tetrahydro-2H-pyran-4-ylamino)-9H-purin-9-yl]-tetrahydrofuran-3,4-diol | Analogous method to route G | LC/MS (System A) Rt2.53 min. Mass Spectrum m/z 446 [MH+]. |
| 78 | (2R,3R,4S,5S)-2-{6-[rel-(1S,2R,4R)-bicyclo[2.2.1]hept-2-ylamino]-9H-purin-9-yl}-5-[3-(tert-butyl)-1,2,4-oxadiazol-5-yl]-tetrahydrofuran-3,4-diol | Analogous method to route G | LC/MS (System A) Rt 3.03 min. Mass Spectrum m/z 456 [MH+]. |
| 79 | ethyl 4-[(9-{(2R,3R,4S,5S)-5-[3-(tert-butyl)-1,2,4-oxadiazol-5-yl]-3,4-dihydroxy-tetrahydrofuran-2-yl}-9H-purin-6-yl)amino]-piperidine-1-carboxylate | Analogous method to route G | LC/MS (System A) Rt 2.77 min. Mass Spectrum m/z 4517 [MH+]. |
| 80 | 2-[(9-{(2R,3R,4S,5S)-5-[3-(tert-butyl)-isoxazol-5-yl]-3,4-dihydroxy-tetrahydrofuran-2-yl}-9H-purin-6-yl)amino]-N-methylethane-sulfonamide | Analogous method to route I | LC/MS (System B) Rt 3.76 min. Mass Spectrum m/z 482 [MH+]. |
| 81 | (2S,3S,4R,5R)-2-[3-(tert-butyl)-isoxazol-5-yl]-5-(6-{[(1S,2S)-2-fluorocyclopentyl]-amino}-9H-purin-9-yl)-tetrahydrofuran-3,4-diol | Analogous method to route I | LC/MS (System B) Rt 4.20 min. Mass Spectrum m/z 447 [MH+]. |

TABLE 1-continued

Examples

| Ex No | Name | Expt. Details (note 1) | Characterising data |
|---|---|---|---|
| 82 | ethyl 4-[(9-{(2R,3R,4S,5S)-5-[3-(tert-butyl)-isoxazol-5-yl]-3,4-dihydroxy-tetrahydrofuran-2-yl}-9H-purin-6-yl)amino]-piperidine-1-carboxylate | Analogous method to route I | LC/MS (System B) Rt 4.06 min. Mass Spectrum m/z 516 [MH+]. |
| 83 | (2S,3S,4R,5R)-2-[3-(tert-butyl)-isoxazol-5-yl]-5-[6-(cyclo-pentylamino)-9H-purin-9-yl]-tetrahydrofuran-3,4-diol | Analogous method to route I | LC/MS (System B) Rt 4.18 min. Mass Spectrum m/z 429 [MH+]. |
| 84 | 2-({9-[(2R,3R,4S,5S)-5-(5-ethyl-1,3-oxazol-2-yl)-3,4-dihydroxy-tetrahydrofuran-2-yl]-9H-purin-6-yl}amino)-N,N-dimethylethane-sulfonamide | See below (route Q). | Mass Spectrum m/z[MH]+ = 468 |
| 85 | 2-({9-[(2R,3R,4S,5S)-5-(5-ethyl-1,3-oxazol-2-yl)-3,4-dihydroxy-tetrahydrofuran-2-yl]-9H-purin-6-yl}amino)-N-methylethane-sulfonamide | Analagous method to route Q. | Mass Spectrum m/z[MH]+ = 454 |
| 86 | ethyl 4-({9-[(2R,3R,4S,5S)-5-(5-ethyl-1,3-oxazol-2-yl)-3,4-dihydroxy-tetrahydrofuran-2-yl]-9H-purin-6-yl}amino)-piperidine-1-carboxylate | Analogous to route Q. | Mass Spectrum m/z[MH]+ = 488 |
| 87 | (2R,3R,4S,5S)-2-{6-[(2,3-dihydroxypropyl)-amino]-9H-purin-9-yl}-5-(5-ethyl-1,3-oxazol-2-yl)-tetrahydrofuran-3,4-diol | Analogous to route Q. | Mass Spectrum m/z[MH]+ = 407 |
| 88 | (2R,3R,4S,5S)-2-[6-(2,4-difluoroanilino)-9H-purin-9-yl]-5-(5-ethyl-1,3-oxazol-2-yl)-tetrahydrofuran-3,4-diol | Analogous to route Q. | Mass Spectrum m/z[MH]+ = 445 |
| 89 | (2S,3S,4R,5R)-2-(5-ethyl-1,3-oxazol-2-yl)-5-(6-{[(1S,2S)-2-hydroxy-cyclopentyl]-amino}-9H-purin-9-yl)-tetrahydrofuran-3,4-diol | Analogous to route Q. | Mass Spectrum m/z[MH]+ = 417 |

TABLE 1-continued

Examples

| Ex No | Name | Expt. Details (note 1) | Characterising data |
|---|---|---|---|
| 90 | (2S,3S,4R,5R)-2-(5-ethyl-1,3-oxazol-2-yl)-5-{6-[(3R)-tetrahydrofuran-3-ylamino]-9H-purin-9-yl}tetrahydrofuran-3,4-diol | Analagous to route Q. | Mass Spectrum m/z[MH]+ = 403 |
| 91 | (2R,3R,4S,5S)-2-(6-{[(1R)-2-methoxy-1-methylethyl]-amino}-9H-purin-9-yl)-5-(5-methyl-1,3,4-oxadiazol-2-yl)-tetrahydrofuran-3,4-diol | Analagous method to route C | Microanalysis Found: C, 46.7; H, 5.3; N, 23.6. $C_{16}H_{21}N_7O_5$ requires: C, 46.9; H, 5.7; N, 23.95. |
| 92 | (2R,3R,4S,5S)-2-[6-(cyclopentylamino)-9H-purin-9-yl]-5-(3-methyl-1,2,4-oxadiazol-5-yl)-tetrahydrofuran-3,4-diol | See below (route R). | TLC $SiO_2$ (ethyl acetate:methanol 19:1) Rf = 0.30 NMR (DMSO) 8.43 (1H,s,CH); 8.20 (1H,br.s,CH); 7.79 (1H,br.d,NH); 6.45 (2H,v.br.s,2x OH); 6.16 (1H,d,CH); 5.24 (1H,d,CH); 4.89 (1H,t,CH); 4.73 (1H,t,CH); 4.58 (1H,br.m,CH); 2.42 (3H,s,Me); 2.10-1.50 (8H,m,4xCH$_2$) |
| 93 | (2R,3R,4S,5S)-2-(6-{[(1R,2R)-2-hydroxy-cyclopentyl]-amino}-9H-purin-9-yl)-5-(5-phenyl-1,3,4-oxadiazol-2-yl)-tetrahydrofuran-3,4-diol | Analagous method to route A | TLC $SiO_2$ ($CH_2Cl_2$:MeOH:880$NH_3$ 92:8:0.3) Rf = 0.14 Microanalysis Found: C, 55.7; H, 5.1; N, 20.5. $C_{22}H_{23}N_7O_5$ requires: C, 55.7; H, 5.1; N, 20.7 |
| 94 | (2R,3R,4S,5S)-2-{6-[rel-(1S,5S,6R)-bicyclo[3.2.0]-hept-6-ylamino]-9H-purin-9-yl}-5-(3-methyl-1,2,4-oxadiazol-5-yl)-tetrahydrofuran-3,4-diol | Analagous method to route G | Microanalysis Found: C, 54.2; H, 5.7; N, 22.65. $C_{19}H_{23}N_7O_4$. 0.5MeOH requires: C, 54.5; H, 5.9; N, 22.8. |
| 95 | (2R,3R,4S,5S)-2-{6-[rel-(1S,2S,4R)-bicyclo[2.2.1]-hept-2-ylamino]-9H-purin-9-yl}-5-(3-methyl-1,2,4-oxadiazol-5-yl)tetrahydrofuran-3,4-diol | Analagous method to route G | Microanalysis Found: C, 54.4; H, 5.7; N, 23.1. $C_{19}H_{23}N_7O_4$. 0.4$H_2O$ requires: C, 54.25; H, 5.7; N, 23.3. |
| 96 | (2R,3R,4S,5S)-2-{6-[rel-(1S,2R,4R)-bicyclo[2.2.1]-hept-2-ylamino]-9H-purin-9-yl}-5-[5-(tert-butyl)-1,3,4-oxadiazol-2-yl]tetrahydrofuran-3,4-diol | Analagous method to route A | LC/MS (System B) $R_t$ = 3.18 min Mass Spectrum m/z 544 [MH$^+$] |

TABLE 1-continued

Examples

| Ex No | Name | Expt. Details (note 1) | Characterising data |
|---|---|---|---|
| 97 | (2R,3R,4S,5S)-2-{6-[rel-(1S,2R,4R)-bicyclo[2.2.1]-hept-2-ylamino]-9H-purin-9-yl}-5-(5-isopropyl-1,3,4-oxadiazol-2-yl)-tetrahydrofuran-3,4-diol | Analagous method to route A | LC/MS (System B) $R_t$ = 2.66 min Mass Spectrum m/z 442 [MH$^+$] |
| 98 | ethyl 4-({9-[(2R,3R,4S,5S)-3,4-dihydroxy-5-(5-isopropyl-1,3,4-oxadiazol-2-yl)-tetrahydrofuran-2-yl]-9H-purin-6-yl}amino)-piperidine-1-carboxylate | Analagous method to route A | LC/MS (System B) $R_t$ = 2.47 min Mass Spectrum m/z 503 [MH$^+$] |
| 99 | 2-[(9-{(2R,3R,4S,5S)-5-[5-(tert-butyl)-1,3,4-oxadiazol-2-yl]-3,4-dihydroxy-tetrahydrofuran-2-yl}-9H-purin-6-yl)amino]-N-methylethane-sulfonamide | Analagous method to route A | LC/MS (System B) $R_t$ = 2.32 min Mass Spectrum m/z 483 [MH$^+$] |
| 100 | (2S,3S,4R,5R)-2-[5-(tert-butyl)-1,3,4-oxadiazol-2-yl]-5-(6-{[(1R,2R)-2-fluorocyclopentyl]-amino}-9H-purin-9-yl)-tetrahydrofuran-3,4-diol | Analagous method to route A | LC/MS (System B) $R_t$ = 2.63 min Mass Spectrum m/z 448 [MH$^+$] |
| 101 | (2S,3S,4R,5R)-2-[3-(tert-butyl)-1,2,4-oxadiazol-5-yl]-5-[6-(tetrahydro-2H-pyran-4-ylamino)-9H-purin-9-yl]-tetrahydrofuran-3,4-diol | Analagous to route G | LC/MS (System B) $R_t$ = 2.53 min Mass Spectrum m/z 446 [MH$^+$] |
| 102 | (2R,3R,4S,5S)-2-{6-[rel-(1S,2R,4R)-bicyclo[2.2.1]-hept-2-ylamino]-9H-purin-9-yl}-5-[3-(tert-butyl)-1,2,4-oxadiazol-5-yl]-(tetrahydrofuran-3,4-diol | Analagous to route G | LC/MS (System B) $R_t$ = 3.03 min Mass Spectrum m/z 456 [MH$^+$] |
| 103 | ethyl 4-[(9-{(2R,3R,4S,5S)-5-[3-(tert-butyl)-1,2,4-oxadiazol-5-yl]-3,4-dihydroxy-tetrahydrofuran-2-yl}-9H-purin-6-yl)amino]-piperidine-1-carboxylate | Analagous to route G | LC/MS (System B) $R_t$ = 2.77 min Mass Spectrum m/z 517 [MH$^+$] |
| 104 | 2-[(9-{(2R,3R,4S,5S)-5-[3-(tert- | Analagous to route I | LC/MS (System A) $R_t$ = 3.76 min Mass Spectrum |

TABLE 1-continued

Examples

| Ex No | Name | Expt. Details (note 1) | Characterising data |
|---|---|---|---|
| | butyl)isoxazol-5-yl]-3,4-dihydroxy-tetrahydrofuran-2-yl}-9H-purin-6-yl)amino]-N-methylethane-sulfonamide | | m/z 482 [MH⁺] |
| 105 | (2S,3S,4R,5R)-2-[3-(tert-butyl)isoxazol-5-yl]-5-(6-{[(1S,2S)-2-fluorocyclopentyl]-amino}-9H-purin-9-yl) tetrahydrofuran-3,4-diol | Analagous to route I | LC/MS (System A) $R_t$ = 4.20 min Mass Spectrum m/z 447 [MH⁺] |
| 106 | ethyl 4-[(9-{(2R,3R,4S,5S)-5-[3-(tert-butyl)isoxazol-5-yl]-3,4-dihydroxy-tetrahydrofuran-2-yl}-9H-purin-6-yl)amino]-piperidine-1-carboxylate | Analagous to route I | LC/MS (System A) $R_t$ = 4.06 min Mass Spectrum m/z 516 [MH⁺] |
| 107 | (2S,3S,4R,5R)-2-[3-(tert-butyl)isoxazol-5-yl]-5-[6-(cyclo-pentylamino)-9H-purin-9-yl]-tetrahydrofuran-3,4-diol | Analagous to route I | LC/MS (System A) $R_t$ = 4.18 min Mass Spectrum m/z 429 [MH⁺] |
| 108 | (2S,3S,4R,5R)-2-(5-cyclopropyl-1,3,4-oxadiazol-2-yl)-5-[6-(tetrahydro-2H-pyran-4-ylamino)-9H-purin-9-yl]-tetrahydrofuran-3,4-diol | Analagous to route A | LC/MS (System D) $R_t$ = 2.28 min Mass Spectrum m/z 430 [MH⁺] |
| 109 | (2S,3S,4R,5R)-2-(5-cyclopentyl-1,3,4-oxadiazol-2-yl)-5-(6-{[(1S,2S)-2-hydroxy-cyclopentyl]-amino}-9H-purin-9-yl)-tetrahydrofuran-3,4-diol | Analagous to route A | LC/MS (System D) $R_t$ = 2.59 min Mass Spectrum m/z 458 [MH⁺] |
| 110 | ethyl 4-({9-[(2R,3R,4S,5S)-5-(5-cyclopentyl-1,3,4-oxadiazol-2-yl)-3,4-dihydroxy-tetrahydrofuran-2-yl]-9H-purin-6-yl}amino)-piperidine-1-carboxylate | Analagous to route A | LC/MS (System D) $R_t$ = 2.82 min Mass Spectrum m/z 529 [MH⁺] |
| 111 | (2S,3S,4R,5R)-2-(5-cyclopentyl-1,3,4-oxadiazol-2-yl)-5-(6-{[(1R,2R)-2-fluorocyclopentyl]-amino}-9H-purin-9-yl)- | Analagous to route A | LC/MS (System D) $R_t$ = 2.93 min Mass Spectrum m/z 460 [MH⁺] |

TABLE 1-continued

Examples

| Ex No | Name | Expt. Details (note 1) | Characterising data |
|---|---|---|---|
| | tetrahydrofuran-3,4-diol | | |
| 112 | (2R,3R,4S,5S)-2-[6-(4-chloro-2-fluoroanilino)-9H-purin-9-yl]-5-(5-cyclopropyl-1,3,4-oxadiazol-2-yl)-tetrahydrofuran-3,4-diol | Analogous to route A | LC/MS (System B) $R_t$ = 2.84 min Mass Spectrum m/z 474 [MH$^+$] |
| 113 | (2R,3R,4S,5S)-2-[6-(4-chloro-2-fluoroanilino)-9H-purin-9-yl]-5-(5-cyclopentyl-1,3,4-oxadiazol-2-yl)-tetrahydrofuran-3,4-diol | Analogous to route A | LC/MS (System B) $R_t$ = 3.05 min Mass Spectrum m/z 502 [MH$^+$] |
| 114 | (2S,3S,4R,5R)-2-[5-(tert-butyl)-1,3,4-oxadiazol-2-yl]-5-[6-(2-fluoroanilino)-9H-purin-9-yl]-tetrahydrofuran-3,4-diol | Analogous to route A | LC/MS (System D) $R_t$ = 2.88 min Mass Spectrum m/z 456 [MH$^+$] |
| 115 | (2S,3S,4R,5R)-2-[5-(tert-butyl)-1,3,4-oxadiazol-2-yl]-5-[6-(2,3-difluoroanilino)-9H-purin-9-yl]-tetrahydrofuran-3,4-diol | Analogous to route A | LC/MS (System D) $R_t$ = 2.96 min Mass Spectrum m/z 474 [MH$^+$] |
| 116 | (2S,3S,4R,5R)-2-[5-(tert-butyl)-1,3,4-oxadiazol-2-yl]-5-[6-(2-chloro-4-fluoroanilino)-9H-purin-9-yl]-tetrahydrofuran-3,4-diol | Analogous to route A | LC/MS (System D) $R_t$ = 3.05 min Mass Spectrum m/z 490 [MH$^+$] |
| 117 | (2S,3S,4R,5R)-2-[5-(tert-butyl)-1,3,4-oxadiazol-2-yl]-5-[6-(4-fluoro-2-methylanilino)-9H-purin-9-yl]-tetrahydrofuran-3,4-diol | Analogous to route A | LC/MS (System D) $R_t$ = 2.86 min Mass Spectrum m/z 470 [MH$^+$] |
| 118 | (2R,3R,4S,5R)-2-{2-chloro-6-[(1-ethylpropyl)-amino]-9H-purin-9-yl}-5-(5-ethyl isoxazol-3-yl)-tetrahydrofuran-3,4-diol formate | See below (route S). | LC/MS (System C) $R_t$ = 3.41 min Mass Spectrum m/z 437 [MH$^+$] |
| 119 | (2S,3S,4R,5R)-2-[3-(tert-butyl)isoxazol-5-yl]-5-{6-[(1,1-dioxidotetrahydro-2H-thiopyran-4-yl)amino]-9H-purin-9-yl}-tetrahydrofuran-3,4-diol | Analogous to route I (last 2 steps reverse order) | LC/MS (System C) $R_t$ = 2.61 min Mass Spectrum m/z 493 [MH$^+$] |
| 120 | (2S,3S,4R,5R)-2-[3-(tert-butyl)isoxazol-5-yl]-5-[6-(2- | Analogous to route I (last 2 steps reverse order) | LC/MS (System C) $R_t$ = 3.29 min Mass Spectrum m/z 489/491 [MH$^+$] |

TABLE 1-continued

Examples

| Ex No | Name | Expt. Details (note 1) | Characterising data |
|---|---|---|---|
| | chloro-4-fluoroanilino)-9H-purin-9-yl]-tetrahydrofuran-3,4-diol | | |
| 121 | (2S,3S,4R,5R)-2-[3-(tert-butyl)isoxazol-5-yl]-5-[6-(4-fluoro-2-methylanilino)-9H-purin-9-yl]-tetrahydrofuran-3,4-diol | Analagous to route I (last 2 steps reverse order) | LC/MS (System C) $R_t$ = 3.09 min Mass Spectrum m/z 469 [MH$^+$] |
| 122 | (2S,3S,4R,5R)-2-[3-(tert-butyl)isoxazol-5-yl]-5-[6-(2-chloroanilino)-9H-purin-9-yl]-tetrahydrofuran-3,4-diol | Analagous to route I (last 2 steps reverse order) | LC/MS (System C) $R_t$ = 3.25 min Mass Spectrum m/z 471/473 MH$^+$] |
| 123 | 2-[(9-{(2R,3R,4S,5S)-5-[5-(tert-butyl)-1,3,4-oxadiazol-2-yl]-3,4-dihydroxy-tetrahydrofuran-2-yl}-9H-purin-6-yl)amino]-N-ethylethane-sulfonamide | Analagous to route T | LC/MS (System C) $R_t$ 2.52 min. Mass Spectrum m/z 497 [MH$^+$]. |
| 124 | (2S,3S,4R,5R)-2-[5-(tert-butyl)-1,3,4-oxadiazol-2-yl]-5-(6-{[2-(ethylsulfonyl)-ethyl]amino}-9H-purin-9-yl)-tetrahydrofuran-3,4-diol | Analagous to route A | LC/MS (System C) $R_t$ 2.45 min. Mass Spectrum m/z 482 [MH$^+$]. |
| 125 | (2S,3S,4R,5R)-2-[5-(tert-butyl)-1,3,4-oxadiazol-2-yl]-5-(6-{[2-(butylsulfonyl)-ethyl]amino}-9H-purin-9-yl)tetrahydrofuran-3,4-diol | Analagous to route A | LC/MS (System C) $R_t$ 2.6 min. Mass Spectrum m/z 510 [MH$^+$]. |
| 126 | 2-[(9-{(2R,3R,4S,5S)-5-[5-(tert-butyl)-1,3,4-oxadiazol-2-yl]-3,4-dihydroxy-tetrahydrofuran-2-yl}-9H-purin-6-yl)amino]-N-(3-methylphenyl)-ethanesulfonamide | Analagous to route A | LC/MS (System C) $R_t$ 2.79 min. Mass Spectrum m/z 559 [MH$^+$]. |
| 127 | 2-({9-[(2R,3R,4S,5S)-3,4-dihydroxy-5-(5-methyl-1,3-oxazol-2-yl)-tetrahydrofuran-2-yl]-9H-purin-6-yl}amino)-N-methylethane-sulfonamide | Route V | Mass Spectrum m/z 440 [MH$^+$]. TLC SiO$_2$ (dichloromethane: ethanol:ammonia 50:8:1) R$_f$ 0.21. |
| 128 | 2-[(9-{(2R,3R,4S,5S)-5-[5-(tert-butyl)-1,3,4-oxadiazol-2- | Analagous to route A | LC/MS (System C) $R_t$ 2.7 min. Mass Spectrum m/z 545 [MH$^+$]. |

TABLE 1-continued

Examples

| Ex No | Name | Expt. Details (note 1) | Characterising data |
|---|---|---|---|
| | yl]-3,4-dihydroxy-tetrahydrofuran-2-yl}-9H-purin-6-yl)amino]-N-phenylethane-sulfonamide | | |
| 129 | (2R,3R,4S,5S)-2-[6-(cyclo-pentylamino)-9H-purin-9-yl]-5-[3-(methoxy-methyl)-1,2,4-oxadiazol-5-yl]-tetrahydrofuran-3,4-diol | Analogous to route G | Analysis: Found (%):C 49.5; H 5.4; N 21.9. Required for $C_{18}H_{23}N_7O_5$. 1.2 $H_2O$ C 49.3; H 5.8; N 22.3. |
| 130 | (2R,3R,4S,5R)-2-[6-(cyclo-pentylamino)-9H-purin-9-yl]-5-(1,5-dimethyl-1H-1,2,4-triazol-3-yl)-tetrahydrofuran-3,4-diol trifluoroacetate | Route X | Analysis: Found (%):C 44.4; H 4.8; N 20.4. Required for $C_{18}H_{24}N_8O_3 \cdot CF_3CO_2H \cdot 1.5 H_2O$ C 44.4; H 5.2; N 20.7. |
| 131 | (2S,3S,4R,5R)-2-(5-ethyl-1,3,4-oxadiazol-2-yl)-5-[6-(isopropylamino)-9H-purin-9-yl]-tetrahydrofuran-3,4-diol | From Intermediate 17, analagous to route C | Analysis: Found (%):C 50.0; H 5.7; N 24.7. $C_{16}H_{21}N_7O_4 \cdot 0.1$ $CH_2Cl_2$. 0.1 $H_2O$ requires C 50.1; H 5.6; N 25.4. TLC $SiO_2$ (dichloromethane: methanol:ammonia 94:6:1) $R_f$ 0.21. |
| 132 | (2R,3R,4S,5S)-2-(6-{[(1S,2S)-2-hydroxy-cyclopentyl]-amino}-9H-purin-9-yl)-5-(5-methyl-1,3,4-oxadiazol-2-yl)-tetrahydrofuran-3,4-diol | Analagous to route A | Analysis: Found (%):C 48.9; H 5.4; N 21.8. $C_{17}H_{21}N_7O_5 \cdot 0.9 H_2O$. 0.4EtOAc requires C 49.1; H 5.8; N 21.6. TLC $SiO_2$(ethyl acetate:methanol 7:1) $R_f$ 0.45. |
| 133 | (2S,3S,4R,5R)-2-[3-(methyl)-1,2,4-oxadiazol-5-yl]-5-[6-(2-chloro-4-fluoroanilino)-9H-purin-9-yl]-tetrahydrofuran-3,4-diol | Analagous to route G | LC/MS (System C) $R_t$ 2.91 min. Mass Spectrum m/z 448 [MH$^+$]. |
| 134 | (2R,3R,4S,5S)-2-{2-chloro-6-[(1-ethylpropyl)-amino]-9H-purin-9-yl}-5-(3-cyclopropyl-1,2,4-oxadiazol-5-yl)-tetrahydrofuran-3,4-diol formate (1:2) | Analagous to routes B and R | LC/MS (System C) $R_t$ 3.22 min. Mass Spectrum m/z 450 [MH$^+$]. |
| 135 | (2S,3S,4R,5R)-2-(3-ethylisoxazol-5-yl)-5-[6-(tetrahydro-2H-pyran-4-ylamino)-9H-purin-9-yl]-tetrahydrofuran-3,4-diol | Analagous to route L | LC/MS (System C) $R_t$ 2.46 min. Mass Spectrum m/z 417 [MH$^+$]. |

TABLE 1-continued

Examples

| Ex No | Name | Expt. Details (note 1) | Characterising data |
|---|---|---|---|
| 136 | (2S,3S,4R,5R)-2-(3-ethylisoxazol-5-yl)-5-(6-{[(1S,2S)-2-hydroxycyclopentyl]amino}-9H-purin-9-yl]-tetrahydrofuran-3,4-diol | Analagous to route L | LC/MS (System C) $R_t$ 2.51 min. Mass Spectrum m/z 417 [MH$^+$]. |
| 137 | N-ethyl-2-({9-[(2R,3R,4S,5S)-5-(3-ethylisoxazol-5-yl)-3,4-dihydroxytetrahydrofuran-2-yl]-9H-purin-6-yl}amino)ethanesulfonamide | Analagous to route L | LC/MS (System C) $R_t$ 2.53 min. Mass Spectrum m/z 468 [MH$^+$]. |
| 138 | ethyl 4-({9-[(2R,3R,4S,5S)-5-(3-ethylisoxazol-5-yl)-3,4-dihydroxytetrahydrofuran-2-yl]-9H-purin-6-yl}amino)-piperidine-1-carboxylate | Analagous to route L | LC/MS (System C) $R_t$ 2.74 min. Mass Spectrum m/z 488 [MH$^+$]. |
| 139 | (2R,3S,4R,5R)-2-[5-(tert-butyl)-4H-1,2,4-triazol-3-yl]-5-[6-(tetrahydro-2H-pyran-4-ylamino)-9H-purin-9-yl]-tetrahydrofuran-3,4-diol | Analagous to route F | LC/MS (System C) $R_t$ 2.30 min. Mass Spectrum m/z 445 [MH$^+$]. |
| 140 | (2R,3R,4S,5R)-2-[6-(4-chloro-2-fluoroanilino)-9H-purin-9-yl]-5-(4H-1,2,4-triazol-3-yl)-tetrahydrofuran-3,4-diol | Analagous to route F | LC/MS (System C) $R_t$ 2.47 min. Mass Spectrum m/z 433 [MH$^+$]. |
| 141 | (2R,3S,4R,5R)-2-(5-isopropyl-4H-1,2,4-triazol-3-yl)-5-[6-(tetrahydro-2H-pyran-4-ylamino)-9H-purin-9-yl]-tetrahydrofuran-3,4-diol | Analagous to route F | LC/MS (System C) $R_t$ 2.21 min. Mass Spectrum m/z 431 [MH$^+$]. |
| 142 | (2R,3R,4S,5S)-2-(6-amino-2-chloro-9H-purin-9-yl)-5-(5-methyl-1,3-oxazol-2-yl)-tetrahydrofuran-3,4-diol | Analagous to route Q | Analysis: Found (%):C 43.73; H 3.32; N 23.04. $C_{13}H_{13.1}N_5O_4Cl.0.1$ $CF_3CO_2H$). requires C 43.54; H 3.63; N 23.08. Mass Spectrum m/z 353 [MH$^+$]. |
| 143 | (2R,3R,4S,5S)-2-[2-chloro-6-(2-chloro-4-fluoroanilino)-9H-purin-9-yl]-5-(5-methyl-1,3-oxazol-2-yl)-tetrahydrofuran-3,4-diol | Analagous to route Q | LC/MS (System C) $R_t$ 3.19 min. Mass Spectrum m/z 482 [MH$^+$]. |

TABLE 1-continued

Examples

| Ex No | Name | Expt. Details (note 1) | Characterising data |
|---|---|---|---|
| 144 | (2R,3R,4S,5S)-2-[6-(4-chloro-2-fluoroanilino)-9H-purin-9-yl]-5-(3-methylisoxazol-5-yl)-tetrahydrofuran-3,4-diol | Route Wb | LC/MS (System C) $R_t$ 2.95 min. Mass Spectrum m/z 447 [MH$^+$]. |
| 145 | (2R,3R,4S,5S)-2-[6-(4-chloro-2-fluoroanilino)-9H-purin-9-yl]-5-(3-propylisoxazol-5-yl)-tetrahydrofuran-3,4-diol | Analogous to route Wb | LC/MS (System C) $R_t$ 3.23 min. Mass Spectrum m/z 475 [MH$^+$]. |
| 146 | 2-[(9-{(2R,3R,4S,5S)-5-[3-(tert-butyl)isoxazol-5-yl]-3,4-dihydroxy-tetrahydrofuran-2-yl}-9H-purin-6-yl)amino]-N-isopropylethane-sulfonamide | Analogous to route I | LC/MS (System C) $R_t$ 32.75 min. Mass Spectrum m/z 510 [MH$^+$]. |
| 147 | (2R,3R,4S,5S)-2-[2-chloro-6-(tetrahydro-2H-pyran-4-ylamino)-9H-purin-9-yl]-5-(3-ethylisoxazol-5-yl)-tetrahydrofuran-3,4-diol | Analogous to route L | LC/MS (System C) $R_t$ 2.83 min. Mass Spectrum m/z 451/453 [MH$^+$]. |
| 148 | ethyl 4-({2-chloro-9-[(2R,3R,4S,5S)-5-(3-ethyl isoxazol-5-yl)-3,4-dihydroxy-tetrahydrofuran-2-yl]-9H-purin-6-yl}amino)-piperidine-1-carboxylate | Analogous to route L | LC/MS (System C) $R_t$ 3.10 min. Mass Spectrum m/z 522/524 [MH$^+$]. |
| 149 | (2R,3R,4S,5S)-2-(2-chloro-6-{[(1S,2S)-2-hydroxy-cyclopentyl]-amino}-9H-purin-9-yl)-5-(3-ethyl isoxazol-5-yl]tetrahydrofuran-3,4-diol | Analogous to route L | LC/MS (System C) $R_t$ 2.81 min. Mass Spectrum m/z 451/453 [MH$^+$]. |
| 150 | (2R,3R,4S,5S)-2-(2-chloro-6-{[2-(ethylsulfonyl)-ethyl]amino}-9H-purin-9-yl)-5-(3-ethylisoxazol-5-yl)-tetrahydrofuran-3,4-diol | Analogous to route L | LC/MS System C $R_t$ 2.75 min. Mass Spectrum m/z 487/489 [MH$^+$]. |
| 151 | (2R,3R,4S,5S)-2-[2-chloro-6-(4-chloro-2-fluoroanilino)-9H-purin-9-yl]-5-(3-ethylisoxazol-5-yl)-tetrahydrofuran-3,4-diol | Analogous to route L | LC/MS (System C) $R_t$ 3.33 min. Mass Spectrum m/z 495/497 [MH$^+$]. |

TABLE 1-continued

Examples

| Ex No | Name | Expt. Details (note 1) | Characterising data |
|---|---|---|---|
| 152 | (2R,3R,4S,5S)-2-[2-chloro-6-(2-chloro-4-fluoroanilino)-9H-purin-9-yl]-5-(3-ethylisoxazol-5-yl)-tetrahydrofuran-3,4-diol | Analogous to route L | LC/MS (System C) $R_t$ 3.23 min. Mass Spectrum m/z 495 [MH$^+$]. |
| 153 | (2R,3R,4S,5S)-2-[2-chloro-6-(2-fluoroanilino)-9H-purin-9-yl]-5-(3-ethylisoxazol-5-yl)-tetrahydrofuran-3,4-diol | Analogous to route L | LC/MS (System C) $R_t$ 3.08 min. Mass Spectrum m/z 461/463 [MH$^+$]. |
| 154 | (2R,3R,4S,5S)-2-[2-chloro-6-(2-chloroanilino)-9H-purin-9-yl]-5-(3-ethylisoxazol-5-yl)-tetrahydrofuran-3,4-diol | Analogous to route L | LC/MS (System C) $R_t$ 3.22 min. Mass Spectrum m/z 477 [MH$^+$]. |
| 155 | (2R,3R,4S,5S)-2-(6-{[(1S,2S)-2-hydroxy-cyclopentyl]amino}-9H-purin-9-yl)-5-[3-(hydroxymethyl)-isoxazol-5-yl]-tetrahydrofuran-3,4-diol | Analogous to route V | LC/MS (System C) $R_t$ 2.25 min Mass Spectrum m/z 419 [MH$^+$]. |
| 156 | ethyl 4-[(9-{(2R,3R,4S,5S)-3,4-dihydroxy-5-[3-(hydroxymethyl)-isoxazol-5-yl]tetrahydrofuran-2-yl}-9H-purin-6-yl)amino]-piperidine-1-carboxylate | Analogous to route V | LC/MS (System C) $R_t$ 2.46 min. Mass Spectrum m/z 490 [MH$^+$]. |
| 157 | (2S,3S,4R,5R)-2-[3-(hydroxymethyl)-isoxazol-5-yl]-5-[6-(tetrahydro-2H-pyran-4-ylamino)-9H-purin-9-yl]-tetrahydrofuran-3,4-diol | Analogous to route V | LC/MS (System C) $R_t$ 2.20 min. Mass Spectrum m/z 419 [MH$^+$]. |
| 158 | (2R,3R,4S,5S)-2-[6-(4-chloro-2-fluoroanilino)-9H-purin-9-yl]-5-(3-ethylisoxazol-5-yl)-tetrahydrofuran-3,4-diol | Analogous to route L | LC/MS (System C) $R_t$ 3.10 min. Mass Spectrum m/z 461 [MH$^+$]. |
| 159 | (2R,3R,4S,5S)-2-[6-(2-chloro-4-fluoroanilino)-9H-purin-9-yl]-5-(3-ethylisoxazol-5-yl)-tetrahydrofuran-3,4-diol | Analogous to route L | LC/MS (System C) $R_t$ 2.99 min. Mass Spectrum m/z 461 [MH$^+$]. |
| 160 | (2S,3S,4R,5R)-2-(3-ethylisoxazol-5-yl)-5-[6-(2-fluoroanilino)-9H-purin-9-yl]- | Analogous to route L | LC/MS (System C) $R_t$ 2.81 min. Mass Spectrum m/z 427 [MH$^+$]. |

TABLE 1-continued

Examples

| Ex No | Name | Expt. Details (note 1) | Characterising data |
|---|---|---|---|
| | tetrahydrofuran-3,4-diol | | |
| 161 | (2R,3R,4S,5S)-2-[6-(2-chloroanilino)-9H-purin-9-yl]-5-(3-ethylisoxazol-5-yl)-tetrahydrofuran-3,4-diol | Analogous to route L | LC/MS (System C) R$_t$ 2.98 min. Mass Spectrum m/z 443 [MH$^+$]. |
| 162 | (2S,3S,4R,5R)-2-[5-(tert-butyl)-1,3,4-oxadiazol-2-yl]-5-[6-(piperidin-4-ylamino)-9H-purin-9-yl]-tetrahydrofuran-3,4-diol | Analogous to route Y | LC/MS (System C) R$_t$ 2.11 min. Mass Spectrum m/z 445 [MH$^+$]. |
| 163 | (2R,3R,4S,5R)-2-{2-chloro-6-[(1-ethylpropyl)-amino]-9H-purin-9-yl}-5-(5-ethyl isoxazol-3-yl)-tetrahydrofuran-3,4-diol formate | Route S | LC/MS (System C) R$_t$ 3.41 min. Mass Spectrum m/z 437 [MH+]. |
| 164 | (2S,3S,4R,5R)-2-(3-bromoisoxazol-5-yl)-5-[6-(4-chloro-2-fluoroanilino)-9H-purin-9-yl]-tetrahydrofuran-3,4-diol | Route W | LC/MS (System C) R$_t$ 3.22 min. Mass Spectrum m/z 511 [MH$^+$]. |
| 165 | (2R,3R,4S,5S)-2-[6-(4-chloro-2-fluoroanilino)-9H-purin-9-yl]-5-[3-(3,5-difluorophenyl)-isoxazol-5-yl]-tetrahydrofuran-3,4-diol | Analagous to route W | LC/MS (System C) R$_t$ 3.55 min. Mass Spectrum m/z 545 [MH$^+$]. |
| 166 | (2S,3S,4R,5R)-2-[3-(tert-butyl)isoxazol-5-yl]-5-(6-{[1-(methylsulfonyl)-piperidin-4-yl]amino}-9H-purin-9-yl)-tetrahydrofuran-3,4-diol | Analogous to Route Y | LC/MS (System C) R$_t$ 2.69 min. Mass Spectrum m/z 522 [MH$^+$] |
| 167 | (2S,3S,4R,5R)-2-[3-(tert-butyl)isoxazol-5-yl]-5-(6-{[1-(propylsulfonyl)-piperidin-4-yl]amino}-9H-purin-9-yl)-tetrahydrofuran-3,4-diol | Analogous to Route Y | LC/MS (System C) R$_t$ 2.90 min. Mass Spectrum m/z 550 [MH$^+$] |
| 168 | (2S,3S,4R,5R)-2-[3-(tert-butyl)isoxazol-5-yl]-5-(6-{[1-(isopropyl-sulfonyl)-piperidin-4-yl]amino}-9H-purin-9-yl)- | Analogous to Route Y | LC/MS (System C) R$_t$ 2.87 min. Mass Spectrum m/z 550 [MH$^+$] |

TABLE 1-continued

Examples

| Ex No | Name | Expt. Details (note 1) | Characterising data |
|---|---|---|---|
| 169 | tetrahydrofuran-3,4-diol (2S,3S,4R,5R)-2-[3-(tert-butyl)isoxazol-5-yl]-5-(6-{[1-(ethylsulfonyl)-piperidin-4-yl]amino}-9H-purin-9-yl)-tetrahydrofuran-3,4-diol | Analogous to Route Y | LC/MS (System C) $R_t$ 2.77 min. Mass Spectrum m/z 536 [MH$^+$] |
| 170 | (2S,3S,4R,5R)-2-[3-(tert-butyl)isoxazol-5-yl]-5-[2-chloro-6-(4-chloro-2-fluoroanilino)-9H-purin-9-yl]-tetrahydrofuran-3,4-diol | Analogous to Route I | LC/MS (System C) $R_t$ 3.60 min. Mass Spectrum m/z 524 [MH$^+$] |
| 171 | (2S,3S,4R,5R)-2-[3-(tert-butyl)isoxazol-5-yl]-5-[2-chloro-6-(2-chloro-4-fluoroanilino)-9H-purin-9-yl]-tetrahydrofuran-3,4-diol | Analogous to Route I | LC/MS (System C) $R_t$ 3.50 min. Mass Spectrum m/z 524 [MH$^+$] |
| 172 | 2-[(9-{(2R,3R,4S,5S)-5-[3-(tert-butyl)isoxazol-5-yl]-3,4-dihydroxy-tetrahydrofuran-2-yl}-2-chloro-9H-purin-6-yl)amino]-N-ethylethane-sulfonamide | Analogous to Route I | LC/MS (System C) $R_t$ 2.94 min. Mass Spectrum m/z 530 [M$^+$] |
| 173 | 2-[(9-{(2R,3R,4S,5S)-5-[3-(tert-butyl)isoxazol-5-yl]-3,4-dihydroxy-tetrahydrofuran-2-yl}-2-chloro-9H-purin-6-yl)amino]-N-isopropyl-ethanesulfonamide | Analogous to Route I | LC/MS (System C) $R_t$ 3.04 min. Mass Spectrum m/z 544 [M$^+$] |
| 174 | (2S,3S,4R,5R)-2-[3-(tert-butyl)isoxazol-5-yl]-5-[2-chloro-6-(tetrahydro-2H-pyran-4-ylamino)-9H-purin-9-yl]tetrahydrofuran-3,4-diol | Analogous to Route I | LC/MS (System C) $R_t$ 2.96 min. Mass Spectrum m/z 479 [MH$^+$] |
| 175 | (2R,3R,4S,5S)-2-[6-(4-chloro-2-fluoroanilino)-9H-purin-9-yl]-5-(3-pyridin-3-yl)isoxazol-5-yl)-tetrahydrofuran-3,4-diol | Analogous to Route W | LC/MS (System C) $R_t$ 3.02 min. Mass Spectrum m/z 510 [MH$^+$] |
| 176 | (2R,3R,4S,5S)-2-[6-(4-chloro-2-fluoroanilino)-9H-purin-9-yl]-5-[3-(4-hydroxybutyl)-isoxazol-5-yl] | Analogous to Route W | LC/MS (System C) $R_t$ 3.35 min. Mass Spectrum m/z 505 [MH$^+$] |

TABLE 1-continued

Examples

| Ex No | Name | Expt. Details (note 1) | Characterising data |
|---|---|---|---|
| | tetrahydrofuran-3,4-diol | | |
| 177 | 2-[(9-{(2R,3R,4S,5S)-5-[3-(tert-butyl)isoxazol-5-yl]-3,4-dihydroxy-tetrahydrofuran-2-yl}-9H-purin-6-yl)amino]-N-ethylethane-sulfonamide | Analogous to Route I | LC/MS (System C) R$_t$ 2.65 min. Mass Spectrum m/z 496 [MH$^+$] |
| 178 | (2R,3R,4S,5S)-2-[6-(cyclo-pentylamino)-9H-purin-9-yl]-5-[5-(trifluoromethyl)-1,3,4-oxadiazol-2-yl]-tetrahydrofuran-3,4-diol | Analogous to Route A | LC/MS (System C) R$_t$ 2.80 min. Mass Spectrum m/z 442 [MH$^+$] |
| 179 | (2R,3R,4S,5S)-2-(6-{[(1S,2S)-2-hydroxy-cyclopentyl]-amino}-9H-purin-9-yl)-5-[5-(trifluoromethyl)-1,3,4-oxadiazol-2-yl]-tetrahydrofuran-3,4-diol | Analogous to Route A | LC/MS (System C) R$_t$ 2.48 min. Mass Spectrum m/z 458 [MH$^+$] |
| 180 | ethyl 4-[(9-{(2R,3R,4S,5S)-3,4-dihydroxy-5-[5-(trifluoromethyl)-1,3,4-oxadiazol-2-yl]-tetrahydrofuran-2-yl}-9H-purin-6-yl)amino]-piperidine-1-carboxylate | Analogous to Route A | LC/MS (System C) R$_t$ 2.74 min. Mass Spectrum m/z 529 [MH$^+$] |
| 181 | 2R,3R,4S,5S)-2-[6-(4-chloro-2-fluoroanilino)-9H-purin-9-yl]-5-(5-methyl-1,3,4-oxadiazol-2-yl)-tetrahydrofuran-3,4-diol | Analogous to Route Cc | LC/MS (System C) Rt 2.77 min. Mass Spectrum m/z 448 [MH$^+$] |
| 182 | (2R,3R,4S,5S)-2-[6-(4-chloro-2-fluoroanilino)-9H-purin-9-yl]-5-(3-cyclopropyl-isoxazol-5-yl)-tetrahydrofuran-3,4-diol | Analogous to Route W | LC/MS (System C) R$_t$ 3.15 min. Mass Spectrum m/z 473 [MH$^+$] |
| 183 | (2S,3S,4R,5R)-2-[3-(tert-butyl)isoxazol-5-yl]-5-{6-[(1-butyryl-piperidin-4-yl)amino]-9H-purin-9-yl}-tetrahydrofuran-3,4-diol | Analogous to Route Y | LC/MS (System C) R$_t$ 2.74 min. Mass Spectrum m/z 514 [MH$^+$] |
| 184 | isopropyl 4-[(9-{(2R,3R,4S,5S)-5-[3-(tert- | Analogous to Route Y | LC/MS (System C) R$_t$ 3.10 min. Mass Spectrum |

TABLE 1-continued

Examples

| Ex No | Name | Expt. Details (note 1) | Characterising data |
|---|---|---|---|
| | butyl)isoxazol-5-yl]-3,4-dihydroxy-tetrahydrofuran-2-yl}-9H-purin-6-yl)amino]-piperidine-1-carboxylate | | m/z 530 [MH$^+$] |
| 185 | (2S,3S,4R,5R)-2-[3-(tert-butyl)isoxazol-5-yl]-5-(6-{[1-(2,2,2-trifluoroacetyl)-piperidin-4-yl]amino}-9H-purin-9-yl)-tetrahydrofuran-3,4-diol | Analogous to Route Y | LC/MS (System C) R$_t$ 3.05 min. Mass Spectrum m/z 540 [MH$^+$] |
| 186 | methyl 4-[(9-{(2R,3R,4S,5S)-5-[3-(tert-butyl)isoxazol-5-yl]-3,4-dihydroxy-tetrahydrofuran-2-yl}-9H-purin-6-yl)amino]-piperidine-1-carboxylate | Analogous to Route Y | LC/MS (System C) R$_t$ 2.73 min. Mass Spectrum m/z 502 [MH$^+$] |
| 187 | (2R,3R,4S,5S)-2-[6-(4-chloro-2-fluoroanilino)-9H-purin-9-yl]-5-[3-(hydroxymethyl)-isoxazol-5-yl]-tetrahydrofuran-3,4-diol | Analogous to Route V | LC/MS (System C) R$_t$ 2.67 min. Mass Spectrum m/z 463 [MH$^+$] |
| 188 | (2R,3R,4S,5S)-2-[6-(2-chloro-4-fluoroanilino)-9H-purin-9-yl]-5-[3-(hydroxymethyl)-isoxazol-5-yl]-tetrahydrofuran-3,4-diol | Analogous to Route V | LC/MS (System C) R$_t$ 2.56 min. Mass Spectrum m/z 463 [MH$^+$] |
| 189 | (2R,3R,4S,5S)-2-[6-(2-fluoroanilino)-9H-purin-9-yl]-5-[3-(hydroxymethyl)-isoxazol-5-yl] tetrahydrofuran-3,4-diol | Analogous to Route V | LC/MS (System C) R$_t$ 2.40 min. Mass Spectrum m/z 429 [MH$^+$] |
| 190 | (2R,3R,4S,5S)-2-[6-(2-chloroanilino)-9H-purin-9-yl]-5-[3-(hydroxymethyl)-isoxazol-5-yl]-tetrahydrofuran-3,4-diol | Analogous to Route V | LC/MS (System C) R$_t$ 2.54 min. Mass Spectrum m/z 445 [MH$^+$] |
| 191 | (2R,3R,4S,5S)-2-(2-chloro-6-{[(1S,2S)-2-hydroxy-cyclopentyl]-amino}-9H-purin-9-yl)-5-[3-(hydroxymethyl)-isoxazol-5-yl]-tetrahydrofuran-3,4-diol | Analogous to Route Bb | LC/MS (System C) R$_t$ 2.32 min. Mass Spectrum m/z 453/455 [MH$^+$] |
| 192 | (2R,3R,4S,5S)-2-[2-chloro-6-(tetrahydro-2H- | Analogous to Route Bb | LC/MS (System C) R$_t$ 2.32 min. Mass Spectrum |

TABLE 1-continued

Examples

| Ex No | Name | Expt. Details (note 1) | Characterising data |
|---|---|---|---|
| | pyran-4-ylamino)-9H-purin-9-yl]-5-[3-(hydroxymethyl)-isoxazol-5-yl]-tetrahydrofuran-3,4-diol | | m/z 453/455 [MH$^+$] |
| 193 | 2-[(2-chloro-9-{(2R,3R,4S,5S)-3,4-dihydroxy-5-[3-(hydroxymethyl)-isoxazol-5-yl]-tetrahydrofuran-2-yl}-9H-purin-6-yl)amino]-N-ethylethane-sulfonamide | Analogous to Route Bb | LC/MS (System C) Rt 2.32 min. Mass Spectrum m/z 504/506 [MH$^+$] |
| 194 | ethyl 4-[(2-chloro-9-{(2R,3R,4S,5S)-3,4-dihydroxy-5-[3-(hydroxymethyl)-isoxazol-5-yl]-tetrahydrofuran-2-yl}-9H-purin-6-yl)amino]-piperidine-1-carboxylate | Analogous to Route Bb | LC/MS (System C) $R_t$ 2.60 min. Mass Spectrum m/z 524 [MH$^+$] |
| 195 | (2R,3R,4S,5S)-2-[2-chloro-6-(4-chloro-2-fluoroanilino)-9H-purin-9-yl]-5-[3-(hydroxymethyl)-isoxazol-5-yl]-tetrahydrofuran-3,4-diol | Analogous to Route Bb | LC/MS (System C) $R_t$ 3.10 min. Mass Spectrum m/z 497 [MH$^+$] |
| 196 | (2R,3R,4S,5S)-2-[2-chloro-6-(2-chloro-4-fluoroanilino)-9H-purin-9-yl]-5-[3-(hydroxymethyl)-isoxazol-5-yl]-tetrahydrofuran-3,4-diol | Analogous to Route Bb | LC/MS (System C) $R_t$ 3.02 min. Mass Spectrum m/z 497/499 [MH$^+$] |
| 197 | (2R,3R,4S,5S)-2-[2-chloro-6-(2-fluoroanilino)-9H-purin-9-yl]-5-[3-(hydroxymethyl)-isoxazol-5-yl]-tetrahydrofuran-3,4-diol | Analogous to Route Bb | LC/MS (System C) $R_t$ 2.72 min. Mass Spectrum m/z 463 [MH$^+$] |
| 198 | (2S,3S,4R,5R)-2-(3-ethylisoxazol-5-yl)-5-[2-methoxy-6-(tetrahydro-2H-pyran-4-ylamino)-9H-purin-9-yl]-tetrahydrofuran-3,4-diol | Analogous to Route L | LC/MS (System C) $R_t$ 2.57 min. Mass Spectrum m/z 447 [MH$^+$] |
| 199 | ethyl 4-({9-[(2R,3R,4S,5S)-5-(3-ethylisoxazol-5-yl)-3,4-dihydroxy-tetrahydrofuran-2-yl]-2-methoxy-9H-purin-6-yl}amino)-piperidine-1-carboxylate | Analogous to Route L | LC/MS (System C) $R_t$ 2.75 min. Mass Spectrum m/z 518 [MH$^+$] |

TABLE 1-continued

Examples

| Ex No | Name | Expt. Details (note 1) | Characterising data |
|---|---|---|---|
| 200 | (2S,3S,4R,5R)-2-(3-ethylisoxazol-5-yl)-5-(6-{[(1S,2S)-2-hydroxy-cyclopentyl]-amino}-2-methoxy-9H-purin-9-yl)-tetrahydrofuran-3,4-diol | Analogous to Route L | LC/MS (System C) $R_t$ 2.66 min. Mass Spectrum m/z 447 [MH$^+$] |
| 201 | (2S,3S,4R,5R)-2-(3-ethylisoxazol-5-yl)-5-(6-{[2-(ethylsulfonyl)ethyl]amino}-2-methoxy-9H-purin-9-yl)-tetrahydrofuran-3,4-diol | Analogous to Route L | LC/MS (System C) $R_t$ 2.42 min. Mass Spectrum m/z 483 [MH$^+$] |
| 202 | (2R,3R,4S,5S)-2-[6-(2-chloro-4-fluoroanilino)-2-methoxy-9H-purin-9-yl]-5-(3-ethyl isoxazol-5-yl)-tetrahydrofuran-3,4-diol | Analogous to Route L | LC/MS (System C) $R_t$ 3.12 min. Mass Spectrum m/z 491 [MH$^+$] |
| 203 | (2S,3S,4R,5R)-2-(3-ethylisoxazol-5-yl)-5-[6-(2-fluoroanilino)-2-methoxy-9H-purin-9-yl]-tetrahydrofuran-3,4-diol | Analogous to Route L | LC/MS (System C) $R_t$ 2.95 min. Mass Spectrum m/z 457 [MH$^+$] |
| 204 | (2R,3R,4S,5S)-2-[6-(4-chloro-2-fluoroanilino)-2-methoxy-9H-purin-9-yl]-5-(3-ethyl isoxazol-5-yl)-tetrahydrofuran-3,4-diol | Analogous to Route L | LC/MS (System C) $R_t$ 3.20 min. Mass Spectrum m/z 491 [MH$^+$] |
| 205 | (2S,3S,4R,5R)-2-[3-(tert-butyl)-1,2,4-oxadiazol-5-yl]-5-[6-(cyclo-propylamino)-9H-purin-9-yl]-tetrahydrofuran-3,4-diol | Analogous to Route N | LC/MS (System C) $R_t$ 2.53 min. Mass Spectrum m/z 402 [MH$^+$] |
| 206 | (2S,3S,4R,5R)-2-[5-(tert-butyl)-1,3,4-oxadiazol-2-yl]-5-[2-chloro-6-(4-chloro-2-fluoroanilino)-9H-purin-9-yl]-tetrahydrofuran-3,4-diol | Analogous to route Cc | LC/MS (System C) $R_t$ 3.32 min. Mass Spectrum m/z 524 [MH$^+$] |
| 207 | (2R,3R,4S,5S)-2-[6-(4-chloro-2-fluoroanilino)-9H-purin-9-yl]-5-(5-isopropyl-1,3,4-oxadiazol-2-yl)-tetrahydrofuran-3,4-diol | Analogous to Route Z | LC/MS (System C) $R_t$ 2.96 min. Mass Spectrum m/z 476 [MH$^+$] |

Experimental Details for Route (A)

Intermediate 1

(3aS,4S,6R,6aR)-6-(6-Chloro-purin-9-yl)-2,2-dimethyl-tetrahydro-furo[3,4-d][1,3]dioxole-4-carboxylic acid N'-(2,2-dimethyl-propionyl)-hydrazide (3aS,4S,6R,6aR)-6-(6-Chloro-purin-9-yl)-2,2-dimethyl-tetrahydro-furo[3,4-d][1,3]dioxole-4-carboxylic acid (2.5 g) suspended in 1,2-dimethoxymethane (100 ml) was treated with 2,2-dimethyl-propionic acid hydrazide (1.1 g) and 2-ethoxy-1-ethoxycarbonyl-1,2-dihydroquinoline (EEDQ), and the mixture heated under reflux for 16 h. The mixture was poured into aqueous citric acid (250 ml) and extracted with ethyl acetate; the organic layers were washed with citric acid and brine, dried (MgSO$_4$) and evaporated in vacuo to give the crude product. Purification by flash chromatography on silica gel (Biotage cartridge), eluting with ethyl acetate:cyclohexane 65:35, gave the title compound as a white solid (1.92 g).

LC/MS (System B): R$_t$ 2.49 min

Mass spectrum m/z 439 [MH$^+$].

Intermediate 2

9-[6S-(5-tert-Butyl-[1,3,4]oxadiazol-2-yl)-2,2-dimethyl-tetrahydro-(3aR,6aS)-furo[3,4-d][1,3]dioxol-4R-yl]-6-chloro-9H-purine (3aS,4S,6R,6aR)-6-(6-Chloro-purin-9-yl)-2,2-dimethyl-tetrahydro-furo[3,4-d][1,3]dioxole-4-carboxylic acid N'-(2,2-dimethyl-propionyl)-hydrazide (1.5 g) was dissolved in thionyl chloride (15 ml) and the solution irradiated in a microwave oven at 150W power for 7 min. The excess thionyl chloride was evaporated in vacuo to give the crude product which was dissolved in dry acetonitrile (6 ml) and heated under reflux for 3 h. The solvent was evaporated and the residue purified by flash chromatography on silica gel, eluting with ethyl acetate:cyclohexane 35:65-40:60, to give the title compound as a white solid (0.645 g).

LC/MS (System B): R$_t$ 2.86 min

Mass spectrum m/z 421 [MH$^+$].

Intermediate 3

(2S,3S,4R,5R)-2-(5-tert-Butyl-[1,3,4]oxadiazol-2-yl)-5-(6-chloro-purin-9-yl)-tetrahydro-furan-3,4-diol 9-[6S-(5-tert-Butyl-[1,3,4]oxadiazol-2-yl)-2,2-dimethyl-tetrahydro-(3aR,6aS)-furo[3,4-d][1,3]dioxol-4R-yl]-6-chloro-9H-purine (0.64 g) was treated with 10:1 trifluoroacetic acid:water (9 ml) at 0° C. for 5 h, and the mixture was allowed to stand in the refrigerator (2°) overnight. The mixture was evaporated in vacuo to low volume (ca. 1 ml), poured into ice cold aqueous sodium bicarbonate, and extracted with ethyl acetate (3×50 ml). The organic layers were washed with brine, dried (MgSO$_4$) and evaporated in vacuo to give the crude product (371 mg).

LC/MS (System B) R$_t$ 2.42 min

Mass spectrum m/z 381 [MH$^+$].

EXAMPLE 3

(2S,3S,4R,5R)-2-(5-tert-Butyl-[1,3,4]oxadiazol-2-yl)-5-[6-(tetrahydro-pyran-4-ylamino)-purin-9-yl]-tetrahydro-furan-3,4-diol (2S,3S,4R,5R)-2-(5-tert-Butyl-[1,3,4]oxadiazol-2-yl)-5-(6-chloro-purin-9-yl)-tetrahydro-furan-3,4-diol (41 mg) was heated under reflux with 4-aminotetrahydropyran hydrochloride (59 mg), diisopropylethylamine (0.11 ml), and isopropanol (5 ml) for 15 h. The solvent was evaporated in vacuo and the residue purified by chromatography on silica gel, eluting with ethyl acetate:methanol 100:0-90:10, to give the title compound (37 mg).

LC/MS (System B) R$_t$ 2.31 min.

Mass Spectrum m/z 446 [MH$^+$].

Experimental Details for Route (B)

Intermediate 4

2-Chloro-N-(tetrahydro-pyran-4-yl)-adenosine

A mixture of acetic acid 4R-acetoxy-5R-acetoxymethyl-2R-(2,6-dichloro-purin-9-yl)-tetrahydro-furan-3R-yl ester (10 g), diisopropylethylamine (5.7 ml), and 4-amino tetrahydropyran hydrochloride (2.02 g), in isopropanol (200 ml) was heated at 50° for 4 h. The cooled mixture was evaporated in vacuo, the residue re-dissolved in methanol (200 ml) and ammonia gas bubbled through the solution for 2 h. The mixture was stirred at 22° C. overnight, and evaporated in vacuo to give a brown oily solid. Purification by flash chromatography on silica gel (Merck 9385), eluting with 75:8:1 DCM:EtOH:880NH$_3$ to 50:8:1 DCM:EtOH:880NH$_3$, gave the title compound as a pale brown oily solid (7.81 g).

LC/MS (System B) R$_t$ 2.24 min.

Mass spectrum m/z 3.86 [MH$^+$].

Intermediate 5

{6R-[2-Chloro-6-(tetrahydro-pyran-4-ylamino)-purin-9-yl]-2,2-dimethyl-tetrahydro-(3aR,6aR)-furo[3,4-d][1,3]dioxol-4R-yl}-methanol A solution of 2-chloro-N-(tetrahydro-pyran-4-yl)-adenosine (7.81 g) in acetone (500 ml) was treated with 2,2-dimethoxypropane (14.7 ml) and p-toluenesulphonic acid (3.8 g) and the mixture was stirred at 22° C. overnight. A white precipitate formed. The mixture was evaporated in vacuo, and the residue partitioned between ethyl acetate (700 ml) and aqueous sodium bicarbonate solution (500 ml). The organic layer was washed with aqueous sodium bicarbonate (2×250 ml), dried (Na$_2$SO$_4$) and evaporated in vacuo to give a pale brown foam (7 g). Purification by flash chromatography on silica gel (Merck 9385), eluting with ethyl acetate:cyclohexane 4:1, gave the title compound as a pale yellow foam (5.7 g).

LC/MS (System B) R$_t$ 2.68 min.

Mass spectrum m/z 426 [MH$^+$].

Intermediate 6

(3aS,4S,6R,6aR)-6-[2-Chloro-6-(tetrahydro-pyran-4-ylamino)-purin-9-yl]-2,2-dimethyl-tetrahydro-furo[3,4-d][1,3dioxole-4-carboxylic Acid A solution of {6R-[2-chloro-6-(tetrahydro-pyran-4-ylamino)-purin-9-yl]-2,2-dimethyl-tetrahydro-(3aR,6aR)-furo[3,4-d][1,3]dioxol-4R-yl}-methanol (2.5 g) in ethyl acetate (90 ml) was treated with saturated aqueous sodium bicarbonate solution (60 ml) and the biphasic mixture stirred rapidly at 0° C. After stirring at 0° C. for 5 min, potassium bromide (70 mg) was added followed by 2,2,6,6-tetramethyl-1-piperidinyloxy, free radical (TEMPO) (4.6 mg). A freshly prepared solution of sodium bicarbonate (185 mg) in aqueous sodium hypochlorite (3.2 ml) and water was added dropwise to the cooled, stirred mixture over 15 min. The mixture was stirred for a further 20 min at 0° C. Two further additions were made of potassium bromide, TEMPO, and the freshly prepared sodium bicarbonate/aqueous sodium hypochlorite solution same quantities as before, followed each time by stirring at 0° C. for 15–20 min. The mixture was poured into ethyl acetate (400 ml), shaken with sodium sulphite (10 g), diluted with water (300 ml), shaken, and the organic and aqueous layers separated. The aqueous layer was acidified to pH 1–2 with 2N hydrochloric acid solution and extracted with ethyl acetate (2×300 ml). The organic layers were combined with those from a second, identical reaction, and evaporated in vacuo to give the product as a cream foam (4.47 g).

LC/MS (System B) R$_t$ 2.81 min.
Mass spectrum m/z 440 [MH$^+$].

Intermediate 7

(3aS,4S,6R,6aR)-6-[2-Chloro-6-(tetrahydro-pyran4-ylamino)-purin-9-yl]-2,2-dimethyl-tetrahydro-furo[3,4-d][1,3]dioxole-4-carboxylic Acid N'-(2,2-dimethyl-propionyl)-hydrazide Diisopropylethylamine (0.487 ml) was added to a stirred solution of (3aS,4S,6R,6aR)-6-[2-chloro-6-(tetrahydro-pyran-4-ylamino)-purin-9-yl]-2,2-dimethyl-tetrahydro-furo[3,4-d][1,3]dioxole-4-carboxylic acid (350 mg) in dry tetrahydrofuran (8 ml) at 0° C. under nitrogen. After 5 min pivaloyl chloride (0.098 ml) was added and the mixture was stirred at 0° C. for 2.5 h. 2,2-Dimethyl-propionic acid hydrazide was added in tetrahydrofuran (2 ml) at 0°, and stirring was continued at 0–22° C. overnight. The mixture was concentrated in vacuo and partitioned between ethyl acetate (2×30 ml) and saturated aqueous sodium bicarbonate (30 ml). The organic layers were washed with brine (50 ml), dried (MgSO$_4$) and evaporated in vacuo. The residue was azeotroped with dichloromethane (10 ml) to give the title compound as a cream solid (357 mg).

LC/MS (System B) R$_t$ 2.76 min.
Mass spectrum m/z 538 [MH$^+$].

Intermediate 8

{9-[6S-(5-tert-Butyl-[1,3,4]oxadiazol-2-yl)-2,2-dimethyl-tetrahydro-(3aR,6aS)-furo[3,4-d][1,3]dioxol-4R-yl]-2-chloro-9H-purin-6-yl}-(tetrahydro-pyran-4-yl)-amine (3aS,4S,6R,6aR)-6-[2-Chloro-6-(tetrahydro-pyran4-ylamino)-purin-9-yl]-2,2-dimethyl-tetrahydro-furo[3,4-d][1,3]dioxole-4-carboxylic acid N'-(2,2-dimethyl-propionyl)-hydrazide (150 mg) was dissolved in N,N-dimethylformamide (1.2 ml) and the solution cooled to 0° C. under nitrogen. To the cooled, stirred solution phosphorous oxychloride (0.039 ml) was added. The solution was stirred at 0° C. for 1 h, and at 22° C. for 16 h. The mixture was cooled to 0° C., more phosphorous oxychloride (0.026 ml) was added, and the mixture was stirred at 0° C. for 1 h, and at 22° C. for 20 h. The mixture was partially evaporated in vacuo, and partitioned between ethyl acetate (2×30 ml) and aqueous sodium bicarbonate (30 ml). The organic layers were dried (MgSO$_4$) and concentrated in vacuo to give a yellow oil. Purification by flash chromatography on silica gel, eluting with 30–100% ethyl acetate in cyclohexane, gave the title compound (60 mg).

LC/MS (System A) R$_t$ 4.41 min.
Mass Spectrum m/z 520 [MH$^+$].

EXAMPLE 8

(2S,3S,4R,5R)-2-(5-tert-Butyl-[1,3,4]oxadiazol-2-yl)-5-[2-chloro-6-(tetrahydro-pyran-4-ylamino)-purin-9-yl]-tetrahydro-furan-3,4-diol Formate {9-[6S-(5-tert-Butyl-[1,3,4]oxadiazol-2-yl)-2,2-dimethyl-tetrahydro-(3aR,6aS)-furo[3,4-d][1,3]dioxol-4R-yl]-2-chloro-9H-purin-6-yl}(tetrahydro-pyran-4-yl)-amine (60 mg) was dissolved in 10:1 trifluoroacetic acid:water (2 ml) and the mixture was stirred at 0° C. for 1 h, and at 22° C. for 4 h. The mixture was evaporated in vacuo, and azeotroped with toluene (2×6 ml). The residue was purified by preparative HPLC (gradient profile 5–90% (ii) over 18.5 min) to give the title compound as a white solid (37 mg).

LC/MS (System A) R$_t$ 3.86 min
Mass spectrum m/z 480 [MH$^+$]

Experimental Details for Route (C)

Intermediate 9

(3aS,4S,6R,6aR)-6-(6-Cyclopentylamino-purin-9-yl)-2,2-dimethyl-tetrahydro-furo[3,4-d][1,3]dioxole-4-carboxylic Acid Methyl Ester A solution of (3aS,4S,6R,6aR)-6-(6-cyclopentylamino-purin-9-yl)-2,2-dimethyl-tetrahydro-furo[3,4-d][1,3]dioxole-4-carboxylic acid (3.018 g) and 2-ethoxy-1-ethoxycarbonyl-1,2-dihydroquinoline (2.66 g) in methanol (120 ml) was heated under reflux for 17 h. The resulting mixture was concentrated in vacuo and the residue dissolved in ethyl acetate (150 ml). The solution was washed with 0.5M aqueous citric acid solution (3×25 ml) and brine (50 ml), dried (magnesium sulphate), and evaporated in vacuo to give a white foam. Purification by column chromatography on silica gel, eluting with ethyl acetate:cyclohexane (1:1), gave the title compound as a white solid (2.32 g).

TLC SiO$_2$ (CH$_2$Cl$_2$:MeOH:880NH$_3$ 94:6:1) R$_f$=0.62

Intermediate 10

(3aS,4S,6R,6aR)-6-(6-Cyclopentylamino-purin-9-yl)-2,2-dimethyl-tetrahydro-furo[3,4-d][1,3]dioxole-4-carboxylic Acid Hydrazide A mixture of (3aS,4S,6R,6aR)-6-(6-cyclopentylamino-purin-9-yl)-2,2-dimethyl-tetrahydro-furo[3,4-d][1,3]dioxole-4-carboxylic acid methyl ester (0.48 g) and hydrazine hydrate (0.29 ml) in methanol (10 ml) was heated at reflux for 28 h. After cooling to room temperature, the mixture was concentrated in vacuo and the residue evaporated twice with dichloromethane (2×20 ml) to give the title compound as a white solid (0.49 g).

NMR (DMSO) 9.4 ($\overline{1}$H, brs, NH), 8.32 ($\overline{1}$H, s, CH), 8.20 ($\overline{1}$H, s, CH), 7.90 ($\overline{1}$H, brd, NH), 6.35 ($\overline{1}$H, brs, CH), 5.28 ($\overline{2}$H, brm, 2×CH), 4.65 ($\overline{1}$H, brs, CH), 4.50 ($\overline{1}$H, brm, CH), 4.20 ($\overline{2}$H, brs, NH2), 2.0-1.5 ($\overline{11}$H, 2×m+S,4×CH$_2$+CH$_3$)

Intermediate 11

Cyclopentyl-[9-(2,2-dimethyl-6S-[1,3,4]oxadiazol-2-yl-tetrahydro-(3aR,6aS)-furo[3,4-d][1,3]dioxol-4R-yl)-9H-purin-6-yl]-amine A mixture of (3aS,4S,6R,6aR)-6-(6-cyclopentylamino-purin-9-yl)-2,2-dimethyl-tetrahydro-furo[3,4-d][1,3]dioxole-4-carboxylic acid hydrazide (0.5 g) and triethylorthoformate (5 ml, 4.45 g) was heated at reflux for 48 h; on cooling, the solution was evaporated to give a brown oil. Purification by flash chromatography on silica gel, eluting with ethyl acetate: cyclohexane (3:1), afforded the title compound as a cream foam (0.157 g).

TLC SiO$_2$ (Ethyl acetate:cyclohexane 3:1) R$_f$=0.17

EXAMPLE 15

(2R,3R,4S,5S)-2-(6-Cyclopentylamino-purin-9-yl)-5-[1,3,4]oxadiazol-2-yl-tetrahydro-furan-3,4-diol Trifluoroacetic acid (1.5 ml) and water (0.15 ml) were added to cyclopentyl-[9-(2,2-dimethyl-6S-[1,3,4]oxadiazol-2-yl-tetrahydro-(3aR,6aS)-furo[3,4-d][1,3]dioxol-4R-yl)-9H-purin-6-yl]-amine (0.157 g) at 0° C. and the mixture was stirred for 2 h. The resulting solution was poured into 8% aqueous sodium bicarbonate solution (10 ml) and extracted with ethyl acetate (4×20 ml); the organic layers were dried (MgSO$_4$), filtered and evaporated to dryness to give a pale cream foam (0.148 g). Methanol (20 ml) was added and the solid filtered off to afford the title compound as a white solid (0.46 g).

TLC SiO$_2$ (Ethyl acetate) R$_f$=0.13

Analysis Found: C, 50.77; H, 5.14; N, 25.53%

C$_{16}$H$_{19}$N$_7$O$_4$. 0.2MeOH. 0.1H$_2$O requires: C 50.99; H, 5.3; N, 25.7%

Experimental Details for Route (D)

Intermediate 12

(3aS,4S,6R,6aR)-6-(6-Chloro-purin-9-yl)-2,2-dimethyl-tetrahydro-furo[3,4-d][1,3]dioxole-4-carboxylic Acid (2-oxo-butyl)-amide A solution of (3aS,4S,6R,6aR)-6-(6-chloro-purin-9-yl)-2,2-dimethyl-tetrahydro-furo[3,4-d][1,3]dioxole-4-carboxylic acid (1.3 g), in dry tetrahydrofuran (30 ml) was cooled to 3° C. before triethylamine (1.07 ml) was added. After strirring for 15 min at 3° C., trimethylacetyl chloride (0.56 ml) was added and the suspension stirred for 40 min at 3° C. This suspension was added to a stirred mixture of the 2-oxobutylamine hydrochloride in acetonitrile (50 ml) containing triethylamine (2.3 ml). The mixture was allowed to warm to room temperature, stirred overnight, and partitioned between ethyl acetate (150 ml) and 10% aqueous sodium chloride (100 ml). The separated aqueous phase was further extracted with ethyl acetate (2×100 ml) and the combined organic extracts were washed with brine (70 ml), dried and concentrated in vacuo to give a dark red gum (1.83 g). Purification by chromatography on silica gel (Merck 7734), eluting with dichloromethane:ethanol:880 ammonia (250:8:1) gave the title compound as a yellow-brown foam (1.11 g).

NMR δ (CDCl$_3$) 8.68 (1H,s,CH), 8.27 (1H,s,CH), 6.73 (1H,brt,NH), 6.30 (1H,d,CH), 5.64 (1H,dd,CH), 5.46 (1H,dd,CH), 4.80 (1H,d,CH), 3.76 (2H, ABX,CH$_2$), 2.26 (2H,q,CH$_2$), 1.65 (3H,s, —CH$_3$), 1.42 (3H,s, —CH$_3$), 0.99 (3H,t,CH$_3$).

Intermediate 13

6-Chloro-9-[6S-(5-ethyl-oxazol-2-yl)-2,2-dimethyl-tetrahydro-(3a R,6aS)-furo[3,4-d][1,3]dioxol-4R-yl]-9H-purine Phosphorous oxychloride (1.43 g) was added to a stirred solution of (3aS,4S,6R,6aR)-6-(6-chloro-purin-9-yl)-2,2-dimethyl-tetrahydro-furo[3,4-d)[1,3]dioxole-4-carboxylic acid (2-oxo-butyl)-amide (1.05 g), in acetonitrile (60 ml). The solution was stirred at reflux for 5.5 h before standing at room temperature overnight. Stirring was continued at reflux for a further 4.5 h, and the mixture was cooled and partitioned between ethyl acetate (150 ml) and 8% aqueous sodium bicarbonate (100 ml). The separated aqueous phase was further extracted with ethyl acetate (1×100 ml) and the combined organic extracts were dried and concentrated in vacuo to give a red gum (1.8 g). Purification by chromatography on silica gel (Merck 7734), eluting with dichloromethane:ethanol:ammonia (250:8:1) gave the title compound as a yellow gum (0.86 g).

TLC SiO$_2$ (CH$_2$Cl$_2$:EtOH:880NH$_3$ 100:8:1) R$_f$=0.5.

Intermediate 14

(2R,3R,4S,5S)-2-(6-Chloro-purin-9-yl)-5-(5-ethyl-oxazol-2-yl)-tetrahydro-furan-3,4-diol To cooled (0°) 6-chloro-9-[6S-(5-ethyl-oxazol-2-yl)-2,2-dimethyl-tetrahydro-(3aR,6aS)-furo[3,4-d][1,3]dioxol-4R-yl]-9H-purine (0.85 g) was added a cold (0° C.) mixture of trifluoroacetic acid (8.2 ml) and water (0.8 ml). The mixture was stirred at 0° C. for 5 h before being stored in the refrigerator overnight. The mixture was concentrated in vacuo to give a yellow residue which was azeotroped with dichloromethane:ethanol:ammonia (75:8:1) (3×40 ml) to give a yellow liquid (4 ml). This was diluted with ethanol (5 ml) and purified by chromatography on silica gel (Merck 7734), eluting with dichloromethane:ethanol:ammonia (100:8:1) to (50:8:1) to give the title diol as a pale yellow solid (0.355 g).

NMR δ (DMSO) 9.00 (1H,s,CH), 8.85 (1H,s,CH), 6.99 (1H,fine t,CH), 6.1-5.9 (2H,2×brs,2×OH), 5.05 (1H,d,CH), 4.89 (1H,t,CH), 4.70 (1H,t,CH), 2.7 (2H,dq,CH$_2$), 1.20 (3H,t,CH$_3$).

EXAMPLE 16

(2S,3S,4R,5R)-2-(5-Ethyl-oxazol-2-yl)-5-[6-(tetrahydro-pyran-4-ylamino)-purin-9-yl]-tetrahydro-furan-3,4-diol To a solution of (2R,3R,4S,5S)-2-(6-chloro-purin-9-yl)-5-(5-ethyl-oxazol-2-yl)-tetrahydro-furan-3,4-diol (0.19 g), in isopropanol (15 ml) was added diisopropylethylamine (0.3 ml) and 4-aminotetrahydropyran hydrochloride (0.135 g). After stirring at reflux for 16 h, further diisopropylethylamine (0.2 ml) and 4-aminotetrahydropyran hydrochloride (60 mg) were added. Stirring was continued at reflux for a further 20 h before the mixture was cooled and concentrated in vacuo to give a yellow gum (0.8 g). Purification by chromatography on silica gel (Merck 7734) with dichloromethane:ethanol:ammonia (250:8:1)-(100:8:1), gave the title compound, as a white foam (0.182 g).

Mass spectrum m/z 417 [MH$^+$]

NMR δ (CDCl$_3$) 8.27 (1H,s,CH), 8.13 (1H,s,CH), 6.72 (1H,s,CH), 6.6-6.2 (1H,vbrs, —OH), 6.21 (1H,d,CH), 5.98 (1H,brd,NH), 5.31 (1H,d,CH), 4.79 (2H,m,2×CH), 4.40 (1H,brs,CH), 4.02 (2H,brd,2×CH equatorial), 3.57 (2H,t,2×CH axial), 2.66 (2H,q,CH$_2$), 2.07 (2H,brd,2×CH equatorial), 1.63 (2H,brq,2×CH axial), 1.23 (3H,t,CH$_3$).

Experimental Details for Route (E)

EXAMPLE 17

(2S,3S,4R,5R)-2-(6-Cyclopentylamino-purin-9-yl)-5-(5-cyclopropyl-[1,3,4]thiadiazol-2-yl)-tetrahydro-furan-3,4-diol Cyclopropanecarboxylic acid N'-[6R-(6-cyclopentylamino-purin-9-yl)-2,2-dimethyl-tetrahydro-(3aS,6a R)-furo[3,4-d][1,3]dioxole-4S-carbonyl]-hydrazide (12 mg) was heated at 80° C. with Lawesson's reagent (19 mg) in acetonitrile (2 ml) for 8 h. Further Lawesson's reagent (40 mg) was added, and the mixture heated at 70° C. for 16 h. The solvent was evaporated and the residue purified by chromatography on silica gel (Varian Bondelut cartridge) eluting with ethyl acetate:cyclohexane 20:80–100:0 and ethyl acetate:methanol 98:2-95:5, to give the protected product (31 mg). This material was treated with trifluoroacetic acid (1 ml) and water (0.1 ml) and the solution allowed to stand at 4° C. overnight (19 h). The mixture was poured into ice cold aqueous sodium bicarbonate (15 ml) and extracted with ethyl acetate (3×15 ml). The organic layers were washed with brine, dried (MgSO$_4$) and evaporated in vacuo to give a colourless gum. Purification by automated HPLC (gradient profile 30–60% (ii) over 20 min) gave the title compound (1.33 mg).

LC/MS (System A) R$_t$ 4.0 min

Mass spectrum m/z 430 [MH$^+$].

Experimental Details for Route (F)

Intermediate 15

(3aS,4S,6R,6aR)-6-(6-Isopropylamino-purin-9-yl)-2,2-dimethyl-tetrahydro-furo[3,4-d][1,3dioxole-4-carboxylic Acid A mixture of (3aS,4S,6R,6aR)-6-(6-chloro-purin-9-yl)-2,2-dimethyl-tetrahydro-furo[3,4-d][1,3]dioxole-4-carboxylic acid (5.82 g) and isopropyl amine (7.27 ml) in isopropanol (20 ml) was heated under reflux for 40 h, cooled to room temperature and concentrated in vacuo. The resulting residue was partitioned between ethyl acetate (75 ml) and citric acid (0.5M, 75 ml). The layers were separated, and the organic phase washed with citric acid solution (2×50 ml). The combined organic extracts were washed with water (50 ml) and brine (80 ml), dried (MgSO$_4$), filtered and concentrated in vacuo to afford the title compound as a light brown foam (4.49 g).

TLC SiO$_2$ (ethyl acetate) R$_f$=0.35

Intermediate 16

(3aS,4S,6R,6aR)-6-(6-Isopropylamino-purin-9-yl)-2,2-dimethyl-tetrahydro-furo[3,4-d][1,3]dioxole-4-carboxylic Acid Methyl Ester A mixture of (3aS,4S,6R,6aR)-6-(6-isopropylamino-purin-9-yl)-2,2-dimethyl-tetrahydro-furo[3,4-d][1,3]dioxole-4-carboxylic acid (4.82 g) and 2-ethoxy-N-ethoxycarbonyl-1,2-dihydroquinoline (EEDQ, 3.36 g) in methanol (150 ml) was heated under reflux for 60 h. After cooling to room temperature, the solution was concentrated in vacuo and the resulting residue partitioned between ethyl acetate (100 ml) and citric acid solution (0.5M, 75 ml). The aqueous layer was extracted with ethyl acetate (4×25 ml) and the combined organic extracts were washed with water (50 ml) and brine (75 ml), dried (MgSO$_4$), filtered and concentrated in vacuo. The resulting residue was purified by flash chromatography on silica gel, eluting with ethyl acetate: cyclohexane (1:1) to afford the title compound as a white solid (3.76 g).

TLC SiO$_2$ (ethyl acetate:cyclohexane 1:1) R$_f$=0.20.

Intermediate 17

(3aS,4S,6R,6aR)-6-(6-Isopropylamino-purin-9-yl)-2,2-dimethyl-tetrahydro-furo[3,4-d][1,3]dioxole-4-carboxylic Acid Hydrazide A mixture of (3aS,4S,6R,6aR)-6-(6-isopropylamino-purin-9-yl)-2,2-dimethyl-tetrahydro-furo[3,4-d][1,3]dioxole-4-carboxylic acid methyl ester (3.76 g) and hydrazine hydrate (1.26 ml) in methanol (140 ml) was heated under reflux for 48 h. After cooling to room temperature, the mixture was concentrated in vacuo and the residue triturated with ethyl acetate to afford the title compound as a white solid (3.3 g).

Analysis Found: C, 51.5; H, 6.5; N, 23.6%

C$_{16}$H$_{23}$N$_7$O$_4$. 0.4EtOAc requires: C, 51.0; H, 6.4; N, 23.8%

EXAMPLE 18

(2R,3R,4S,5R)-2-(6-Isopropylamino-purin-9-yl)-5-(5-methyl-4H-[1,2,4]triazol-3-yl)-tetrahydro-furan-3,4-diol Trifluoroacetate A mixture of (3aS,4S,6R,6aR)-6-(6-isopropylamino-purin-9-yl)-2,2-dimethyl-tetrahydro-furo[3,4-d][1,3]dioxole-4-carboxylic acid hydrazide (0.5 g), ethylacetimidate hydrochloride (0.24 g) and triethylamine (0.55 ml) in ethanol (10 ml) was heated under reflux for 72 h and cooled to room temperature. The solvent was evaporated in vacuo and the residue purified by flash chromatography on silica gel (Merck 9385), eluting with ethyl acetate: methanol (9:1), to afford a white solid (0.37 g), which was treated with trifluoroacetic acid (3.6 ml) and water (0.36 ml); the mixture stirred at 0° C. for 6 h. The resulting solution was evaporated to dryness, toluene was added and the mixture re-evaporated to dryness. The resulting residue was triturated with ethyl acetate to afford the title compound as a white solid (0.41 g).

R (DMSO) 8.71 (1H, brs, NH), 8.40-8.20 (2H, s+brs 2×CH), 6.11 (H, d, CH), 5.00 (H, d, CH), 4.73 (1H, t, CH), 4.44 (2H, t+brm, 2 ×CH), 2.42 (3H, s, CH$_3$), 1.27 (6H, d, 2×CH$_3$)

Analysis Found: C, 42.9; H, 4.45; N, 23.5%

C$_{15}$H$_{20}$N$_8$O$_3$ requires: C, 43.0; H, 4.4; N, 23.6%

Experimental Details for Route (G).

Intermediate 18

6-Chloro-9-[6S-(3-cyclopropyl-[1,2,4]oxadiazol-5-yl)-2,2-dimethyl-tetrahydro-(3aR,6aS)-furo]3,4-d][1,3]dioxol-4R-yl]-9H-purine A suspension of (3aS,4S,6R,6aR)-6-(6-chloro-purin-9-yl)-2,2-dimethyl-tetrahydro-furo[3,4-d][1,3]dioxole-4-carboxylic acid (4.17 g) in anhydrous tetrahydrofuran (80 ml) was cooled under nitrogen to 5° C. To the suspension was added diisopropylethylamine (4.68 ml). Pivaloyl chloride (1.65 ml) was added after 10 min, and the mixture was stirred at 0° C. for 1 h, and allowed to warm to room temperature over 1 h. The mixture was again cooled to 5° C, cyclopropylamidoxime (1.47 g) was added dropwise, the cooling bath was removed and stirring was continued at 22° C. for 18 h. The diisopropylethylamine hydrochloride was filtered off and washed with tetrahydrofuran (100 ml). The filtrate was heated at reflux for 10 h, cooled and concentrated in vacuo to give a residue which was purified by chromatography on silica gel (Varian Mega Bondelut cartridge), eluting with ethyl acetate:cyclohexane (3:1), to afford the title compound as a white solid (1.99 g).

LC/MS (System B): R$_t$=2.91 min

Mass spectrum m/z 405 (MH$^+$)

Intermediate 19

(2R,3R,4S,5S)-2-(6-Chloro-purin-9-yl)-5-(3-cyclopropyl-[1,2,4]oxadiazol-5-yl)-tetrahydro-furan-3,4-diol A solution of 6-chloro-9-[6S-(3-cyclopropyl-[1,2,4]oxadiazol-5-yl)-2,2-dimethyl-tetrahydro-(3aR,6aS)-furo[3,4-d][1,3]dioxol-4R-yl]-9H-purine (1.99 g) in a cold mixture of trifluoroacetic acid:water (9:1; 25 ml) was kept at 4° C. for 20 h. The resulting solution was basified in an ice bath with a saturated solution of sodium bicarbonate (200 ml), extracted with ethyl acetate (3×70 ml) and the extracts dried (MgSO$_4$) and concentrated in vacuo. The resulting brown oil was purified by chromatography on silica gel (Varian Mega Bondelut cartridge), eluting with dichloromethane:methanol (10:1) to afford the title compound (1.29 g) as a white solid.

LC/MS (System B): R$_t$=2.42 min

Mass spectrum m/z 365 (MH$^+$)

EXAMPLE 19

(2S,3S,4R,5R)-2-(3-Cyclopropyl-[1,2,4]oxadiazol-5-yl)-5-[6-(2S-hydroxy-cyclopent-(S)-ylamino)-purin-9-yl]-tetrahydro-furan-3,4-diol To a solution of (2R,3R,4S,5S)-2-(6-chloro-purin-9-yl)-5-(3-cyclopropyl-[1,2,4]oxadiazol-5-yl)-tetrahydro-furan-3,4-diol (50 mg) in isopropanol (5 ml) was added diisopropylethylamine (0.072 ml) and trans-(1S,2S)-2-aminocyclopentanol hydrochloride (37.8 mg) The mixture was heated at reflux for 48 h, cooled to room temperature and concentrated to dryness in vacuo to give a residue which was purified by solid phase extraction (5 g, Varian Mega Bondelut cartridge, aminopropyl bonded phase, eluting with (i) CHCl$_3$, (ii) ethyl acetate:cyclohexane (1:1), (iii) ethyl acetate, (iv) dichloromethane, (v) dichloromethane:methanol (20:1), (vi) dichloromethane:methanol (10:1) and (vii) methanol to afford the title compound (47.3 mg).

LC/MS (System B): R$_t$=2.37 min

Mass spectrum m/z 430 (MH$^+$)

Experimental Details for Route (H)

Intermediate 20

4-[9-(6S-Carboxy-2,2-dimethyl-tetrahydro-(3a R,6aS)-furo [3,4-d][1,3]dioxol-4R-yl)-9H-purin-6-ylamino]-piperidine-1-carboxylic Acid Ethyl Ester A mixture of ethyl-4-amino-piperidinecarboxylate (1.80 ml), (3aS,4S,6R,6aR)-6-(6-chloro-purin-9-yl)-2,2-dimethyl-tetrahydro-furo[3,4-d][1,3]dioxole-4-carboxylic acid (2.0 g) and diisopropylethylamine (2.74 ml) was heated at reflux in isopropanol (100 ml) for 70 h. After cooling to room temperature the mixture was concentrated in vacuo. Water (100 ml) was added to the residue and the mixture acidified to pH 4 (citric acid). The mixture was rapidly extracted with dichloromethane (3×50 ml) and the extracts dried (MgSO$_4$) and concentrated in vacuo to afford the title compound as a yellow solid (2.56 g).

LC/MS (System B): $R_t$=2.62 min

Mass spectrum m/z 477

Intermediate 21

4-[9-(6S-Carbamoyl-2,2-dimethyl-tetrahydro-(3aR,6aS)-furo[3,4-d][1,3]dioxol-4R-yl)-9H-purin-6-ylamino]-piperidine-1-carboxylic Acid Ethyl Ester A cooled (0° C.) solution of 4-[9-(6S-carboxy-2,2-dimethyl-tetrahydro-(3aR,6aS)-furo[3,4-d][1,3]dioxol-4R-yl)-9H-purin-6-ylamino]-piperidine-1-carboxylic acid ethyl ester (2.56 g) in anhydrous dichloromethane (50 ml) was treated with triethylamine (0.82 ml) and pivaloyl chloride (0.73 ml). Ammonia was bubbled into the solution for 70 min. The mixture was evaporated to dryness in vacuo to give a crude product, which was dissolved in ethyl acetate and washed wit h water (3×70 ml). The extracts were dried ($MgSO_4$) and concentrated in vacuo to afford the title compound as a pale orange solid (1.97 g).

LC/MS (System B): $R_t$=2.54 min

Mass spectrum m/z 476 ($MH^+$)

Intermediate 22

4-[9-(6 R-Cyano-2,2-dimethyl-(3aR,6aR)-tetrahydro-furo[3,4-d][1,3]dioxol-4R-yl)-9H-purin-6-ylamino]-piperidine-1-carboxylic Acid Ethyl Ester A solution of 4-[9-(6S-carbamoyl-2,2-dimethyl-tetrahydro-(3aR,6aS)-furo[3,4-d][1,3]dioxol-4R-yl)-9H-purin-6-ylamino]-piperidine-1-carboxylic acid ethyl ester (1.97 g) in anhydrous acetonitrile (40 ml) was treated with 4-dimethylaminopyridine (1.01 g). The mixture was cooled to 0° C. and phosphorus oxychloride (1.93 ml) added dropwise. The mixture was allowed to warm to room temperature and stirred at this temperature for 1 h then heated at reflux for 7 h. After cooling, the mixture was evaporated to dryness in vacuo to give the crude product which was dissolved in water (50 ml) and extracted with ethyl acetate (3×70 ml). The extracts were concentrated in vacuo to afford the title compound as a pale orange solid (1.91 g).

LC/MS (System A): $R_t$=4.09 min

Mass Spectrum m/z 458 ($MH^+$)

Intermediate 23

4-{9-[6R-(N-Hydroxycarbamimidoyl)-2,2-dimethyl-tetrahydro-(3aR,6aR)-furo[3,4-d][1,3]dioxol-4R-yl]-9H-purin-6-ylamino]-piperidine-1-carboxylic acid ethyl ester 4-[9-(6R-Cyano-2,2-dimethyl-(3aR,6aR)-tetrahydro-furo[3,4-d][1,3]dioxol-4R-yl)-9H-purin-6-ylamino]-piperidine-1-carboxylic acid ethyl ester (1.0 g) and hydroxylamine (50%; 0.29 ml) were heated at reflux in ethanol (25 ml) for 9 h. After cooling, the mixture was concentrated in vacuo and the residue was co-evaporated in toluene (50 ml) to give the title compound as a yellow solid (1.25 g).

LC/MS (System A): $R_t$=3.82 min

Mass spectrum m/z 490 ($MH^+$)

Intermediate 24

4-{9-[6R-(5-tert-Butyl-[1,2,4]oxadiazol-3-yl)-2,2-dimethyl-tetrahydro-(3aR,6aR)-furo[3,4-d][1,3]dioxol-4R-yl]-9H-purin-6-ylamino}-piperidine-1-carboxylic Acid Ethyl Ester 4-{9-[6R—(N-Hydroxycarbamimidoyl)-2,2-dimethyl-tetrahydro-(3aR,6aR)-furo[3,4-d][1,3]dioxol-4R-yl]-9H-purin-6-ylamino}-piperidine-1-carboxylic acid ethyl ester (1.0 g) was stirred with pivalic acid (15 ml) and pivalic anhydride (0.49 ml) at ambient temperature for 2 h, then heated at reflux for 9 h. After cooling, the residue was treated with a saturated solution of sodium bicarbonate (100 ml) and extracted with ethyl acetate (4×100 ml). The extracts were dried ($MgSO_4$) and concentrated in vacuo. To the residue was added diethylether (100 ml). A brown precipitate was formed and filtered off, and the filtrate was concentrated in vacuo to afford a crude product. Purification by chromatography on silica gel (Varian Mega Bondelut cartridge) eluting with ethyl acetate afforded the title compound as a pale orange oil (0.360 g).

LC/MS (System B):$R_t$=3.13 min

Mass spectrum m/z 557 ($MH^+$)

EXAMPLE 26

4-{9-[5R-(5-tert-Butyl-[1,2,4]oxadiazol-3-yl)-3R,4S-dihydroxy-tetrahydro-furan-2R-yl]-9H-purin-6-ylamino}-piperidine-1-carboxylic acid ethyl ester A solution of 4-{9-[6R-(5-tert-butyl-[1,2,4]oxadiazol-3-yl)-2,2-dimethyl-tetrahydro-(3aR,6aR)-furo[3,4-d][1,3]dioxol-4R-yl]-9H-purin-6-ylamino}-piperidine-1-carboxylic acid ethyl ester (360 mg) in a cold mixture of trifluoroacetic acid:water (9:1; 5 ml) was cooled to 0° C. for 20 h. The resulting solution was neutralised with an ice-cold saturated solution of sodium bicarbonate (70 ml), extracted with ethyl acetate (3×50 ml) and the extracts dried ($MgSO_4$) and concentrated in vacuo. Preparative hplc was carried out on a Supelcosil LC-ABZ column (size 21.2 mm×10 cm) operating at 8 ml/min (eluents were A: 0.1% trifluoroacetic acid/water, B: 0.01% trifluoroacetic acid in 95:5 acetonitrile/water) (gradient profile 15–95% B over 25 min), to afford the title compound as a white solid (6.9 mg).

LC/MS (System B): $R_t$=2.76 min

Mass spectrum m/z 517 ($MH^+$)

Experimental Details for Route (I)

Intermediate 25

(3aS,4S,6R,6aR)-6-Methoxy-2,2-dimethyl-tetrahydro-furo[3,4-d][1,3]dioxole-4-carboxylic Acid methoxy-methyl-amide (3aS,4S,6R,6aR)-Methoxy-2,2-dimethyl-tetrahydro-furo[3,4-d][1,3]dioxole-4-carboxylic acid (1 µg) was dissolved in dichloromethane (100 ml) and carbonyldi-imidazole (8.47 g) added portionwise over 10 min at 22° C. and the solution stirred at 22° C. for 0.5 h. N,O-Dimethylhydroxylamine hydrochloride (12.5 g) was dissolved in water (50 ml) and 10N sodium hydroxide (20 ml) added, and the solution extracted with dichloromethane (3×50 ml). The dichloromethane extracts were dried ($Na_2SO_4$) and filtered, and the solution added to the above solution. After stirring for 3 days, the solution was washed with 0.5M citric acid (200 ml), 8% sodium bicarbonate (200 ml), dried ($Na_2SO_4$) and evaporated in vacuo to give the title compound as a colourless oil (14.2 g).

TLC: $SiO_2$ (ether) $R_f$=0.33.

Intermediate 26

1-(6R-Methoxy-2,2-dimethyl-tetrahydro-(3aS,6aR)-furo[3,4-d][1,3]dioxol-4S-yl)-4,4-dimethyl-pent-2-yn-1-one 3,3-Dimethyl-1-butyne (10 g) in THF (90 ml) was added slowly to a 3.0M solution of methylmagnesium chloride in THF (50 ml) under nitrogen at 0–5° C., and stirred at 0–5° C. for 5 h. (3aS,4S,6R,6aR)-6-Methoxy-2,2-dimethyl-tetrahydro-furo[3,4-d][1,3]dioxole-4-carboxylic acid methoxy-methyl-amide (14.17 g) was added in THF (20 ml) over 20 min at 0–5° C., and the solution stirred at 0–5° C. for 2 h. The reaction mixture was quenched with 30% ammonium chloride (150 ml) and 2M hydrochloric acid (15 ml) and extracted with ethyl acetate (2×150 ml). The combined organic phases were dried ($Na_2SO_4$) and evaporated in vacuo, and the residue purified by flash chromatography over silica (150 g) eluting with cyclohexane-diethyl ether (2:1) to afford the title compound as a colourless solid (4.01 g).

TLC: SiO$_2$ (ether) R$_f$=0.55

Intermediate 27

1-(6R-Methoxy-2,2-dimethyl-tetrahydro-(3as,6aR)-furo[3,4-d][1,3]dioxol-4S-yl)-4,4-dimethyl-pentane-1,3-dione-3-oxime 1-(6R-Methoxy-2,2-dimethyl-tetrahydro-(3aS,6aR)-furo[3,4-d][1,3]dioxol-4S-yl)-4,4-dimethyl-pent-2-yn-1-one (573 mg) was dissolved in methanol (6 ml) and 50% aqueous hydroxylamine (0.19 ml) added. After standing at 23° C. for 5 h, the solution was concentrated in vacuo, diluted with water (10 ml) and extracted with ethyl acetate (2×15 ml). The extracts were dried (Na$_2$SO$_4$) and evaporated in vacuo to afford the title compound as a colourless oil (0.635 g).

TLC: SiO$_2$ (cyclohexane-Et$_2$O 3:2) R$_f$=0.16

Intermediate 28

Acetic Acid 4R-acetoxy-2S-(3-tert-butyl-isoxazol-5-yl)-5-methoxy-tetrahydro-furan-3R-yl Ester 1-(6R-Methoxy-2,2-dimethyl-tetrahydro-(3aS,6aR)-furo[3,4-d][1,3]dioxol-4S-yl)-4,4-dimethyl-pentane-1,3-dione 3-oxime (632 mg) was dissolved in methanol (15 ml) and conc. hydrochloric acid (1 ml) added. The resulting solution was heated under reflux under nitrogen for 20 h, cooled and evaporated in vacuo. The residue was dissolved in pyridine (10 ml) and 4-dimethylaminopyridine (1 mg) and acetic anhydride (2 ml) added. The solution was allowed to stand at 22° C./3 h, and the solvents removed in vacuo. The residue was dissolved in ethyl acetate (100 ml), washed with 8% sodium bicarbonate (50 ml), dried (Na$_2$SO$_4$) and evaporated in vacuo to give the title compound as a pale yellow gum (575 mg).

Mass spectrum m/z 342 (MH$^+$)

Intermediate 29

Acetic Acid 4R-acetoxy-5S-(3-tert-butyl-isoxazol-5-yl)-2R-(6-chloro-purin-9-yl)-tetrahydro-furan-3R-yl Ester 6-Chloropurine (1.36 g), toluene (20 ml) and hexamethyldisilazane (10 ml) were heated under reflux under nitrogen for 2 h, cooled, and evaporated in vacuo. The residue was co-evaporated with dry toluene (12 ml) and taken into dry acetonitrile (20 ml) and acetic acid 4R-acetoxy-2S-(3-tert-butyl-isoxazol-5-yl)-5-methoxy-tetrahydrofuran-3R-yl ester (1.019) and trimethylsilyl trifluoromethanesulfonate (1.8 ml) added, and the solution heated under reflux under nitrogen for 5 h. The solution was cooled and poured into 8% sodium bicarbonate (150 ml) and extracted with ethyl acetate (2×100 ml). The extracts were combined, dried (Na$_2$SO$_4$) and evaporated in vacuo. The residue was purified by flash chromatography over silica (200 g) eluting with cyclohexane-ether (1:1-1:4) to afford the title compound as a colourless foam (0.953 g).

LCMS (system A) R$_t$=4.35 min.

EXAMPLE 27

(2S,3S,4R,5R)-2-(3-tert-Butyl-isoxazol-5-yl)-5-[6-(2S-hydroxy-cyclopent-(S)-ylamine)-purin-9-yl]-tetrahydro-furan-3,4-diol Acetic acid 4R-acetoxy-5S-(3-tert-butyl-isoxazol-5-yl)-2R-(6-chloro-purin-9-yl)-tetrahydro-furan-3R-yl ester (70 mg) and trans-(1S,2S)-2-aminocyclopentanol hydrochloride (62 mg) were dissolved in isopropanol (10 ml) and di-isopropylethylamine (0.16 ml) added, and the solution heated under reflux for 17 h. The solvent was evaporated in vacuo and the residue dissolved in saturated methanolic ammonia (7 ml) and allowed to stand for 3 h. The solvent was removed in vacuo and the residue purified by chromatography over silica (5 g) eluting with ethyl acetate-methanol (10:1). Further purification by autoprep HPLC afforded the title compound as a colourless gum (40 mg).

LCMS (system A): R$_t$=3.81 min

Mass spectrum: m/z 445 (MH$^+$)

EXAMPLE 28

(2S,3S,4R,5R)-2-(3-tert-Butyl-isoxazol-5-yl)-5-[6-(tetrahydro-pyran-4-ylamino)-purin-9-yl]-tetrahydro-furan-3,4-diol Acetic acid 4R-acetoxy-5S-(3-tert-butyl-isoxazol-5-yl)-2R-(6-chloro-purin-9-yl)-tetrahydro-furan-3R-yl ester (70 mg) and 4-aminotetrahydropyran hydrochloride (62 mg) were dissolved in isopropanol (10 ml) and di-isopropylethylamine (0.16 ml) added, and the solution heated under reflux for 17 h The solvent was removed in vacuo and the residue dissolved in saturated methanolic ammonia (7 ml), and allowed to stand for 3 h. The solvent was removed in vacuo and the residue purified by solid phase extraction (Varian Bondelut aminopropyl bonded silica gel cartridge), eluting with ethyl acetate-methanol (10:1). Further purification by autoprep HPLC gave the title compound as a colourless gum (31 mg).

LCMS (system A): R$_t$=3.78 min

Mass spectrum m/z 445 (MH$^+$)

Experimental Details for Route (J)

Intermediate 30

(E)-3-Dimethylamino-1-(6R-methoxy-2,2-dimethyl-tetrahydro-(3aS,6aR)-furo[3,4-d][1,3]dioxol-4S-yl)-propenone 1-(6R-Methoxy-2,2-dimethyl-tetrahydro-(3aS,6aR)-furo[3,4-d][1,3]dioxol-4S-yl)-ethanone (0.62 g) was dissolved in toluene (25 ml) and dimethylformamide dimethyl acetal (5 ml) added and the solution heated under reflux under nitrogen for 17 h. The solvents were removed in vacuo and the residue purified by flash chromatography over silica (30 g) eluting with ethyl acetate to afford the title compound as a yellow gum (0.102 g).

Mass spectrum m/z 272 (MH$^+$)

Intermediate 31

5-(6R-Methoxy-2,2-dimethyl-tetra hydro-(3aR,6aR)-furo[3,4-d][1,3dioxol-4R-yl)-1H-pyrazole (E)-3-Dimethylamino-1-(6R-methoxy-2,2-dimethyl-tetrahydro-(3aR,6aR)-furo[3,4-d][1,3]dioxol-4S-yl)-propenone (102 mg) was dissolved in methanol (15 ml) and hydrazine hydrate (0.5 ml) added and the solution heated under reflux for 1.5 h. The solvents were removed in vacuo and the residue purified by flash chromatography over silica gel, eluting with diethyl ether to afford the title compound as a colourless gum (47 mg).

Mass spectrum m/z 241 (MH$^+$)

Intermediate 32

Acetic Acid 4R-acetoxy-2R-(1-acetyl-1 H-pyrazol-3-yl)-5R-methoxy-tetrahydro-furan-3R-yl Ester 5-(6R-Methoxy-2,2-dimethyl-tetrahydro-(3aR,6aR)-furo[3,4-d][1,3]dioxol-4R-yl)-1H-pyrazole (1.66 g) was dissolved in methanol (120 ml), treated with conc. hydrochloric acid (1 ml), heated under reflux for 22 h, cooled and evaporated in vacuo. The residue was dissolved in pyridine (80 ml), acetic anhydride (4 ml) added and the solution allowed to stand for 3 h. The solvents were removed in vacuo and the residue taken into ethyl acetate (200 ml) and washed successively with 0.5M citric acid (100 ml), 8% sodium bicarbonate (100 ml) and brine (100 ml). The organic phase was dried (Na$_2$SO$_4$), evaporated in vacuo and the residue purified by flash chromatography over silica gel, eluting with cyclohexane-diethyl ether (2:1-1:1) to afford the title compound as a colourless gum (646 mg).

Mass spectrum m/z 327 (MH$^+$), 344 (MNH$_4^+$)

Intermediate 33

Acetic Acid 4R-acetoxy-5R-(1-acetyl-1H-pyrazol-3-yl)-2R-(6-chloro-purin-9-yl)-tetrahydro-furan-3R-yl Ester 6-Chloropurine (1 g) was suspended in toluene (40 ml), hexamethyldisilazane (10 ml) was added, and the mixture was heated under reflux for 1 h. After cooling, the solvents were evaporated in vacuo followed by co-evaporation with toluene (10 ml). The residue was dissolved in dry acetonitrile (40 ml), acetic acid 4R-acetoxy-2R-(1-acetyl-1H-pyrazol-3-yl)-5R-methoxy-tetrahydro-fu ran-3R-yl ester (645 mg), DBU (1 ml) and trimethylsilyl trifluoromethanesulfonate (1 ml) were added, and the resulting solution was heated under reflux under nitrogen for 3 h. The cooled solution was poured into 8% sodium bicarbonate (150 ml) and extracted with ethyl acetate (2×100 ml). The combined extracts were dried (Na$_2$SO$_4$) and evaporated in vacuo to afford a mixture which was purified by flash chromatography over silica gel, eluting with ether-cyclohexane (3:1) to afford the title compound (42 mg).

Mass spectrum m/z 449/451 (MH$^+$)

Intermediate 34

(2R,3 R,4S,5R)-2-(6-Chloro-purin-9-yl)-5-(2H-pyrazol-3-yl)-tetrahydro-furan-3,4-diol Acetic acid 4R-acetoxy-5-(1-acetyl-1H-pyrazol-3-yl)-2R-(6-chloro-purin-9-yl)-tetrahydro-furan-3R-yl ester (42 mg) was dissolved in methanol (3 ml) and cooled to 0° C. Tert-butylamine (0.2 ml) was added and the solution allowed to stand for 25 min. at 0° C. The solvents were removed in vacuo to furnish the title compound (35 mg).

Mass spectrum m/z 323/325 (MH$^+$)

EXAMPLE 29

(2R,3R,4S,5R)-2-(2H-Pyrazol-3-yl)-5-(6-tetrahydro-pyran-4-ylamino-purin-9-yl)-tetrahydro-furan-3,4-diol (2R,3R,4S,5R)-2-(6-Chloro-purin-9-yl)-5-(2H-pyrazol-3-yl)-tetrahydro-furan-3,4-diol (35 mg) was dissolved in isopropanol (3 ml), N,N-di-isopropylethylamine (0.12 ml) and tetrahydro-pyran-4-ylamine hydrochloride (46 mg) were added, and the resulting solution was heated under reflux under nitrogen for 17 h. The solvent was removed in vacuo the residue dissolved in methanol (10 ml), and 8% sodium bicarbonate (3 ml) added, followed by silica gel (3 g). The solvents were removed in vacuo and the residue added to a flash column of silica gel packed in dichloromethane. Elution with dichloromethane-methanol (4:1) afforded the title compound as a clear viscous gum (5.2 mg).

LCMS (system A) R$_t$=3.34 min.

Mass spectrum m/z 388 (MH$^+$)

Experimental Details for Route (K)

Intermediate 35

(3aS,4S,6R,6aR)-6-(6-Chloropurin-9-yl)-2,2-dimethyl-tetrahydro-furo[3,4-d][1,3dioxole-4-carboxylic acid methoxy-methyl-amide (3aS,4S,6R,6aR)-6-(6-Chloro-purin-9-yl)-2,2-dimethyl-tetrahydro-furo[3,4-d][1,3]dioxole-4-carboxylic acid (35.88 g) was dissolved in dichloromethane (300 ml) and treated with 1,1'-carbonyldiimidazole (20.5 g) with ice-cooling. The solution was stirred at 22° C. for 1 h, N,O-dimethylhydroxylamine hydrochloride (12.3 g) and pyridine (15 ml) were added, and stirring was continued at 22° C. for 24 h. The solution was washed with 0.5M citric acid (250 ml) and 8% sodium bicarbonate (200 ml), dried (Na$_2$SO$_4$) and evaporated in vacuo. The residue was purified by flash chromatography over silica gel, eluting with ethyl acetate to afford the title compound as a colourless solid (26.4 g).

LCMS (system A) R$_t$=3.77 min

Mass spectrum m/z 384/386 (MH$^+$)

Intermediate 36

(3aS,4S,6R,6aR)-2,2-Dimethyl-6-(6-thioxo-1,6-dihydro-purin-9-yl)-tetrahydro-furo[3,4-d][1,3]dioxole-4-carboxylic Acid methoxy-methyl-amide (3aS,4S,6R,6a R)-6-(6-Chloro-purin-9-yl)-2;2-dimethyl-tetrahydro-furo[3,4-d][1,3]dioxide-4-carboxylic acid methoxy-methyl-amide (23.3 g) was suspended in ethanol (250 ml), and treated with sodium hydrogen sulfide (10 g). The mixture was stirred under reflux under nitrogen for 3 h, cooled and evaporated in vacuo. The residue in water (250 ml) was acidified with 0.5M citric acid (ca. 40 ml), filtered, and the filtered solid washed with water (250 ml) and isopropanol (100 ml) and dried in vacuo to afford the title compound as a yellow solid (16.3 g).

LC/MS (system A) R$_t$=3.53 min

Mass spectrum m/z 382 (MH$^+$)

Intermediate 37

{9-[6R-(5-Tert-Butyl-2H-pyrazol-3-yl)-2,2-dimethyl-tetrahydro-(3aR,6aR)-furo[3,4-d][1,3]dioxol-4R-yl]-9H-purin-6-yl}-cyclopentylamine (3aS,4S,6R,6aR)-2,2-Dimethyl-6-(6-thioxo-1,6-dihydro-purin-9-yl)-tetrahydro-furo[3,4-d][1,3]dioxole-4-carboxylic acid methoxy-methyl-amide (1 g) was dissolved in N,N-dimethylformamide (DMF) (25 ml) with heating and filtered whilst hot. The filtrate was treated with di-isopropylethylamine (0.5 ml) and Merrifield resin (chloromethyl form, 2 g, 0.8 mmol/g, 1% cross-linked) and the mixture shaken for 24 h. The mixture was filtered and the filtered resin washed with DMF (2×15 ml), dichloromethane (2×15 ml) and ether (3×15 ml). The above resin was added to a solution of 3,3-dimethyl-1-butynylmagnesium chloride (prepared by treating 3,3-dimethyl-1-butyne [2 ml] with 3.0M methyl magnesium chloride in tetrahydrofuran (THF) [4 ml] in THF [25 ml] at 22° C for 17 h) in THF at 0-5° C., and the mixture was stirred at 0–5C for 6 h. 2M Hydrochloric acid (6 ml) and THF (12 ml) were added, and after 10 min shaking, the resin was filtered and washed with THF (2×15 ml) and ether (2×15 ml). The resin was re-suspended in DMF (25 ml), hydrazine hydrate (2 ml) was added, and the mixture was shaken for 17 h. The mixture was filtered, washed with DMF (30 ml), dichloromethane (2×10 ml) and ether (3×10 ml), re-suspended in dichloromethane (15 ml), treated with 3-chloroperoxybenzoic acid (57-81%, 0.50 g) and shaken at 22° C. for 17 h. The resin was filtered off, and washed with dichloromethane (3×10 ml) and ether (2×10 ml). The residue in THF (10 ml) was treated with cyclopentylamine (88 I) and di-isopropylethylamine (0.16 ml), and the mixture was shaken at 22° C. for 17 h. The mixture was filtered, washed with THF-methanol (3:1, 2×10 ml), and the filtrate and washings were evaporated in vacuo. Purification by automated preparative HPLC afforded the title compound (20 mg).

LC/MS (system A) R$_t$=4.48 min

Mass spectrum m/z 468 (MH$^+$)

EXAMPLE 30

(2R,3R,4S,5R)-2-(5-tert-Butyl-2H-pyrazol-3-yl)-5-(6-cyclopentylamino-purin-9-yl)-tetrahydro-furan-3, 4-diol {9-[6R-(5-tert-Butyl-2H-pyrazol-3-yl)-2,2-dimethyl-tetrahydro-(3aR,6aR)-furo[3,4-d][1,3]dioxol-4R-yl]-9H- purin-6-yl}-cyclopentylamine (20 mg) was dissolved in trifluoroacetic acid-water (9:1, 4 ml) and the mixture was allowed to stand at 0–5° C. for 17 h. The solution was evaporated in vacuo (bath temp <30° C.) and quenched with 2M sodium carbonate (15 ml). The mixture was extracted with ethyl acetate (2×15 ml), and the combined extracts dried (Na$_2$SO$_4$) and evaporated in vacuo. The residue was purified by chromatography on silica gel (Varian Bondelut cartridge), eluting with ethyl acetate-methanol (9:1), to afford the title compound as a clear gum (19 mg).

LC/MS (system A) R$_t$=4.0 min

Mass spectrum m/z 428 (MH$^+$)

Experimental Details for Route (L)

Intermediate 38

3-Ethyl-5-(6R-methoxy-2,2-dimethyl-tetrahydro-(3aR, 6aR)-furo[3,4-d][1,3]dioxol-4S-yl)-isoxazole To a stirring mixture of 4R-ethynyl-6R-methoxy-2,2-dimethyl-tetrahydro-(3aR,6aR)-furo[3,4-d][1,3]dioxole [lit. compd.; ref: *Helv. Chim. Acta* 1980, 63, 1181–1189.] (0.271 g) and phenyl isocyanate (0.328 ml) in dry toluene (1.5 ml) under nitrogen, was added a mixture of 1-nitropropane (0.134 ml) and triethylamine (0.038 ml) in dry toluene (1 ml) over 5 min. A precipitate was formed slowly during the addition. The resultant mixture was heated at between 73° C. to 82° C. for 18 h. The cooled reaction mixture was filtered through silica gel, washed well with ether and then 40% ethyl acetate:cyclohexane. Removal of solvent in vacuo gave a light brown solid (0.487 g) which was subjected to flash chromatography on silica gel, eluting with ethyl acetate: cyclohexane 20:80–30:70, to give the title compound as a clear oil (0.329 g).

TLC (cyclohexane-ethyl acetate 3:2) R$_f$=0.49.

Intermediate 39a Acetic Acid 4R,5S-diacetoxy-2S-(3-ethyl-isoxazol-5-yl)-tetrahydro-furan-3R-yl Ester and Intermediate 39b Acetic Acid 4R,5R-diacetoxy-2S-(3-ethyl-isoxazol-5-yl)-tetrahydro-furan-3R-yl Ester A solution of 3-ethyl-5-(6R-methoxy-2,2-dimethyl-tetrahydro-(3aR,6aR)-furo[3,4-d][1,3]dioxol-4S-yl)-isoxazole (0.355 g) in a mixture of trifluoroacetic acid (5 ml) and water (0.05 ml) was stirred at room temperature for 27 h and then evaporated in vacuo. The residue was azeotroped with toluene (×3), dissolved in dry dichloromethane (10 ml) under nitrogen, and cooled to 0° C. 4-(N,N-dimethylamino) pyridine (0.048 g), triethylamine (8.3 ml) followed by acetic anhydride (2.49 ml) were added. The mixture was stirred at 0° to room temperature overnight. The resultant mixture was evaporated in vacuo to give a brown liquid (1.34 g). Purification by flash chromatography on silica gel, eluting with ethyl acetate:cyclohexane 20:80–40:60, afforded acetic acid 4R,5S-diacetoxy-2S-(3-ethyl-isoxazol-5-yl)-tetrahydro-furan-3R-yl ester (0.192 g) as a light brown oil, followed by acetic acid 4R,5R-diacetoxy-2S-(3-ethyl-isoxazol-5-yl)-tetrahydro-furan-3R-yl ester (0.16 g) as a light brown oil.

Intermediate 39a SiO$_2$ TLC (Cyclohexane-ethyl acetate 3:2), R$_f$=0.28

Intermediate 39b SiO$_2$ TLC (Cyclohexane-ethyl acetate 3:2), R$_f$=0.22

Intermediate 40

Acetic Acid 4R-acetoxy-2 R-(2,6-dichloro-purin-9-yl)-5S-(3-ethyl-isoxazol-5-yl)-tetrahydro-furan-3R-yl Ester To a mixture of acetic acid 4R,5S-diacetoxy-2S-(3-ethyl-isoxazol-5-yl)-tetrahydro-furan-3R-yl ester and acetic acid 4R,5R-diacetoxy-2S-(3-ethyl-isoxazol-5-yl)-tetrahydro-furan-3R-yl ester (0.909 g) in dry acetonitrile (5 ml) at room temperature under nitrogen was added 2,6-dichloropurine (0.779 g), DBU (0.692 ml) followed by trimethylsilyl triflate (0.99 ml). The reaction was stirred at room temperature for 20 h, and quenched with saturated aqueous sodium bicarbonate solution (30 ml). Extraction with ethyl acetate (3×40 ml) gave a brown liquid (3.54 g). Purification by flash chromatography on silica gel, eluting with ethyl acetate:cyclohexane 40:60-50:50, gave the title compound as a creamy white foam (0.798 g).

TLC SiO$_2$ (Cyclohexane-ethyl acetate 2:3), R$_f$=0.25.

Intermediate 41

Acetic Acid 4R-acetoxy-2R-[2-chloro-6-1S-hydroxymethyl-2-phenyl-ethylamino)-purin-9-yl]-5S-(3-ethyl-isoxazol-5-yl)-tetrahydro-furan-3R-yl Ester Acetic acid 4R-acetoxy-2R-(2,6-dichloro-purin-9-yl)-5S-(3-ethyl-isoxazol-5-yl)-tetrahydro-furan-3R-yl ester (151 mg), (S)-phenylalaninol (53 mg) and di-isopropylethylamine (67 I) were dissolved in isopropanol (2 ml) and heated at 50° C. for 7.5 h. The solvent was removed in vacuo to afford the crude title compound as a clear gum. (260 mg)

LC/MS (system) R$_t$=4.63 min

Mass spectrum m/z 585/587

EXAMPLE 31

(2R,3R,4S,5S)-2-[6-(1S-hydroxymethyl-2-phenyl-ethylamino)-2-methoxy-purin-9-yl]-5-(3-ethyl-isoxazol-5-yl)-tetrahydrofuran-3,4-diol Acetic acid 4R-acetoxy-2R-[2-chloro-6-(1 S-hydroxymethyl-2-phenyl-ethylamino)-purin-9-yl]-5S-(3-ethyl-isoxazol-5-yl)-tetrahydro-furan-3R-yl ester (259 mg) was added to 25% sodium methoxide in methanol (4 ml) and the mixture stirred at 22° C. for 8 h. The solvent was removed in vacuo and the residue purified by flash chromatography over silica gel, eluting with ethyl acetate-methanol (10:1) to give the title compound as a pale yellow gum (101 mg).

LC/MS (system A) R$_t$ 4.04 min

Mass spectrum m/z 497 (MH$^+$)

Experimental Details for Route (M)

Intermediate 42

(3aS,4S,6R,6aR)-2,2-Dimethyl-6-(6-oxo-1,6-dihydro-purin-9-yl)-cyclopenta[1,3]dioxole-4-carboxylic Acid Potassium permanganate (3.0 g) and potassium hydroxide (1.0 g) in water (60 ml) were stirred together at room temperature overnight and the solution then cooled to 0° C. [3aS-(3a,4,6,6a)]1,9-dihydro-9-[tetrahydro-6-(hydroxymethyl)-2,2-dimethyl-4H-cyclopenta-1,3-dioxol-4-yl]-6H-purin-6-one (2.92 g) was added slowly such that the temperature of the reaction mixture was maintained below 5° C. The mixture was stirred at room temperature for 5 h then cooled to 0° C. and treated with sodium metabisulfite (4.2 g). Hydrochloric acid (5M) was added cautiously to adjust the pH to about 3.5. The solution was stored at 4° C. overnight and the resultant precipitate collected, washed with chilled water and dried in vacuo. The title compound was obtained as a white solid (1.82 g).

Mass spectrum m/z 321 (MH$^+$)

Intermediate 43

6-Chloro-9-[2,2-dimethyl-6S-(3-cyclopropyl-[1,2,4] oxadiazol-5-yl)-tetrahydro-(3aS,6aR)-cyclopenta[1,3] dioxol-4R-yl]-9H-purine (3aS,4S,6R,6aR)-2,2-Dimethyl-6-(6-oxo-1,6-dihydro-purin-9-yl)-cyclopenta [1,3]dioxole-4-carboxylic acid (118 mg) in anhydrous chloroform (4.5 ml) was heated to reflux with dimethylformamide (29 I) and thionyl chloride (108 I) for 4 h. After cooling to room temperature the excess solvent and reagents were removed by evaporation and the residue taken up in anhydrous chloroform (1.5 ml). The mixture was added to a cooled (0° C.) solution of cyclopropylamidoxime (110 mg) and pyridine (41 I) in chloroform (2.5 ml). The mixture was heated to reflux for 24 h. After cooling, the mixture was evaporated to dryness and the residue purified by flash chromatography on silica gel), eluting with ethyl acetate/cyclohexane (40:60). On evaporation the title compound was obtained as a colourless gum (56 mg).

Mass spectrum m/z 403 (MH+)

Intermediate 44

(1R,2S,3R,5S)-3-(6-Chloro-purin-9-yl)-5-(3-cyclopropyl-[1,2,4]oxadiazol-5-yl)-cyclopentane-1,2-diol 6-Chloro-9-[2,2-dimethyl-6S-(3-cyclopropyl-[1,2,4]oxadiazol-5-yl)-tetrahydro-(3aS,6aR)-cyclopenta[1,3]dioxol-4R-yl]-9H-purine (50 mg) was treated with cold (0° C.) trifluoroacetic acid-water (2 ml; 9:1). The mixture was stored at 4° C. overnight and evaporated to dryness. The title compound was obtained as a colourless gum (60 mg).

Mass spectrum m/z 363 (MH+)

EXAMPLE 32

(1S,2R,3S,5R)-3-(3-cyclopropyl-[1,2,4]oxadiazol-5-yl)-5-[2S-hydroxy-cyclopent-(S)-ylamino-purin-9-yl]-cyclopentane-1,2-diol (1R,2S,3R,5S)-3-(6-Chloro-purin-9-yl)-5-(3-cyclopropyl-[1,2,4]oxadiazol-5-yl)-cyclopentane-1,2-diol (57 mg) in isopropanol (5 ml) was treated with trans-(1S, 2S)-2-aminocyclopentanol hydrochloride (34 mg) and diisopropylethylamine (85 μl) at reflux temperature overnight. The excess solvent was evaporated and the residue purified by automated preparative hplc. The title compound was obtained as a near colourless glass (15 mg).

LC/MS (System C): $R_t$=2.4 min

Mass spectrum m/z 428 (MH+)

Experimental Details for Route (N)

Intermediate 45

9-{(3aR,4R,6S,6a R)-6-[3-(tert-butyl)-1,2,4-oxadiazol-5-yl]-2,2-dimethyltetrahydrofuro[3,4-d][1,3]dioxol-4-yl}-6-(1H-1,2,3-benzotriazol-1-yloxy)-9H-purine To a solution of (3aS,4S,6R,6aR)-6-(6-chloro-purin-9-yl)-2,2-dimethyl-tetrahydro-furo[3,4-d][1,3]dioxole-4-carboxylic acid (10 g) in dimethylformamide (200 ml) was added 1-hydroxybenzotriazole (3.96 g) and 1-(3-dimethylaminopropyl)-3-ethyl-carbodiimide hydrochloride (5.62 g). t-Butylacetamidoxime (3.40 g) in dimethylformamide (30 ml) was added and the mixture was stirred at 20° C. for 24 h under nitrogen. The mixture was then heated at 70° C. for a further 36 h. The resulting mixture was then cooled to 20° C., basified with a saturated solution of sodium bicarbonate (200 ml) and extracted with ethyl acetate (2×150 ml). The organic layers were washed with brine (300 ml), dried (MgSO4), evaporated to dryness in vacuo and triturated with ether to give a yellow solid (11.08 g). Purification by chromatography on silica gel, eluting with ethyl acetate:cyclohexane (3:7), afforded the title compound (4.75 g) as a white solid.

LC/MS (System C): $R_t$=3.46 min

Mass Spectrum m/z 520 [MH+]

Intermediate 46:

9-{(3aR,4R,6S,6aR)-6-[3-(tert-butyl)-1,2,4-oxadiazol-5-yl]-2,2-dimethyltetrahydrofuro[3,4-d][1,3]dioxol-4-yl}-N-isobutyl-9H-purin-6-amine To a solution of 9-{(3aR,4R,6S,6aR)-6-[3-(tert-butyl)-1,2,4-oxadiazol-5-yl]-2,2-dimethyltetrahydrofuro[3,4-d][1,3]dioxol-4-yl}-6-(1H-1,2,3-benzotriazol-1-yloxy)-9H-purine (50 mg) in dimethylsulfoxide (0.4 ml) was added diisopropylethylamine (0.1 ml) and isobutylamine (0.038 ml). The mixture was stirred at 20° C. for 16 h under nitrogen. The mixture was then evaporated to dryness in vacuo to give a residue that was purified by automated preparative HPLC to afford the title compound (14 mg) as a white compound.

LC/MS (system C): $R_t$=3.38

Mass Spectrum m/z 458 [MH+]

EXAMPLE 45

(2S,3S,4R,5R)-2-[3-(tert-butyl)-1,2,4-oxadiazol-5-yl]-5-[6-(isobutylamino)-9H-purin-9-yl] tetrahydrofuran-3,4-diol A solution of 9-{(3aR,4R,6S,6aR)-6-[3-(tert-butyl)-1,2,4-oxadiazol-5-yl]-2,2-dimethyltetrahydrofuro[3,4-d][1,3]dioxol-4-yl}-N-isobutyl-9H-purin-6-amine (14 mg) in a cold mixture of trifluoroacetic acid:water (9:1; 1 ml) was kept at 4° C. for 18 h. The resulting solution was basified in an ice bath with saturated aqueous sodium bicarbonate (20 ml), extracted with ethyl acetate (2×20 ml), the extracts dried (MgSO4) and evaporated to dryness in vacuo to afford the title compound (7.66 mg) as a white solid.

LC/MS (System C):$R_t$=2.85 min

Mass Spectrum m/z 418 [MH+]

Experimental Details for Route (O)

Intermediate 47:

9-{(3aR,4R,6S,6aR)-6-[3-(tert-butyl)-1,2,4-oxadiazol-5-yl]-2,2-dimethyltetrahydrofuro[3,4-d][1,3]dioxol-4-yl}-N-(2,4-difluorophenyl)-9H-purin-6-amine 9-{(3aR,4R,6S,6aR)-6-[3-(tert-butyl)-1,2,4-oxadiazol-5-yl]-2,2-dimethyltetrahydrofuro[3,4-d][1,3]dioxol-4-yl}-6-(1H-1,2,3-benzotriazol-1-yloxy)-9H-purine (50 mg) was dissolved in 2,4-difluoroaniline (0.4 ml) and the mixture heated at 80° C. for 96 h. The mixture was then cooled to 20° C. and partitioned between dichloromethane (25 ml) and 1 M hydrochloric acid (15 ml). The separated aqueous phase was further extracted with dichloromethane (1×25 ml) and the combined organic extracts were evaporated to dryness in vacuo. Purification by automated preparative HPLC afforded the title compound (18.3 mg) as a dark purple gum.

LC/MS (System C): $R_t$=2.85 min

Mass Spectrum m/z 418 [MH+]

EXAMPLE 49

(2S,3S,4R,5R)-2-[3-(tert-butyl)-1,2,4-oxadiazol-5-yl]-5-[6-(2,4-difluoroanilino)-9H-purin-9-yl] tetrahydrofuran-3,4-diol A solution of 9-{(3aR,4R,6S,6aR)-6-[3-(tert-butyl)-1,2,4-oxadiazol-5-yl]-2,2-dimethyltetrahydrofuro[3,4-d][1,3]dioxol-4-yl}-N-(2,4-difluorophenyl)-9H-purin-6-amine (18.3 mg) in a cold mixture of trifluoroacetic acid:water (9:1; 1 ml) was kept at 4° C. for 18 h. The resulting solution was basified in an ice bath with a saturated solution of sodium bicarbonate (20 ml), extracted with ethyl acetate (2×20 ml), the extracts dried (MgSO4) and evaporated to dryness in vacuo to afford the title compound (14.3 mg) as a purple solid.

LC/MS (System C): $R_t$=3.03 min

Mass Spectrum m/z 474 [MH+]

Experimental Details for Route (P)

Intermediate 48:

(3aR,4S,6R,6aR)-6-(6-chloro-9H-purin-9-yl)-N-(2-hydroxypropyl)-2,2 dimethyltetrahydrofuro[3,4-d][1,3]dioxole-4-carboxamide Thionyl chloride (4.3 ml) was added to a stirred solution of (3aS,4S,6R,6aR)-6-(6-chloro-purin-9-yl)-2,2-dimethyltetrahydro-furo[3,4-d][1,3]dioxole-4-carboxylic acid (10.0 g), in chloroform (100 ml). The mixture was heated at reflux temperature under nitrogen for 60 min. After cooling to 20° C. the solvent was removed in vacuo and the residue azeotroped with toluene (2×50 ml). A suspension of the residue in chloroform (50 ml) was added dropwise at an equal rate with a solution of 1-amino-2-propanol (2.3 ml) and diisopropylethylamine (5.1 ml) in chloroform (50 ml) over 10 min to chloroform (50 ml) at 0° C. The mixture was stirred at 20° C. for 18 hours. Phosphate buffer (pH 6.5, 100 ml) was added and the phases separated. The aqueous phase was extracted with chloroform (50 ml). The combined chloroform layers were dried with sodium sulphate and the solvent removed in vacuo to give the title compound as a white foam (6.63 g).

Mass spectrum m/z 398 [MH$^+$]

Intermediate 49:
(3aR,4S,6R,6aR)-6-(6-chloro-9H-purin-9-yl)-2.2-dimethyl-N-(2-oxopropyl)tetrahydrofuro[3,4-d][1,3]dioxole-4-carboxamide To a mixture of (3aR,4S,6R,6aR)-6-(6-chloro-9H-purin-9-yl)-N-(2-hydroxypropyl)-2,2-dimethyltetrahydrofuro[3,4-d][1,3]dioxole-4-carboxamide (6.60 g) and powdered 4A molecular sieves (10 g) in dichloromethane (165 ml) at 0° C., was added acetic acid (3.0 ml) followed by the portionwise addition of pyridinium dichromate (9.36 g). The mixture was stirred at 0° C. for 15 min and then at 20° C. for 2 hours. Isopropanol (10 ml) was added and the mixture stirred for 15 min. Silica gel (Merck 9385, 9.9 g) and ethyl acetate (165 ml) were added and the reaction stirred for a further 15 min. The mixture was filtered through celite and the filter cake washed with ethyl acetate (300 ml). The filtrate was evaporated in. vacuo to give a brown solid. Purification by flash chromatography on silica gel, eluting with dichloromethane:methanol (100:3) gave a light brown foam. Further purification by chromatography on silica gel (Merck 9385), eluting with ethyl acetate followed by ethyl acetate:methanol (100:2) gave the title compound as a white foam (4.6 g).

TLC SiO$_2$ (ethyl acetate:methanol 100:20) R$_f$=0.4

Experimental Details for Route (Q)

Intermediate 50:
(3aR,4S,6R,6a R)-N-(2-hydroxybutyl)-6-methoxy-2,2-dimethyltetrahydrofuro[3,4-d][1,3]dioxole-4-carboxamide To a solution of furo[3,4-d]-1,3-dioxole-β-D ribofuranose acid (5.0 g) in dichloromethane (50 ml) was added carbonyl diimidazole (4.83 g), the mixture was stirred for 20 min at 20° C. and 1-amino-2-butanol (2.45 g) was added and the mixture was stirred, under nitrogen, at 20° C. for 18 h. The mixture was diluted with ether (50 ml) and washed with saturated citric acid solution (100 ml) and saturated aqueous sodium bicarbonate (100 ml). The layers were separated and the organic layers concentrated in vacuo; the resulting residue was purified by flash column chromatography on silica gel, eluting with 1:1 ethyl acetate:cyclohexane, to give the title compound as a clear gum (3.81 g).

Mass Spectrum m/z 290 [MH]+

Intermediate 51:
(3aR,4S,6R,6aR)-6-methoxy-2,2-dimethyl-N-(2-oxobutyl)tetrahydrofuro[3,4-d]]1,3]dioxole-4-carboxamide To a solution of (3aR,4S,6R,6aR)-N-(2-hydroxybutyl)-6-methoxy-2,2-dimethyltetrahydrofuro[3,4-d][1,3]dioxole-4-carboxamide (3.81 g) in anhydrous dichloromethane (115 m), containing powdered 4A molecular sieves (5.7 g) at 0° C., under nitrogen, were added acetic acid (2.59 ml) and potassium dichromate (7.93 g), portionwise. The reaction mixture was stirred at 0° C. for 15 min and at 20° C. for a further 2 h. The mixture was quenched with isopropanol (40 ml) and stirred for 30 min, silica gel (Merck 9385) (40 g) and ethyl acetate (100 ml) were added, and the mixture was stirred for a further 30 min. This mixture was filtered through 'harborlite®' filter aid and the filtrate concentrated in vacuo to give a crude product which was purified by flash column chromatography on silica gel, eluting with 2:1 ethyl acetate:cyclohexane to give the title compound (1.91 g)

$^1$H nmr δ 7.405(1H, br t, —N$\overline{H}$), 5.125(1H, br s, C$\overline{H}$), 5.095(1H, dd, C$\overline{H}$), 4.655(1H, br s, C$\overline{H}$), 4.565(1H, d, C$\overline{H}$), 4.155(2H, m, C$\overline{H}_2$), 3.555(3H, s, $\overline{OMe}$), 2.505(2H, q, C$\overline{H}_2$), 1.505(3H, s, —$\overline{Me}$), 1.355(3H, s, —$\overline{Me}$), 1.105(3H, t, —C$\overline{H}_3$)

Intermediate 52:
2-[(3a R,4S,6R,6aR)-6-methoxy-2,2-dimethyltetrahydrofuro[3,4-d][1,3]dioxol-4-yl]-5-ethyl-1,3-oxazole To a solution of (3aR,4S,6R,6aR)-6-methoxy-2,2-dimethyl-N-(2-oxobutyl)tetrahydrofuro[3,4-d][1,3]dioxole-4-carboxamide (740 mg) in dry toluene (10 ml), under nitrogen was added phosphorous oxychloride (1.44 ml) and the mixture was heated under reflux for 3.5 h. The reaction mixture was cooled to 0° C., quenched with saturated aqueous sodium bicarbonate (30 mls), stirred vigorously for 30 min and extracted with ethyl acetate (4×50 ml); the organic layers were combined, washed with brine (30 ml), dried (MgSO$_4$) and concentrated in vacuo to give a crude product, which was purified by flash column chromatography on silica gel, eluting with a mixture of 5:1 to 7:2 cyclohexane:ethyl acetate, to give the title compound as a yellow oil (0.83 g).

Mass Spectrum m/z 270 [MH$^+$]

Intermediate 53:
(2S,3 R,4R,5S)-2,4-bis(acetyloxy)-5-(5-ethyl-1,3-oxazol-2-yl)tetrahydrofuran-3-yl Acetate To 2-[(3aR,4S,6R,6aR)-6-methoxy-2,2-dimethyltetrahydrofuro[3,4-d][1,3]dioxol-4-yl]-5-ethyl-1,3-oxazole (0.83 g) was added 9:1 trifluoroacetic acid:water (3.56 ml), and the mixture was stirred at 20° C. for 3.5 hours. The solvents were removed in vacuo to give an orange/brown oil. This material was dissolved in pyridine (7 ml), under nitrogen, acetic anhydride (2.76 ml) was added and the mixture was stirred at 22° C. for 18 h. The mixture was concentrated in vacuo, diluted with ethyl acetate (50 ml) and washed with 1 M HCl (50 ml), saturated aqueous sodium bicarbonate (3×50 ml) and brine (50 ml); the organic layer was dried (MgSO$_4$) and the solvent evaporated to dryness to furnish the title compound as a brown/orange oil (0.854 g)

Mass Spectrum m/z 342 [MH$^+$]

Intermediate 54:
(2R,3R,4R,5S)$_4$-(acetyloxy)-2-(6-chloro-9H-purin-9-yl)-5-(5-ethyl-1,3-oxazol-2-yl)tetrahydrofuran-3-yl Acetate To 6-chloropurine (0.854 g) was added 1,1,1,3,3,3-hexamethyldisilazane (4 ml) and toluene (15 ml) and the mixture was heated under reflux for 2 h. The solvent was removed in vacuo, the residue azeotroped with toluene (1×8 ml) and the mixture evaporated to dryness. To this residue was added (2S,3R,4R,5S)-2,4-bis(acetyloxy)-5-(5-ethyl-1,3-oxazol-2-yl)tetrahydrofuran-3-yl acetate (0.854 g) in acetonitrile (20 ml), trimethylsilyl triflate (0.624 ml) and 1,8-diazabicyclo[5.4.0]undec-7-ene (0.374 ml). The reaction mixture was stirred at 20° C. for 18 h and at 80° C. for 3 h and then allowed to cool. The mixture was poured into saturated aqueous bicarbonate (40 ml) and extracted with dichloromethane (4×40 ml); the organic layers were combined, dried (MgSO$_4$) and the solvent removed in vacuo to give a crude product which was purified by flash chromatography on silica gel, eluting with 4:1 then 3:2 cyclohexane:ethyl acetate, to furnish the title compound as a clear gum (355 mg).

Mass Spectrum m/z 436 [MH+]

EXAMPLE 84

2-({9-[(2R,3R,4S,5S)-5-(5-ethyl-1,3-oxazol-2-yl)-3, 4-hydroxytetrahydrofuran-2-yl]-9H-purin-6-yl}amino)-N,N-dimethylethanesulfonamide To a solution of (2R,3R,4R,5S)-4-(acetyloxy)-2-(6-chloro-9H-purin-9-yl)-5-(5-ethyl-1,3-oxazol-2-yl) tetrahydrofuran-3-yl acetate (50 mg) in isopropanol (5 ml), N,N-diisopropylethylamine (0.120 ml) and N,N-dimethyl-2-aminoethanesulphonamide hydrochloride (86 mg) were added. The mixture was stirred at reflux temperature, under nitrogen, for 48 h and then cooled. A methanol/ammonia solution (4 ml) was added, the mixture was shaken and left to stand for 24 h. The solvent was evaporated and the the resulting residue purified by automated preparative HPLC to give the title product (8.6 mg).

Mass Spectrum m/z 468 [MH+]

Experimental Details for Route (R)

Intermediate 55:

N-{9-[(3aR,4R,6S,6aR)-2,2-dimethyl-6-(3-methyl-1,2,4-oxadiazol-5-yl)tetrahydrofuro[3,4-d][1,3]dioxol-4-yl]-9H-purin-6-yl}-N-cyclopentylamine A mixture of (3aS,4S,6R,6aR)-6-(6-cyclopentylamino-purin-9-yl)-2,2-dimethyl-tetrahydro-furo[3,4-d][1,3] dioxole-4-carboxylic acid (0.2 g), 2-ethoxy-1-ethoxycarbonyl-1,2-dihydroquinoline (146 mg), acetaldoxime (76 mg) and dimethoxyethane (DME, 25 ml) was heated under reflux for 4 days and then cooled to 22° C. The mixture was concentrated in vacuo and ethyl acetate (40 ml) added to the residue. The resulting suspension was washed with 0.5M citric acid solution (3×20 ml) and the aqueous washings were extracted with ethyl acetate (2×20 ml). The combined organic extracts were washed with water (20 ml) and brine (30 ml) and dried (MgSO$_4$). After concentration in vacuo the residue was purified by chromatography on silica gel, eluting with ethyl acetate:cyclohexane (1:1), to give the title compound (63 mg).

NMR (CDCl$_3$) δ 8.03 (1H,br.s.,heterocyclic CH); 7.84 ( 1H,s,heterocyclic CH); 6.29 (1H,br.s,CH); 5.84 ( 1H,dd,CH); 5.64 (1H,d,CH); 5.48 (1H,d,CH); 4.56 ( 1H,br.s,CH); 2.19 (3H,s,Me); 1.85-1.5 ( 9H,m+S,6×1/2CH$_2$+Me); 1.45 (3H,s,Me); 1.25-0.85 (2H,m, 2×1/2CH$_2$).

EXAMPLE 39

(2R,3R,4S,5S)-2-[6-(cyclopentylamino)-9H-purin-9-yl]-5-(3-methyl-1,2,4-oxadiazol-5-yl) tetrahydrofuran-3,4-diol A mixture of N-{9-[(3aR,4R,6S,6aR)-2,2-dimethyl-6-(3-methyl-1,2,4-oxadiazol-5-yl)tetrahydrofuro[3,4-d][1,3] dioxol-4-yl]-9H-purin-6-yl}-N-cyclopentylamine (63 mg), trifluoroacetic acid (1 ml) and water (0.1 ml) was stirred at 0° for 6 h and then diluted with ethyl acetate (20 ml). The mixture was neutralised with sodium bicarbonate solution and the aqueous phase was extracted with ethyl acetate (2×10 ml). The combined organic extracts were washed with water (8 ml) and brine (10 ml) and dried (MgSO$_4$). After concentration in vacuo the residue was purified by flahs column chromatography on silica gel, eluting with ethyl acetate:methanol (19:1) to give the title compound as a white foam (42 mg).

TLC SiO$_2$ (ethyl acetate:methanol 19:1) R$_f$ 0.30

NMR (DMSO) δ 8.43 (1H,s,CH); 8.20 (1H,br.s,CH); 7.79 (1H,br.d,NH); 6.45 (2H, v.br.S,2×OH); 6.16 (1H,d,CH); 5.24 (1H,d,CH); 4.89 (1H,t,CH); 4.73 (1H,t,CH); 4.58 ( 1H,br.m,CH); 2.42 (3H,s,Me); 2.10-1.50 (8H,m,4×CH$_2$)

Experimental Details for Route (S)

Intermediate 56:

1-[(3aR,4R,6R,6aR)-6-methoxy-2,2-dimethVitetrahydrofuro[3,4-d][1,3]dioxol-4-yl]pent-1-yn-3-ol A solution of 4R-ethynyl-6R-methoxy-2,2-dimethyl-tetrahydro-(3aR,6aR)-furo[3,4-d][1,3]dioxole (1.5 g) in tetrahydrofuran (20 ml) was cooled to −78° C. for 15 minutes under nitrogen. A solution of propionaldehyde (1.09 ml) in tetrahydrofuran (0.5 ml) was added via syringe and stirring continued for 5 h. The mixture was allowed to warm to 22° C. and stirred for a further 16 h. The solvents were removed in vacuo and the resultant orange oil partitioned between ether and aqueous ammonium chloride. The organic layers were washed with further aqueous ammonium chloride, dried (MgSO$_4$), and concentrated in vacuo to afford a yellow oil. Purification by chromatography on silica gel (Varian Bondelut cartridge), eluting with (i) cyclohexane, (ii) dichloromethane, (iii) ether, (iv) ethyl acetate afforded the title compound as a colourless oil (1.33 g).

TLC SiO$_2$ (ether:cyclohexane 1:1) R$_f$=0.39

Intermediate 57:

1-[(3aR,4R,6R,6aR)-6-methoxy-2,2-dimethyltetrahydrofuro[3,4-d][1,3]dioxol-4-yl]pent-1-yn-3-one A solution of 1-[(3aR,4R,6R,6aR)-6-methoxy-2,2-dimethyltetrahydrofuro[3,4-d][1,3]dioxol-4-yl]pent-1-yn-3-ol (1.3 g) in dichloromethane (100 ml) was added to a stirred suspension of manganese dioxide (60 g) in dichloromethane at 0° C. The mixture was stirred at 0° C. for 3 h, filtered through magnesium sulphate (50 g) and the solvent removed in vacuo to give the title compound as a colourless oil (550 mg).

NMR δ (CDCl$_3$) 5.07 (1H,s,CH); 4.97 (1H,d,CH); 4.93 ( 1H,s,CH); 4.68 (1H,d,CH); 3.41 (3H,s,OMe); 2.58 ( 2H,q,CH$_2$); 1.47 (3H,s,Me); 1.31 (3H,s,Me); 1.14 ( 3H,t,Me).

Intermediate 58:

1-[(3aR,4R,6R,6aR)-6-methoxy-2,2-dimethyltetrahydrofuro[3,4-d][1,3]dioxol-4-yl]pentane-1,3-dione 1-oxime A mixture of 1-[(3aR,4R,6R,6aR)-6-methoxy-2,2-dimethyltetrahydrofuro[3,4-d][1,3]dioxol-4-yl]pent-1-yn-3-one (550 mg) and hydroxylamine (50% solution in water) (0.2 ml) in ethanol (10 ml) was stirred overnight at 22° C. The mixture was concentrated in vacuo to afford the title compound as a yellow oil (554 mg).

NMR δ (CDCl$_3$) 5.36, 5.31 (1H,2×d,CH); 5.00 ( 1H,d,CH); 4.92 (1H,d,CH); 4.65 (1H,2×d,CH); 3.40, 3.35 ( 3H,2×s,OMe); 3.03-2.85 (2H,2×AB,CH$_2$); 1.92 ( 2H,m,CH$_2$); 1.50, 1.34 (6H,2×s,2×Me); 1.03 (3H,2×t,Me).

Intermediate 59:

(3R,4S,5R)-5-(5-ethylisoxazol-3-yl)tetrahydrofuran-2,3,4-triol

1-[(3aR,4R,6R,6aR)-6-methoxy-2,2-dimethyltetrahydrofuro[3,4-d][1,3]dioxol-4-yl]pentane-1,3-dione 1-oxime (0.5 g) was dissolved in aqueous acetic acid (18 mg) and the mixture heated at 100° C. for 2 h. The solution was cooled and concentrated in vacuo to afford a brown oil which was azeotroped with toluene. Purification by chromatography on silica gel (Varian Bondelut silica gel cartridge), eluting with (i) dichloromethane, (ii) ether, (iii) ethyl acetate, (iv) methanol, gave the title compound (150 mg).

TLC SiO$_2$ (ether) R$_f$=0.17
Intermediate 60:
(2R,3 R,4R)4,5-bis(acetyloxy)-2-(5-ethylisoxazol-3-yl) tetrahydrofuran-3-yl Acetate (3R,4S,5R)-5-(5-ethylisoxazol-3-yl)tetrahydrofuran-2,3,4-triol isomer 1 (150 mg) was dissolved in pyridine (4 ml) and the mixture treated with acetic anhydride (0.983 ml). The resulting solution was stirred at 22° C. for 18 h. The mixture was concentrated in vacuo to afford a brown oil. Purification by chromatography on silica gel (Varian Bondelut SiO$_2$ cartridge), eluting with (i) dichloromethane, (ii) ether (iii) ethyl acetate, afforded the title compound as a pale yellow solid (142 mg).

TLC SiO$_2$ (ether) R$_f$=0.53
Intermediate 61:
(2R,3R,4R,5R)4-(acetyloxy)-2-(2,6-dichloro-9H-purin-9-yl)-5-(5-ethylisoxazol-3-yl)tetrahydrofuran-3-yl Acetate (2R,3 R,4R)-4,5-bis(acetyloxy)-2-(5-ethyl isoxazol-3-yl) tetrahydrofuran-3-yl acetate isomer 1 (193 mg) was dissolved in acetonitrile (5 ml) and treated sequentially with 2,6-dichloropurine (213 mg), 1,8-diazabicyclo[5.4.0]undec-7-ene (DBU) (0.186 ml) and trimethylsilyl trifluoromethanesulphonate (TMSOTf) (0.225 ml) via a syringe over 5 min. The clear yellow solution was stirred at 22° C. for 40 h, at 60° C. for 21 h, and at 80° C. for 6 h. The mixture was cooled to room temperature and more DBU (0.186 ml) and TMSOTf (0.225 ml) were added. After stirring at 22° C. for 36 h the yellow mixture was heated at 60° C. overnight and at 80° C. for 6 h. The solvents were removed in vacuo and the resultant brown oily solid taken up in ethyl acetate and washed with water (20 ml, 3:1). The aqueous layer was extracted with ethyl acetate and the combined organic layers dried (MgSO$_4$) and evaporated in vacuo to afford a brown oily solid. The residue was triturated with dichloromethane and a white solid removed by filtration. Evaporation of the filtrate afforded a tan solid. Purification by flash chromatography on silica gel eluting with ether:cyclohexane (1:1) afforded the title compound as a white solid (161 mg).

LC/MS (System C) R$_t$=3.34 min.
Mass spectrum m/z 470, 472 [MH$^+$], [MH+2$^+$]
Intermediate 62:
(2R,3R,4R,5R)-4-(acetyloxy)-2-[2-chloro-6-[(1-ethylpropyl)amino]-9H-purin-9-yl}-5-(5-ethylisoxazol-3-yl)tetrahydrofuran-3-yl Acetate (2R,3R,4 R,5R)-4-(acetyloxy)-2-(2,6-dichloro-9H-purin-9-yl)-5-(5-ethylisoxazol-3-yl)tetrahydrofuran-3-yl acetate (125 mg) was dissolved in isopropanol (5 ml) and the solution was treated with diisopropylethylamine (0.06 ml) followed by 1-ethylpropylamine (0.044 ml). The mixture was heated at 50° C. under nitrogen for 16 h. The solvent was removed in vacuo and the mixture partitioned between ethyl acetate and 1 M hydrochloric acid. The organic layers were washed with saturated sodium bicarbonate solution and brine, dried (MgSO$_4$) and evaporated in vacuo. Purification by chromatography on silica gel (Varian Bondelut cartridge), eluting with (i) dichloromethane, (ii) ether and (iii) ethyl acetate, gave the title compound as a colourless oil (108 mg). TLC SiO$_2$ (ether) Rf=0.26.

EXAMPLE 163

(2R,3R,4S,5R)-2-{2-chloro-6-[(1-ethylpropyl) amino]-9H-purin-9-yl}-5-(5-ethylisoxazol-3-yl) tetrahydrofuran-3,4-diol Formate A mixture of (2R,3R,4R,5R)-4-(acetyloxy)-2-{2-chloro-6-[(1-ethylpropyl)amino]-9H-purin-9-yl}-5-(5-ethylisoxazol-3-yl)tetrahydrofuran-3-yl acetate (30 mg) and 2-morpholinoethylamine (0.037 ml) was heated at 90° C. for 24 h in dimethylsulphoxide (0.5 ml). Heating was continued for 60 h at 90° C. Purification by preparative HPLC (gradient profile 5–95% (ii) over 18.25 min) gave the title compound as a white solid (6 mg).

LC/MS (System C) R$_t$=3.41 min.
Mass Spectrum m/z 437 [MH$^+$]
Experimental Details for Route (T)
Intermediate 63:
9-{(3aR,4R,6S,6aR)-6-[5-(tert-butyl)-1,3,4-oxadiazol-2-yl]-2,2-dimethyltetrahydrofuro[3,4-d][1,3]dioxol-4-yl}-N-(4-chloro-2-fluorophenyl)-9H-purin-6-amine 9-[6S-(5-tert-Butyl-[1,3,4]oxadiazol-2-yl)-2,2-dimethyl-tetrahydro-(3aR,6aS)-furo[3,4-d][1,3]dioxol-4R-yl]-6-chloro-9H-purine (2.8 g) was treated with 4-chloro-2-fluoro-aniline (4.48 ml), palladium acetate (146 mg) and (R)-2,2'-bis(diphenylphosphino)-1,1'-binaphthyl (620 mg) in dry toluene (34 ml) and the mixture stirred at room temperature for 5 mins (reaction carried out in seven portions). Caesium carbonate (3.08 g, in seven portions) was added, and the mixtures heated at 86–96° C. for 16 h. The mixtures were combined and partitioned between water (200 ml) and dichloromethane (3×120 ml). The organic layers were washed with brine, dried (MgSO$_4$) and evaporated in vacuo to give a brown oil (8.7 g). Purification by chromatography on silica gel, eluting with ethyl acetate:cyclohexane 30:70 gave an off-white solid (2.35 g).

LC/MS (System C) R$_t$=3.41 min
Mass Spectrum m/z 530 [MH$^+$]

Example 14

(2S,3S,4R,5R)-2-(5-tert-Butyl-[1,3,4]oxadiazol-2-yl)-5-[6-(4-chloro-2-fluoro-phenylamino)-purin-9-yl]-tetrahydro-furan-3,4-diol 9-{(3aR,4R,6S,6aR)-6-[5-(tert-butyl)-1,3,4-oxadiazol-2-yl]-2,2-dimethyltetrahydrofuro[3,4-d][1,3]dioxol-4-yl}-N-(4-chloro-2-fluorophenyl)-9H-purin-6-amine (2.35 g) was dissolved in trifluoroacetic acid (20 ml) and water (2 ml) with ice bath cooling, and the mixture allowed to stand at 4° C. for 17 h. The mixture was poured slowly into ice cold saturated aqueous sodium bicarbonate (400 ml) and extracted with ethyl acetate (3×200 ml). The organic layers were washed with brine, dried (MgSO$_4$) and evaporated in vacuo to give the title compound as a buff solid (2.30 g).

LC/MS (System C) R$_t$=3.04 min.
Mass Spectrum m/z 490 [MH$^+$]
Experimental Details for Route (U)
Intermediate 64:
9-[6S-(5-tert-Butyl-[1,3,4]oxadiazol-2-yl)-2,2-dimethyl-tetrahydro-(3aR,6aS)-furo[3,4-d][1,3]dioxol-4R-yl]-6-chloro-9H-purine 1-Deoxy-1-(1,6-dihydro-6-oxo-9H-purin-9-yl)-2,3, -O-(1-methylethylidene)-β-D-ribofuranonic acid[1] (0.4 g) was dissolved in tetrahydrofuran (10 ml), diisopropylethylamine (0.075 ml) was added and the reaction mixture was stirred at 0° C. for 10 min. Pivaloyl chloride (0.016 ml) was then added to the mixture and the reaction was stirred at 0° C. for 3 h. t-Butylhydrazide trifluoroacetate (0.36 g) was dissolved in tetrahydrofuran, cooled to 0° C. and treated with diisopropylethylamine (0.24 ml); this solution was then added to the reaction mixture. The reaction was allowed to warm up to 20° C. and stirred for 20 h. The solvent was removed in vacuo and the resulting residue purified by flash chromatography (silica gel, eluting with 5% methanol in dichloromethane) to afford the corresponding diacylhydrazide (0.41 g).

The diacylhydrazide intermediate (30 mg) was dissolved in dimethylformamide (3 ml) and cooled to 0° C. Phosphorus oxychloride (45 mg) was added, and the reaction mixture stirred at room temperature for 18 h, and at 90° C. for 2 h. The solvent was removed in vacuo, and the resulting residue, was purified by automated preparative HPLC to afford the title compound (20 mg).

[1]·R. A. Olsson et al. J. Med. Chem., 1986, 29, 1683

Experimental Details for Route (V)

Intermediate 65:

(2R,3R,4R,5S)4-(acetyloxy)-5-{3-[(acetyloxy)methyl]isoxazol-5-yl}-2-(6-chloro-9H-purin-9-yl)tetrahydrofuran-3-yl Acetate To 6-chloropurine (1.08 g) was added 1,1,1,3,3,3-hexamethyldisilazane (20 ml) and the mixture heated at 100° C., under nitrogen for 2.5 h. The reaction was allowed to cool, the solvent was removed in vacuo, the residue azeotroped with anhydrous toluene (2×2.5 ml) and the mixture evaporated to dryness to give an off-white solid. To this solid was added acetic acid 4R-acetoxy-2S-(3-acetoxymethyl-isoxazol-5-yl)-5R-methoxy-tetra hydro-furan-3R-yl ester (450 mg) in anhydrous acetonitrile (15 ml) under nitrogen, the mixture was cooled to 0° C. and trimethylsilyl trifluoromethanesulphonate (1.4 ml) added. The mixture was allowed to warm up to 20° C. over 20 min, then heated to 80° C. for 16 h. After cooling, the mixture was poured into saturated aqueous sodium bicarbonate (40 ml) and extracted with ethyl acetate (3×70 ml); the organic layers were combined, washed with brine (50 ml), dried ($MgSO_4$) and concentrated to dryness to give a crude porduct which was purified by flash column chromatography on silica gel, eluting with 1:1 ethyl acetate:cyclohexane to furnish the title compound as a clear oil (310 mg).

LC/MS (System C) $R_t$=2.76 min

Mass Spectrum m/z 480/482 [MH$^+$]/[MH+2$^+$]

EXAMPLE 155

(2R,3R,4S,5S)-2-(6-{[(1S,2S)-2-hydroxycyclopentyl]amino}-9H-purin-9-yl)-5-[3-(hydroxymethyl)isoxazol-5-yl]tetrahydrofuran-3,4-diol To a solution of (2R,3R,4R,5)-4-(acetyloxy)-5-{3-[(acetyloxy)methyl]isoxazol-5-yl}-2-(6-chloro-9H-purin-9-yl)tetrahydrofuran-3-yl acetate (20 mg) in isopropyl alcohol (2 ml) was added N,N-diisopropylethylamine (0.043 ml) and 2-hydroxycyclopentylamine hydrochloride (11.4 mg). The mixture was stirred at 50° C., under nitrogen for 18 h, cooled and evaporated to dryness in vacuo. The resulting residue was purified by automated preparative HPLC (gradient profile 5%-90% (ii) over 20 min) to give the intermediate triacetoxy protected product. To this residue was added methanol (1 ml) and t-butylamine (0.013 ml) and the mixture was stirred at 0° C. for 3 hours. The solvent evaporated in vacuo to yield title compound as a white solid (5 mg).

LC/MS (System C) $R_t$=2.25 min

Mass Spectrum m/z 419 [MH$^+$]

Experimental Details for Route (W)

Intermediate 66:

(2R,3R,4R,5R)4-(acetyloxy)-2-ethynyl-5-methoxytetrahydrofuran-3-yl Acetate

4R-Ethynyl-6R-methoxy-2,2-dimethyl-tetrahydro-(3aR,6aR)-furo[3,4-d][1,3]dioxole (0.965 g) was heated under reflux with conc. hydrochloric acid (1.0 ml) in methanol (30 ml) for 6 h. The methanol was evaporated in vacuo, more methanol added, and heating under reflux continued for 16 h. Pyridine (1.6 ml) was added, the methanol evaporated in vacuo, more methanol was added, and the mixture was evaporated to dryness in vacuo. Dry toluene (10 ml) was added and the mixture again evaporated to dryness. The residue was dissolved in dry dichloromethane and treated with pyridine (1.6 ml), 4-dimethylaminopyridine (25 mg), and acetic anhydride (1.37 ml), and the mixture was stirred at 22° C. under nitrogen for 18 h. The mixture was evaporated to dryness in vacuo and the residue partitioned between saturated aqueous citric acid (100 ml) and dichloromethane (2×75 ml). The organic layers were washed with saturated aqueous sodium bicarbonate, dried ($MgSO_4$) and evaporated in vacuo to give a pale yellow oil (1.19 g). Purification by chromatography on silica gel (10 g Varian Bondelut cartridge), eluting with ethyl acetate: cyclohexane 5:95-30:70) gave the title compound as a colourless oil (724 mg).

TLC $SiO_2$ (Ethyl acetate:cyclohexane 25:75) $R_f$=0.3

Intermediate 67:

(2R,3R,4R,5R)-4-(acetyloxy)-2-(6-chloro-9H-purin-9-yl)-5-ethynyltetrahydrofuran-3-yl Acetate 6-Chloropurine (250 mg) was heated at 130° (oil bath) with hexamethyldisilazane (6 ml) with stirring under nitrogen for 2 h. The excess reagent was evaporated in vacuo and the residue azeotroped with dry toluene (3×5 ml) to give a pale yellow solid. (2R,3R,4R,5R)-4-(acetyloxy)-2-ethynyl-5-methoxytetrahydrofuran-3-yl acetate (121 mg) was azeotroped with dry toluene (2×5 ml), dissolved in dry acetonitrile, and added to the silylated purine, followed by trimethylsilyl trifluoromethanesulphonate (0.334 ml). The mixture was heated at 73-740 for 2 h. The mixture was poured into saturated aqueous sodium bicarbonate and extracted with ethyl acetate (3×60 ml). The organic layers were washed with brine, dried ($MgSO_4$) and evaporated in vacuo to give a yellow oil (203 mg). Purification by chromatography on silica gel (Varian Bondelut cartridge), eluting with ethyl acetate:cyclohexane 10:90-60:40, gave the title compound as a colourless gum (84 mg).

TLC $SiO_2$ (Ethyl acetate:cyclohexane 50:50) $R_f$=0.25

Intermediate 68:

(2R,3R,4R,5R)-4-(acetyloxy)-2-[6-(1H-1,2,3-benzotriazol-1-yloxy)-9H-purin-9-yl]-5-ethynyltetrahydrofuran-3-yl Acetate (2R,3R,4R,5R)-4-(acetyloxy)-2-(6-chloro-9H-purin-9-yl)-5-ethynyltetrahydrofuran-3-yl acetate (104 mg) was treated with 1-hydroxybenzotriazole (136 mg) in dry DMF (3 ml) for 45 h at 22° C. The mixture was poured into ice cooled 1M hydrochloric acid (50 ml) and extracted with dichloromethane (3×25 ml); the organic layers were washed with water (20 ml) and saturated aqueous sodium bicarbonate (20 ml), dried ($MgSO_4$) and evaporated in vacuo to give a colourless gum (148 mg).

LC/MS (System C): $R_t$ 3.19 min.

Mass Spectrum m/z 464 [MH$^+$]

Intermediate 69:

(2R,3R,4R,5R)-4-(acetyloxy)-2-[6-(4-chloro-2-fluoroanilino)-9H-purin-9-yl]-5-ethynyltetrahydrofuran-3-yl Acetate (2R,3R,4R,5R)4-(acetyloxy)-2-[6-(1H-1,2,3-benzotriazol-1-yloxy)-9H-purin-9-yl]-5-ethynyltetrahydrofuran-3-yl acetate was treated with 2-fluoro-4-chloroaniline (0.63 ml), and the mixture was heated at 60° C. for 22.5 h. The mixture was purified by chromatography on silica gel (Varian Bondelut cartridge), eluting with ethyl acetate:cyclohexane 10:90-60:40, to give the title compound (55 mg).

TLC SiO$_2$ (Ethyl acetate:cyclohexane 50:50) R$_f$=0.3
Intermediate 70:
(2R,3R,4R,5S)$_4$-(acetyloxy)-5-(3-bromoisoxazol-5-yl)-2-[6-(4-chloro-2-fluoroanilino)-9H-purin-9-yl]tetrahydrofuran-3-yl Acetate (2R,3 R,4R,5R)$_4$-(acetyloxy)-2-[6-(4-chloro-2-fluoroanilino)-9H-purin-9-yl]-5-ethynyltetrahydrofuran-3-yl acetate (20 mg) was stirred at 22° C. with dibromoformaldoxime (12.5 mg), sodium bicarbonate (39 mg), water (0.075 ml) and ethyl acetate (1.5 ml) for 88 h. The mixture was partitioned between water (20 ml) and ethyl acetate (3×10 ml), the organic layers were washed with brine and evaporated in vacuo to give a brown gum (19 mg). Purification by chromatography on silica gel (Varian Bondelut cartridge), eluting with ethyl acetate:cyclohexane 20:80-80:20) gave the title compound as a colourless gum (16.8 mg).

LC/MS (System C) R$_t$=3.6 min
Mass Spectrum m/z 595, 597 [MH$^+$], [MH+2$^{+}$]

EXAMPLE 164

(2S,3S,4R,5R)-2-(3-bromoisoxazol-5-yl)-5-[6-(4-chloro-2-fluoroanilino)-9H-purin-9-yl]tetrahydrofuran-3,4-diol (2R,3 R,4R,5S)-4-(acetyloxy)-5-(3-bromoisoxazol-5-yl)-2-[6-(4-chloro-2-fluoroanilino)-9H-purin-9-yl]tetrahydrofuran-3-yl acetate (16.8 mg) was treated with t-butylamine (0.08 ml) in methanol (0.8 ml) at 0° C. for 1.5 h, and the mixture was evaporated to dryness to give the title compound (16 mg).

LC/MS (System C) R$_t$=3.22 min
Mass Spectrum m/z 511 [MH$^+$]
Experimental Details for Route (Wb)

EXAMPLE 144

(2R,3R,4S,5S)-2-[6-(4-chloro-2-fluoroanilino)-9H-purin-9-yl]-5-(3-methylisoxazol-5-yl)tetrahydrofuran-3,4-diol (2R,3R,4R,5R)-4-(acetyloxy)-2-(6-chloro-9H-purin-9-yl)-5-ethynyltetrahydrofuran-3-yl acetate (20 mg) was dissolved in anhydrous toluene (0.5 ml) and treated with triethylamine (0.006 ml), nitroethane (0.004 ml) and phenyl isocyanate (0.012 ml). The reaction was heated at 100° C. for 24 h, cooled to room temperature and concentrated in vacuo. The resulting residue was purified by automated preparative HPLC, to produce an intermediate which was then dissolved in anhydrous methanol, cooled to 0° C. and treated with t-butylamine (0.02 ml) for 1 h. The reaction mixture was concentrated in vacuo, to afford the title compound as a white solid (143 mg).

LC/MS (system C) R$_t$=2.95 min
Mass Spectrum m/z 447 [MH$^+$]
Experimental Details for Route (X)

EXAMPLE 130

(2R,3R,4S,5R)-2-[6-(cyclopentylamino)-9H-purin-9-yl]-5-(1,5-dimethyl-1H-1,2,4-triazol-3-yl)tetrahydrofuran-3,4-diol Trifluoroacetate {9-[2,2-Dimethyl-6R-(5-methyl-4H-[1,2,4]triazol-3-yl)-tetrahydro-(3aR,6aR)-furo[3,4-d][1,3]dioxol-4R-yl]-9H-purin-6-yl}-cyclopropyl-amine (250 mg) was dissolved in anhydrous toluene (10 ml) and treated with dimethylformamide dimethyl acetal (0.47 ml). The mixture was heated at reflux temperature for 7 h. and then, cooled to 20° C. and concentrated in vacuo. The resulting residue was purified by flash chromatography on silica gel, eluting with ethyl acetate: methanol 19:1. The resulting intermediate was treated with a mixture of trifluoroacetic acid/water (9:1) at 0° C. for 6 h. The reaction mixture was then concentrated in vacuo, to afford, after trituration with ethyl acetate, the title compound as a white solid (143 mg).

Analysis: Found (%): C 44.4; H 4.8; N 20.4
Required for C$_{18}$H$_{24}$N$_8$O$_3$.CF$_3$CO$_2$H.1.5H$_2$O: C 44.4; H 5.2; N 20.7
Experimental Details for Route (Z)
Intermediate 71:
(2R,3R,4R,5R)4-(acetyloxy)-2-[(acetyloxy)methyl]-5-[2-chloro-6-(4-chloro-2-fluoroanilino)-9H-purin-9-yl]tetrahydrofuran-3-yl Acetate To a stirred solution of 2,6-dichloro-9-(2,3,5-tri-O-acetyl-β-D-ribofuranosyl)-9H-purine $^2$(1.0 g) in toluene (25 ml) was added palladium acetate (50 mg), 4-chloro-2-fluoroaniline (0.5 ml) and bis[2-(diphenylphosphino)phenyl] ether $^3$(120 mg) and the reaction stirred at 20° C. for 15 min. Caesium carbonate (872 mg) was added and the mixture heated at 90° C. for 16 hours. The reaction mixture was cooled to 20° C. and partitioned between ethyl acetate (100 ml) and water (100 ml). The organic layer was washed with brine (100 ml), dried with magnesium sulphate and the solvent removed in vacuo. Purification by flash chromatography on silica gel, eluting with ethyl acetate:cyclohexane (1:1) gave the title compound (400 mg).

Mass Spectrum m/z 556 [MH$^+$]

2. M. J. Robins and B. Uznanski Canad. J. Chem., 1981, 59(17), 2608

3. J. P. Sadighi, M. C. Harris and S. L. Buchwald Tett. Lett. 1998, 5327-5330

Intermediate 72:
{(3aR,4R,6R,6aR)-6-[2-chloro-6-(4-chloro-2-fluoroanilino)-9H-purin-9-yl]-2,2-dimethyltetrahydrofuro[3,4-d][1,3]dioxol-4-yl}methanol To a suspension of (2R,3R,4R,5R)-4-(acetyloxy)-2-[(acetyloxy)methyl]-5-[2-chloro-6-(4-chloro-2-fluoroanilino)-9H-purin-9-yl]tetrahydrofuran-3-yl acetate (400 mg) in methanol (7 ml), sodium methoxide, 25% in methanol, (3 drops) was added. On stirring for 15 min at 20° C. the reaction mixture went clear. On stirring at 20° C. for a further 90 min a precipitate formed. The precipitate was collected by filtration and dried in vacuo for 16 hours. This was dissolved in a mixture of acetone (15 ml) and 2-2-dimethoxypropane (3 ml), and para-toluene sulphonic acid (193 mg) added. The mixture was stirred at 20° C. for 3 hours. The solvent was removed in vacuo and the residue dissolved in ethyl acetate (50 ml), washed with water (50 ml) and brine (30 ml), dried (MgSO$_4$) and the solvent removed in vacuo. Purification by chromatography on silica gel (Varian Bondelut cartridge), eluting with cyclohexane: ethyl acetate (1:1) gave the title compound as a white foam (240 mg).

Mass Spectrum 470 m/z [MH$^+$]
Experimental Details for Route (Y)
Intermediate 73:
tert-Butyl 4-[(9-{(2R,3R,4R,5S)-3,4-bis(acetyloxy)-5-[3-(tert-butyl)isoxazol-5-yl]tetrahydrofuran-2-yl}-9H-purin-6-yl)amino]piperidine-1-carboxylate To a solution of acetic acid 4R-acetoxy-5S-(3-tert-butyl-isoxazol-5-yl)-2R-(6-chloro-purin-9-yl)-tetrahydro-furan-3R-yl ester (455 mg) in isopropanol (20 ml) was added tert-butyl-4-amino-1-piperidinecarboxylate (785 mg) and diisopropylethylamine (1.03 ml). The mixture was heated at 95° C. for 60 h. The resulting mixture was then cooled and evaporated to dryness in vacuo. The resulting residue was dissolved in pyridine (20 ml) and acetic anhydride (19 ml) was added. The mixture was stirred at room temperature for 16 h, evaporated to dryness in vacuo and redissolved in ethyl acetate (50 ml). Citric acid (2×50 ml) was added to the mixture and the layers separated. The aqueous layers were extracted with ethyl acetate (100 ml). The combined ethyl acetate layers were dried (MgSO$_4$), filtered and evaporated to dryness in vacuo to afford the title product (500 mg) as a yellow solid.

LC/MS (System C): R$_t$=3.59 min

Mass Spectrum m/z 628 [MH$^+$]

Intermediate 74:

(2R,3R,4R,5S)-4-(Acetyloxy)-5-[3-(tert-butyl)isoxazol-5-yl]-2-[6-(piperidin-4-ylamino)-9H-purin-9-yl] tetrahydrofuran-3-yl Acetate tert-Butyl 4-[(9-{(2R,3R,4R,5S)-3,4-bis(acetyloxy)-5-[3-(tert-butyl)isoxazol-5-yl]tetrahydrofuran-2-yl}-9H-purin-6-yl)amino]piperidine-1-carboxylate (500 mg) was dissolved in trifluoroacetic acid:dichloromethane (1:9, 20 ml) and the mixture kept at 3° C. for 16 h. The mixture was then quenched with saturated sodium bicarbonate solution (100 ml) and extracted with dichloromethane (100 ml). The organic layer was washed with saturated sodium bicarbonate solution (100 ml) and evaporated to dryness in vacuo to afford the title compound (407 mg) as a yellow glassy solid.

LC/MS (system C): R$_t$=2.45 min

Mass Spectrum m/z 528 [MH$^+$]

Intermediate 75:

(2R,3R,4R,5S)-4-(acetyloxy)-5-[3-(tert-butyl)isoxazol-5-yl]-2-(6-{[1-(methylsulfonyl)piperidin-4-yl]amino}-9H-purin-9-yl)tetrahydrofuran-3-yl Acetate To a solution of (2R,3R,4R,5S)-4-(Acetyloxy)-5-[3-(tert-butyl)isoxazol-5-yl]-2-[6-(piperidin-4-ylamino)-9H-purin-9-yl]tetrahydrofuran-3-yl acetate (40 mg) in tetrahydrofuran (4 ml) was added methanesulfonyl chloride (0.0088 ml) and triethylamine (0.0212 ml). The reaction mixture was stirred for 16 h at 20° C., and partitioned between ethyl acetate (2×100 ml) and water (100 ml). The organic layers were washed with water (100 ml), dried (MgSO$_4$), and evaporated in vacuo to afford the title compound (36.7 mg) as a colourless gum.

LC/MS (System C): R$_t$=3.20 min

Mass Spectrum m/z 606 [MH$^+$]

EXAMPLE 167

(2S,3S,4R,5R)-2-[3-(tert-butyl)isoxazol-5-yl]-5-(6-{] 1-(methylsulfonyl)piperidin-4-yl]amino}-9H-purin-9-yl)tetrahydrofuran-3,4-diol (2R,3R,4R,5S)$_4$-(Acetyloxy)-5-[3-(tert-butyl)isoxazol-5-yl]-2-(6-{[1-(methylsulfonyl)piperidin-4-yl]amino}-9H-purin-9-yl)tetrahydrofuran-3-yl acetate (36.7 mg) was dissolved in chilled methanol (2 ml) and tert-butylamine (0.038 ml) was added at 0° C. The mixture was kept at 3° C. for 1.5 h, and evaporated in vacuo to afford the title compound as a white solid (30.8 mg).

LC/MS (System C): R$_t$=2.69 min

Mass Spectrum m/z 522 [MH$^+$]

Experimental Details for Route (Bb)

Intermediate 76:

(2R,3R,4R,5S)-4-(acetyloxy)-5-{3-[(acetyloxy)methyl] isoxazol-5-yl}-2-[2-chloro-6-(4-chloro-2-fluoroanilino)-9H-purin-9-yl]tetrahydrofuran-3-yl Acetate To acetic acid 4R-acetoxy-5S-(3-acetoxymethyl-isoxazol-5-yl)-2R-(2,6-dichloro-purin-9-yl)-tetrahydrofuran-3R-yl ester (50 mg) in toluene (2 ml) was added palladium (II) acetate (2.2 mg), 2,2'-bis(diphenylphosphino)-1,1'-binaphthyl (6 mg) and 4-chloro-2-fluoroaniline (28.5 mg). The mixture was stirred under nitrogen for 20 min, cesium carbonate (38 mg) was added, and stirring was continued at 80° C. for 24 h. The mixture was cooled, diluted with ethyl acetate (25 ml), washed with water (25 ml) and brine (25 ml), and evaporated in vacuo. Purification by automated preparative HPLC (gradient profile 5–90% (ii) over 18.5 min) gave the title compound as a white solid (3.02 mg).

LC/MS (System C) R$_t$=3.52 min

Mass Spectrum m/z=623 [MH$^+$]

Intermediate 77:

(2R,3R,4S,5S)-2-[2-chloro-6-(4-chloro-2-fluoroanilino)-9H-Purin-9-yl]-5-[3-(hydroxymethyl)isoxazol-5-yl] tetrahydrofuran-3,4-diol To (2R,3R,4R,5S)4-(acetyloxy)-5-{3-[(acetyloxy) methyl]isoxazol-5-yl}-2-[2-chloro-6-(4-chloro-2-fluoroanilino)-9H-purin-9-yl]tetrahydrofuran-3-yl acetate (4.02 mg) in methanol (2 ml) at 0° C. was added tert-butylamine (0.012 ml), and the mixture was allowed to stand at 0° C. for 3 h. The solvent was evaporated in vacuo to furnish the title compound as a yellow gum (2.48 mg).

LC/MS (System C) R$_t$=3.10 min

Mass Spectrum m/z=497 [MH$^+$]

Experimental Details for Route Cc

Intermediate 78:

(3aR,4S,6R,6aR)-N'-acetyl-6-[6-(4-chloro-2-fluoroanilino)-9H-purin-9-yl]-2,2-dimethyltetrahydrofuro[3,4-d[]1,3] dioxole-4-carbohydrazide To a stirred solution of (3aR,4S,6R,6aR)-6-[6-(4-chloro-2-fluoroanilino)-9H-purin-9-yl]-2,2-dimethyltetrahydrofuro [3,4-d][1,3]dioxole-4-carbohydrazide (50 mg) in N,N'-dimethylformamide (2 ml) at 0° C. was added diisopropylethylamine (28 µl) and acetyl chloride (9 mg). The reaction mixture was stirred at 0° C. for 5 h. The mixture was partitioned between ethyl acetate (20 ml) and water (20 ml). The organic layer was washed with brine (20 ml), dried (MgSO$_4$) and the solvent removed in vacuo. The residue was purified by automated preparative HPLC (gradient profile 5–95% (ii) over 18.5 min) to give the title compound (25 mg).

LC/MS: R$_t$=2.87 min

Mass Spectrum m/z 506 [MH$^+$]

Subsequent steps analogous to route A.

Reporter Gene Experiments

Agonist activity was measured in Chinese hamster ovary (CHO) cells containing the CRE/SPAP/HYG (CRE=cyclic AMP response element; HYG=hygromycin resistance; SPAP=secreted placental alkaline phosphatase) reporter gene elements, which upon stimulation of cAMP levels produced SPAP. A cell line was used, which was stably transfected with either the human adenosine A1 receptor or the human adenosine A3 receptor in addition to the above elements. Cells were plated out in 96-well plates in culture medium and incubated at 37° C. for 1 hour. For measurement of potency, agonists were added to the appropriate wells at a concentration range of approximately $10^{-10}$-$10^{-5}$M. 15Min later, cAMP levels were stimulated by addition of a maximal concentration of forskolin. All cells were then incubated for a further 5 hours at 37° C., and cooled to room temperature, after which a substrate for the phosphatase (para-nitrophenol phosphate, pNPP), which is converted by SPAP to a coloured reagent) was then added and the 96-well -plates were read in a plate reader. From these readings, the concentration-dependence of the inhibition by the agonist for forskolin-stimulated SPAP production can be calculated. One of the agonists tested on each 96-well plate was the standard non-selective agonist, N-ethylcarboxamidoadenosine (NECA), and the potency of all test agonists is expressed relative to that of the NECA standard.

(ECR=equipotent concentration ratio relative to NECA=1)

TABLE 2

Potencies in the reporter gene assay

| Example No. | Adenosine A1 receptor ECR* | Adenosine A3 receptor ECR* |
|---|---|---|
| 3 | 4.16 | 152 |
| 4 | 5.65 | 152 |
| 6 | 1.71 | 134 |
| 12 | 2.28 | 254 |
| 14 | 5.8 | 1066.71 |
| 16 | 9.6 | 201 |
| 19 | 5.15 | 172 |
| 21 | 23.26 | 321 |
| 22 | 8.75 | 423 |
| 28 | 0.42 | 44.7 |
| 37 | 4.19 | 507 |
| 44 | 7.68 | 165.54 |
| 45 | 7.36 | 165.54 |
| 51 | 7.56 | 587.75 |
| 54 | 20.78 | 715.31 |
| 56 | 15.96 | 717.99 |
| 62 | 29.47 | 327 |
| 67 | 9.8 | 827.66 |
| 68 | 4.09 | 417.37 |
| 108 | 1.52 | 254 |
| 116 | 27.26 | 955 |
| 119 | 2.83 | 154 |
| 123 | 4.19 | 325.44 |
| 126 | 13.9 | |
| 127 | 0.21 | 21.62 |
| 129 | 15.5 | >199 |
| 131 | 0.15 | 199.01 |
| 132 | 0.53 | >22.4 |
| 133 | 25.47 | 466.92 |
| 134 | 3.28 | >245.4 |
| 135 | 0.48 | |
| 136 | 1.95 | |
| 138 | 1.31 | |
| 139 | 10.64 | 228 |
| 141 | 12.08 | 228 |
| 143 | 19.6 | >74.1 |
| 144 | 2.8 | |
| 145 | 24.9 | |
| 163 | 1.34 | 232 |
| 164 | 4.3 | |
| 177 | 2.01 | 122 |
| 178 | 7.42 | >471 |
| 179 | 12.6 | |
| 180 | 18.1 | >471 |
| 181 | 8.57 | |
| 182 | 3.48 | |

*ECR = equipotent concentration ratio relative to NECA = 1 (see description in Reporter Gene Assay)

What is claimed is:

1. A method of treating a patient suffering from ischaemic heart disease, peripheral vascular disease or stroke or which subject is suffering pain comprising administration of a therapeutically effective amount to said patient of a compound of formula (I):

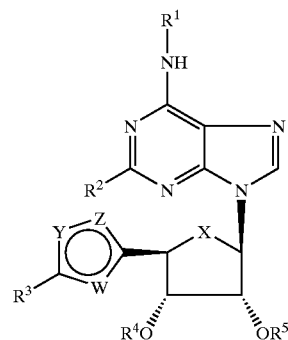

wherein X represents O or $CH_2$;

$R^2$ represents $C_{1-3}$alkyl, $C_{1-3}$alkoxy, halogen or hydrogen;

$R^3$ represents H, phenyl (optionally substituted by halogen), a 5 or 6 membered heteroaryl group, $C_{1-6}$ alkoxy, $C_{1-6}$ alkylO$(CH_2)_n$ where n is 0–6, $C_{3-7}$ cycloalkyl, $C_{1-6}$ hydroxyalkyl, halogen or a $C_{1-6}$ straight or branched alkyl, $C_{1-6}$ alkenyl or $C_{1-6}$ alkynyl group optionally substituted by one or more halogens;

Y and Z represent O, N, CH, or N($C_{1-6}$ alkyl);

W represents OH, O, N, S, or N($C_{1-6}$ alkyl); and wherein at least one of W and Z represents a heteroatom and when Y, Z and/or W is N, the presence or absence of an additional H would be apparent to a person skilled in the art; with the proviso that when W represents CH, Z represents N and Y represents O, $R^3$ cannot be H or $CH_3$;

$R^4$ and $R^5$ independently represent H or a $C_{1-6}$ straight chain or branched alkyl group;

$R^1$ represents hydrogen or a group selected from the group consisting of:

(1)-(alk)$_n$—$C_{3-7}$) cycloalkyl or-(alk)$_n$—($C_{3-7}$) bridged cycloalkyl, wherein either group may be optionally substituted by one or more substituents selected from OH, halogen, and —($C_{1-3}$) alkoxy, wherein (alk) represents $C_{1-3}$ alkylene and n represents 0 or 1;

(2) an aliphatic heterocyclic group of 4 to 6 membered rings containing at least one heteroatom which is O, N or S, optionally substituted by one or more substituents selected from the group consisting of —($C_{1-3}$)alkyl, —CO2—($C_{1-4}$)alkyl, —CO($C_{1-3}$alkyl), —S(=O)$_n$—($C_{1-3}$alkyl), —CONR$^a$R$^b$ (wherein R$^a$ and R$^b$ independently represent H or $C_{1-3}$alkyl) and =O; where there is a sulfur atom in the heterocyclic ring, said sulfur is optionally substituted by (=O)$_n$, where n is 1 or 2;

(3) straight or branched $C_{1-12}$ alky, optionally modified by the introduction of one or more O, S(=O)$_n$ (where n is 0, 1 or 2) or N-H groups between carbon atoms of the alkyl chain said alkyl group being optionally substituted by one or more of the following groups, phenyl, halogen, hydroxy, $C_{3-7}$ cycloalkyl or NR$^a$R$^b$ wherein R$^a$ and R$^b$ independently represent hydrogen, $C_{3-7}$ cycloalkyl or a $C^{1-6}$ straight chain or branched alkyl optionally substituted by $C_{3-7}$ cycloalkyl;

(4) a fused bicyclic aromatic ring:

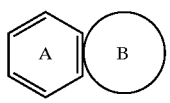

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —$CO_2$—($C_{1-3}$alkyl);

(5) a phenyl group optionally substituted by one or more substituents selected from the group consisting of: -halogen, —$SO_3H$, -(alk)$_n$OH, -(alk)$_n$-cyano, —(O)$_n$—($C_{1-6}$)alkyl (optionally substituted by one or more halogens), -(alk)$_n$ -nitro, —(O)$_m$ -(alk)$_n$— $CO_2R^c$, -(alk)$_n$ —$SO_2NR^cR^d$, -(alk)$_n$$OR^c$, -(alk)$_n$ (CO)$_m$NHSO$_2R^e$, -(alk)$_n$ —NHCOR$^c$, and -(alk)$_n$— NR$^c$R$^d$ wherein m and n are 0 or 1 and alk represents a $C_{1-6}$ alkylene group or $C_{2-6}$ alkenyl group, R$^e$ represents $C_{1-3}$ alkyl; and (6) a phenyl group substituted by a 5 or 6 membered heterocyclic aromatic group, said heterocyclic aromatic group optionally being substituted by $C_{1-3}$ alkyl or NR$^c$R$^d$;

R$^c$ and R$^d$ may each independently represent hydrogen, or $C_{1-3}$ alkyl or when part of a group NR$^c$R$^d$, R$^c$ and R$^d$ together with the nitrogen atom may form a 5 or 6 membered heterocyclic ring which heterocyclic ring may optionally be substituted further by one or more $C_{1-3}$ alkyl groups; or a physiologically acceptable solvate or salt thereof.

2. A method of treating a patient suffering from a condition where there is an advantage in decreasing plasma free fatty acid concentration, or reducing heart rate comprising administration to said patient of a therapeutically effective amount of a compound of formula (I):

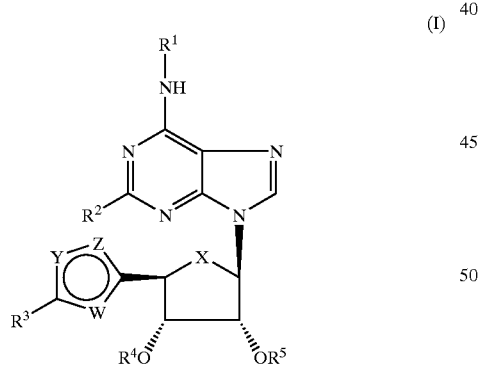

(I)

wherein X represents O or $CH_2$;

R$^2$ represents $C_{1-3}$ alkyl, $C_{1-3}$ alkoxy, halogen or hydrogen;

R$^3$ represents H, phenyl (optionally substituted by halogen), a 5 or 6 membered heteroaryl group, $C_{1-6}$ alkoxy, $C_{1-6}$ alkylO(CH$_2$)$_n$ where n is 0–6, $C_{3-7}$cycloalkyl, $C_{1-6}$ hydroxyalkyl, halogen or a $C_{1-6}$ straight or branched alkyl, $C_{1-6}$ alkenyl or $C_{1-6}$ alkynyl group optionally substituted by one or more halogens;

Y and Z represent O, N, CH, or N($C_{1-6}$ alkyl);

W represents CH, O, N, S, or N($C_{1-6}$ alkyl); and wherein at least one of W and Z represents a heteroatom and when Y, Z and/or W is N, the presence or absence of an additional H would be apparent to a person skilled in the art; with the proviso that when W represents CH, Z represents N and Y represents O, R$^3$ cannot be H or CH$^3$;

R$^4$ and R$^5$ independently represent H or a $C_{1-6}$ straight chain or branched alkyl group;

R$^1$ represents hydrogen or a group selected from the group consisting of:

(1) -(alk)$_n$ —($C_{3-7}$) cycloalkyl or -(alk)$_n$—($C_{3-7}$) bridged cycloalkyl, wherein either group may be optionally substituted by one or more substituents selected from OH, halogen, and —($C_{1-3}$) alkoxy, wherein (alk) represents $C_{1-3}$ alkylene and n represents 0 or 1;

(2) an aliphatic heterocyclic group of 4 to 6 membered rings containing at least one heteroatom which is O, N or S, optionally substituted by one or more substituents selected from the group consisting of —($C_{1-3}$)alkyl, —CO2—($C_{1-4}$)alkyl, —CO($C_{1-3}$alkyl), —S(=O)$_n$—($C_{1-3}$alkyl), —CONR$^a$R$^b$ (wherein R$^a$ and R$^b$ independently represent H or $C_{1-3}$alkyl) and =O; where there is a sulfur atom in the heterocyclic ring, said sulfur is optionally substituted by (=O)$_n$, where n is 1 or 2;

(3) straight or branched $C_{1-12}$ alkyl, optionally modified by the introduction of one or more O, S(=O)$_n$ (where n is 0, 1 or 2) or N-H groups between carbon atoms of the alkyl chain said alkyl group being optionally substituted by one or more of the following groups, phenyl, halogen, hydroxy, $C_{3-7}$ cycloalkyl or NR$^a$R$^b$ wherein R$^a$ and R$^b$ independently represent hydrogen, $C_{3-7}$ cycloalkyl or a $C_{1-6}$ straight chain or branched alkyl optionally substituted by $C_{3-7}$ cycloalkyl;

(4) a fused bicyclic aromatic ring:

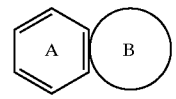

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —$CO_2$—($C_{1-3}$alkyl);

(5) a phenyl group optionally substituted by one or more substituents selected from the group consisting of: -halogen, —$SO_3H$, -(alk)$_n$OH, -(alk)$_n$ -cyano, —(O)$_n$ —($C_{1-6}$)alkyl (optionally substituted by one or more halogens), -(alk)$_n$ -nitro, —(O)$_m$ -(alk$_n$)— $CO_2R^c$, -(alk)$_n$ —$SO_2NR^cR^d$, -(alk)$_n$OR$^c$, -(alk)$_n$ —(CO)$_m$—NHSO$_2R^e$, -(alk)$_n$-NHCOR$^c$, and -(alk)$_n$ —NR$^c$R$^d$ wherein m and n are 0 or 1 and alk represents a $C_{1-6}$ alkylene group or $C_{2-6}$ alkenyl group, R$^e$ represents $C_{1-3}$ alkyl; and (6) a phenyl group substituted by a 5 or 6 membered heterocyclic aromatic group, said heterocyclic aromatic group optionally being substituted by $C_{1-3}$ alkyl or NR$^c$R$^d$;

R$^c$ and R$^d$ may each independently represent hydrogen, or $C_{1-3}$ alkyl or when part of a group NR$^c$R$^d$, R$^c$ and R$^d$ together with the nitrogen atom may form a 5 or 6 membered heterocyclic ring which heterocyclic ring may optionally be substituted further by one or more $C_{1-3}$ alkyl groups; or a physiologically acceptable solvate or salt thereof.

3. A compound of formula (Ib):

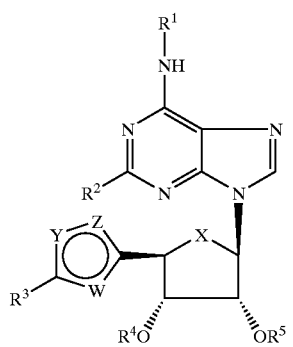

(Ib)

wherein X represents O or $CH_2$;

$R^2$ represents $C_{1-3}$ alkyl, $C_{1-3}$ alkoxy, halogen or hydrogen;

$R^3$ represents H, phenyl (optionally substituted by halogen), a 5 or 6 membered heteroaryl group, $C_{1-6}$ alkoxy, $C_{1-6}$ alkylO$(CH_2)_n$ where n is 0–6, $C_{3-7}$ cycloalkyl, $C_{1-6}$ hydroxyalkyl, halogen or a $C_{1-6}$ straight or branched alkyl, $C_{1-6}$ alkenyl or $C_{1-6}$ alkynyl group optionally substituted by one or more halogens;

Y and Z represent O, N, CH, or N($C_{1-6}$ alkyl);

W represents OH, O, N, S, or N($C_{1-6}$ alkyl); and wherein at least one of W and Z represents a heteroatom and when Y, Z or W is N, the presence or absence of an additional H would be apparent to a person skilled in the art; with the proviso that when W represents CH, Z represents N and Y represents O, $R^3$ cannot be H or $CH_3$;

$R^4$ and $R^5$ independently represent H or a $C_{1-6}$ straight chain or branched alkyl group;

$R^1$ represents hydrogen or a group selected from the group consisting of:

(1) -(alk)$_n$ —($C_{3-7}$) cycloalkyl or -(alk)$_n$ —($C_{3-7}$) bridged cycloalkyl wherein either group may be optionally substituted by one or more substituents selected from OH, halogen, —($C_{1-3}$) alkoxy, wherein (alk) represents $C_{1-3}$ alkylene and n represents 0 or 1; and (2) straight or branched $C_{1-12}$ alkyl, optionally modified by the introduction of one or more O, S(=O)$_n$ (where n is 0, 1 or 2) or N-H groups between carbon atoms of the alkyl chain, said alkyl group being optionally substituted by one or more of the following groups, phenyl, halogen, hydroxy, $C_{3-7}$ cycloalkyl or NR$^a$R$^b$ wherein R$^a$ and R$^b$ independently represent hydrogen, $C_{3-7}$ cycloalkyl or a $C_{1-6}$ straight chain or branched alkyl optionally substituted by $C_{3-7}$ cycloalkyl;

or salts or solvates thereof;

with the proviso that when $R^4$ and $R^5$ both represent H, and $R^2$ represents halogen, $R^3$ cannot represent methyl, ethyl, n-propyl, isopropyl, cyclopropyl, CH(OH)CH$_3$, or $C_{1-3}$alkoxy.

4. A compound of formula (Ic):

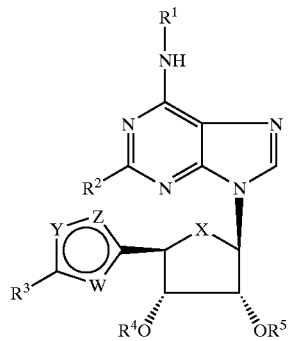

(Ic)

wherein X represents O or $CH_2$;

$R^2$ represents $C_{1-3}$ alkyl, $C_{1-3}$ alkoxy, halogen or hydrogen;

$R^3$ represents H, phenyl (optionally substituted by halogen), a 5 or 6 membered heteroaryl group, $C_{1-6}$ alkoxy, $C_{1-6}$ straight or branched alkyl optionally substituted by one or more halogens, $C_{3-7}$ cycloalkyl, $C_{1-6}$ hydroxyalkyl or halogen;

Y and Z represent O, N, or CH;

W represents CH, O, N, or S;

and wherein at least one of W and Z represents a heteroatom and when Y, Z and/or W is N, the presence or absence of an additional H would be apparent to a person skilled in the art;

with the proviso that when W represents CH, Z represents N and Y represents O, $R^3$ cannot be H or $CH_3$;

$R^4$ and $R^5$ independently represent H or a $C_{1-6}$ straight chain or branched alkyl group;

$R^1$ represents a group selected from the group consisting of:

(1) -(alk)$_n$ —($C_{3-7}$) cycloalkyl or -(alk)$_n$—($C_{3-7}$) bridged cycloalkyl, wherein either group may be optionally substituted by one or more substituents selected from OH, halogen, and —($C_{1-3}$) alkoxy, wherein (alk) represents $C_{1-3}$ alkylene and n represents 0 or 1; and (2) straight or branched $C_{1-12}$ alkyl, optionally modified by the introduction of one or more O, S(=O)$_n$ (where n is 0, 1 or 2) or N-H groups between carbon atoms of the alkyl chain said alkyl group being optionally substituted by one or more of the following groups, phenyl, halogen, hydroxy, $C_{3-7}$ cycloalkyl or NR$^a$R$^b$ wherein R$^a$ and R$^b$ independently represent hydrogen, $C_{3-7}$ cycloalkyl or a $C_{1-6}$ straight chain or branched alkyl optionally substituted by $C_{3-7}$ cycloalkyl;

or salts or solvates thereof.

5. The compound according to claim 3 wherein the W, Y and Z containing heterocyclic group is selected from the group consisting of isoxazoles, oxadiazoles, pyrazoles, oxazoles, triazoles, and thiadiazoles.

6. The compound according to claim 3 wherein the W, Y and Z containing heterocyclic group is selected from the group consisting of isoxazoles, and 1,2,4- and 1,3,4- oxadiazoles.

7. The compound according to claim 3 wherein $R^2$ represents hydrogen, methyl, methoxy or halogen.

8. The compound according to claim 3 wherein $R^1$ may represent (alk)n—$C_{3-6}$ cycloalkyl wherein n is 0 or 1 and the said cycloalkyl is either substituted by at least one substituent selected from halogen and OH, or is unsubstituted and n is zero.

9. The compound according to claim 3 wherein $R^1$ represents a straight or branched alkyl of 1–6 carbon atoms optionally with at least one S $(=O)_n$ and/or N substituted in the chain; where there is an $S(=O)_n$ in the chain.

10. A pharmaceutical composition comprising a compound of claim 3 together with a pharmaceutically acceptable diluent or carrier.

11. The compound according to claim 8 wherein the cycloalkyl group is unsubstituted or monosubstituted with OH.

12. The compound according to claim 11 wherein the cycloalkyl group is 5-membered.

13. A compound which is:

(2S,3S,4R, 5R)-2-(3-cyclopropyl-[1,2,4]oxadiazol-5-[6-(2S-hydroxy-cyclop ent-(S)-ylamino)-purin-9-yl]-tetrahydro-furan-3,4-diol;

(2S,3S,4R,5R)-2-(3-tert-butyl-[1,2,4]oxadiazol-5-yl)-5-[6-(2S-hydroxy-cyclopen t-(S)-ylamino)-purin-9-yl]-tetrahydro-furan-3,4-diol;

(2S,3S,4R,5R)-2-[3-(tert-butyl)-1,2,4-oxadiazol-5-{6-[(cyclopropylmethyl) amino]-9H-purin-9-yl}tetrahydrofuran-3,4-diol;

(2S,3S,4R,5R)-2-[3-(tert-butyl)-1,2,4-oxadiazol--5-yl]-5-[6-(isobutylamino)-9H-p urin-9-yl]tetrahydrofuran-3,4-diol;

(2R, 3R, 4S, 5S,)-2-[6-(cycloprpylamino)-9H-purin-9-yl]-5-(3-isopropyl-1,2,4-ox adiazol-5-yl)tetrahydrofuran-3,4-diol;

2({9-[(2R,3R,4R,5S)-3,4-dihydroxy-5-(3-isopropyl-1,2,4-oxadiazol-5-yl)tetrahy drofuran-2-yl]-9H-purin-6-yl}amino)-N-methylethanesulfonamide;

2[(9-{(2R, 3R, 4S, 5S)-5-(5-tetrt-butyl-(1,3,4-oxadiazol-2-yl]-3,4-dihydroxytetrah ydrofuran-2-yl}-9H-purin-6-yl)amino]-N-ethylethanesulfonamide;

2-[(9-{(2R,3R,4S,5S)-5-[5-(tert-butyl)-1,3,4-oxadiazol-2-yl]-3,4-dihydroxytetrah ydrofuran-2-yl}-9H-purin-6-yl)amino]-N-(3-methylphenyl)ethanesulfonamide;

2-{(9-[(2R,3R,4S, 5S)-3,4-dihydroxy-5-(5-methyl-1,3-oxazol-2-yl)tetrahydrofura n-2-yl]-9H-purin-6-yl}amino)-N-methylethanesulfonamide;

(2R,3R,4S,5S)-2-[6-(cyclopentylamino)-9H-purin-9-yl]-5-[3-(methoxymethyl)-1, 2,4-oxadiazol-5-yl]tetrahydrofuran-3,4-diol;

(2S,3S,4R,5R)-2-(5-ethyl-1,3,4-oxadiazol-2-yl)-5-[6-(isopropylamino)-9H-purin-9-yl ]tetrahydrofuran-3,4-diol;

(2R,3R,4S,5S)-2-(6-{[(1S,2S)-2-hydroxycyclopentyl]amino}-9H-purin-9-yl)-5-(5-methyl-1,3,4-oxadiazol-2-yl) tetrahydrofuran-3,4-diol;

(2R,3R,4S,5S)-2-{2-chloro-6-[(1-ethylpropyl)amino]-9H-purin-9-yl}-5-(3-cyclop ropyl-1,2,4-oxadiazol-5-yl)tetrahydrofuran-3,4-diol formate (1:2);

(2R,3R,4S,5S)-2-[2-chloro-6-(1-ethyl-propylamino)-purin-9-yl]-5-(3-cyclopropyl-[1,2,4]oxadiazol-5-yl)-tetrahydro-furan-3,4-diol diformate;

(2S,3S,4R,5R)-2-(3-ethylisoxazol-5-yl)-5-(6-{[(1S,2S)-2-hydroxycyclopentyl]a mino}-9H-purin-9-yl) tetrahydrofuran-3,4-diol;

(2R,3R,4S,5S)-2-(2-chloro-6-{[(1S,2S)-2-hydroxycyclopentyl]amino}-9H-purin-9-yl)-5-(3-ethylisoxazol-5-yl) tetrahydrofuran-3,4-diol;

(2R,3R,4S,5S)-2-(2-chloro-6-{[2-(ethylsulfonyl)ethyl]amino}-9H-punin-9-yl)-5-(3-ethylisoxazol-5-yl) tetrahydrofuran-3,4-diol;

(2R,3R,4S,5S)-2-(2-chloro-6-{[(1S,2S)-2-hydroxycyclopentyl]amino}-9H-purin-9-yl)-5-[3-(hydroxymethyl) isoxazol-5-yl]tetrahydrofuran-3,4-diol; and (2R, 3R,4S,5R)-2-{2-chloro-6-[(1-ethylpropyl)amino]-9H-purin-9-yl}-5-(5-ethylis oxazol-3-yl) tetrahydrofuran-3,4-diol formate; or a salt or solvate of any one thereof.

* * * * *